US009023354B2

(12) United States Patent
Errico et al.

(10) Patent No.: US 9,023,354 B2
(45) Date of Patent: May 5, 2015

(54) COMBINATION THERAPY WITH MDM2 AND EFGR INHIBITORS

(71) Applicant: Joseph P. Errico, Warren, NJ (US)

(72) Inventors: Joseph P. Errico, Warren, NJ (US); Benjamin Mugrage, Cranbury, NJ (US); Ignatius Turchi, Yardley, PA (US); Matthew Sills, Berkeley Heights, NJ (US); Jane Ong, Franklin Park, NJ (US); John Allocco, Staten Island, NY (US); Pam Wines, Manalapan, NJ (US); Margarita Bastos, Plainsboro, NJ (US)

(73) Assignee: Joseph P. Errico, Warren, NJ (US)

( * ) Notice: Subject to any disclaimer, the term of this patent is extended or adjusted under 35 U.S.C. 154(b) by 0 days.

(21) Appl. No.: 14/157,086

(22) Filed: Jan. 16, 2014

(65) Prior Publication Data

US 2014/0134163 A1 May 15, 2014

Related U.S. Application Data

(60) Division of application No. 13/188,351, filed on Jul. 21, 2011, now Pat. No. 8,658,170, which is a continuation-in-part of application No. 12/986,146, filed on Jan. 6, 2011, now Pat. No. 8,618,302, and a continuation-in-part of application No. PCT/US2011/020414, filed on Jan. 6, 2011, and a continuation-in-part of application No. PCT/US2011/020418, filed on Jan. 6, 2011.

(60) Provisional application No. 61/292,776, filed on Jan. 6, 2010, provisional application No. 61/366,480, filed on Jul. 21, 2010.

(51) Int. Cl.
| | |
|---|---|
| C07D 401/12 | (2006.01) |
| A61K 31/4709 | (2006.01) |
| A61K 31/517 | (2006.01) |
| A61K 39/395 | (2006.01) |
| C07K 16/44 | (2006.01) |

(52) U.S. Cl.
CPC .............. *C07D 401/12* (2013.01); *C07K 16/44* (2013.01); *A61K 31/4709* (2013.01); *A61K 31/517* (2013.01); *A61K 39/3955* (2013.01)
514/266.24; 514/266.4; 514/314

(58) Field of Classification Search
None
See application file for complete search history.

(56) References Cited

U.S. PATENT DOCUMENTS

| | | | |
|---|---|---|---|
| 6,465,448 B1 | 10/2002 | Gerson et al. | |
| 6,664,288 B1 | 12/2003 | Pardee et al. | |
| 6,916,455 B2 | 7/2005 | Segelke et al. | |
| 6,931,325 B2 | 8/2005 | Wall et al. | |
| 7,514,240 B2 | 4/2009 | Yokoyama et al. | |
| 7,947,712 B2 | 5/2011 | Bursavich et al. | |
| 8,119,656 B2 | 2/2012 | Roth et al. | |
| 8,138,356 B2 | 3/2012 | Chaudhary et al. | |
| 2007/0004750 A1 | 1/2007 | Lorsbach et al. | |
| 2008/0221132 A1 | 9/2008 | Cai et al. | |
| 2008/0269213 A1 | 10/2008 | Bursavich et al. | |
| 2008/0305041 A1 | 12/2008 | Manivet et al. | |
| 2009/0029949 A1 | 1/2009 | Parrill-Baker et al. | |
| 2009/0088420 A1 | 4/2009 | Neamati et al. | |
| 2009/0163545 A1 | 6/2009 | Goldfarb | |
| 2009/0233905 A1 | 9/2009 | Burke et al. | |
| 2010/0160313 A1 | 6/2010 | Neamati et al. | |
| 2010/0168163 A1 | 7/2010 | Lacrampe et al. | |
| 2011/0224207 A1 | 9/2011 | Padmanabhan et al. | |
| 2011/0294848 A1 | 12/2011 | Roxas-Duncan et al. | |

FOREIGN PATENT DOCUMENTS

| | | |
|---|---|---|
| CN | 101505751 | 8/2009 |
| WO | WO 2007/002433 | 1/2007 |
| WO | WO 2008/024922 | 2/2008 |
| WO | WO 2009/037343 | 3/2009 |
| WO | WO 2009/051801 | 4/2009 |
| WO | WO 2009/117484 | 9/2009 |
| WO | WO 2009/151972 | 12/2009 |
| WO | WO 2010/039538 | 4/2010 |
| WO | WO 2011/082175 | 7/2011 |
| WO | WO 2011/085126 | 7/2011 |

OTHER PUBLICATIONS

Ahrendt et al., Rapid p53 sequence analysis in primary lung cancer using an oligonucleotide probe array, Proc. Natl. Acad. Sci., USA, Genetics, 1999, pp. 7382-7387, vol. 96.

Akbasak et al., Oncogenes: cause or consequence in the development of glial tumors, J. Neurol. Sci., 1992, pp. 119-133, vol. 111.

Arends et al., Apoptosis. The Role of the Endonuclease, Am. J. Pathol., 1990, pp. 593-608, vol. 136, No. 3.

Atalay et al., Novel therapeutic strategies targeting the epidermal growth factor receptor (EGFR) family and its downstream effectors in breast cancer, Ann. Oncology, 2003, pp. 1346-1363, vol. 14.

Australian 1st Office Action dated Jul. 10, 2013 in related Australian Application AU 2011204368, filed Jan. 6, 2011, 7 pages. Australian 2nd Office Action dated Jul. 17, 2013 in related Australian Application AU 2011204368, filed Jan. 6, 2011, 2 pages.

Australian 3rd Office Action dated Sep. 18, 2014 in related Australian Application AU 2011204368, filed Jan. 6, 2011, 5 pages.

(Continued)

*Primary Examiner* — Timothy R Rozof

(74) *Attorney, Agent, or Firm* — Dentons US LLP

(57) ABSTRACT

Provided is a method of treating a proliferative disease, condition, or disorder in a subject by administering a combination of an inhibitor of p53 and MDM2 binding and an EGFR inhibitor. Various embodiments of the disclosed methods provide a synergistic anti-proliferative or anti-apoptotic effect compared to administration of one agent alone.

8 Claims, 5 Drawing Sheets

(56) References Cited

OTHER PUBLICATIONS

Australian 4th Office Action dated Oct. 20, 2014 in related Australian Application AU 2011204368, filed Jan. 6, 2011, 3 pages.
Bayascas et al., Isolation of AmphiCASP-3/7, an ancestral caspase from amphioxus (*Branchiostoma floridae*). Evolutionary considerations for vertebrate caspases, 2002 Cell Death Differ., pp. 1078-1089, vol. 9.
Berkson et al., Pilot Screening Programme for Small Molecule Activators of p53, Intn'l J Cancer, 2005, pp. 701-710, vol. 115, No. 5, CAS abstract, 1 page.
Berkson et al., Pilot screening programme for small molecule activators of p53, Int J Cancer, 2005, pp. 701-710, vol. 115, No. 5.
Burgess et al., An open-and-shut case? Recent Insights into the Activation of EFG/ErbB Receptors, Molecular Cell, 2003, pp. 541-552, vol. 12, No. 3.
Burgoyne et al., Mammalian Chromatin Substructure Studies with the Calcium—Magnesium Endonuclease and Two-Dimensional Polyacrylamide-Gel Electrophoresis, Biochem. J., 1974, pp. 67-72, vol. 143.
Chemical Abstracts Service, accession No. 690650-87-4, 2004, 1 page.
Chen et al., A cell-based immunocytochemical assay for monitoring kinase signaling pathways and drug efficacy, Analytical Biochemistry, 2005, pp. 136-142, vol. 338.
Chene, Inhibiting the p53-MDM2 Interaction: An Important Target for Cancer Therapy, Nature Reviews, Cancer, 2003, pp. 102-109, vol. 3.
Chinese 1st Office Action in English and Chinese dated May 28, 2013 in corresponding Chinese Patent Application CN 201180012605.7, filed Jan. 6, 2011, 8 pages.
Chinese 2nd Office Action in English and Chinese dated Apr. 17, 2014 in corresponding Chinese Patent Application CN 201180012605.7, filed Jan. 6, 2011, 19 pages.
De La Motte Rouge, A Novel Epidermal Growth Factor Receptor Inhibitor Promotes Apoptosis in Non-Small Cell Lung Cancer Cells Resistant to Erlotinib, Cancer Res., 2007, pp. 6253-6262, vol. 67, No. 13.
Dickson et al., Tyrosine kinase receptor—nuclear protooncogene interactions in breast cancer (Chapter 13), Cancer Treatment Res., Genes, Oncogenes and Hormones, 1992, pp. 249-273, vol. 61, Kluwer Academic Publishers, ISBN: 0792317483, Abstract only, 1 page.
Ding et al., Structure-Based Design of Potent Non-Peptide MDM2 Inhibitors, J. Am. Chem. Soc., 2005, pp. 10130-10131, vol. 127, No. 29.
Ding et al., Structure-Based Design of Spiro-oxindoles as Potent, Specific Small-Molecule Inhibitors of the MDM2-p53 Interaction, J. Med. Chem., 2006, pp. 3432-3435, vol. 49, No. 12.
Duh et al., Epidermal Growth Factor Receptors and Adenylate Cyclase Activity in Human Thyroid Tissues, World J. Surgery, 1990, pp. 410-418, vol. 14.
Duke et al., IL-2 addictions: withdrawal of growth factor activates a suicide program in dependent T cells, Lymphokine Res., 1986, pp. 289-299, vol. 5, Abstract only, 1 page.
Dutta et al., Cellular responses to EGFR inhibitors and their relevance to cancer therapy, Cancer letters, 2007, pp. 165-177, vol. 254, No. 2.
Duvall et al., Death and the cell, Immunol. Today, 1986, pp. 115-119, vol. 7, No. 4.
Elhai et al., Conjugal Transfer of DNA to Cyanobacteria, Methods in Enzymology, 1988, pp. 747-754, vol. 167.
European Examination Report date Jun. 24, 2014 in related European Application No. 11732163.8, 4 pages.
Extended European Search Report dated Jul. 29, 2013 in related European Application No. EP 11732160.4, 9 pages.
Extended European Search Report dated Jul. 19, 2013 in related European Application No. EP 11732163.8, 7 pages.
Supplementary European Search Report dated Mar. 19, 2014 in related European Application No. EP 11810417.3, 10 pages.
Farfan et al., Multiplexing Homogeneous Cell-Based Assays, Cell Notes, 2004, pp. 15-18, Issue 10.
Ferguson et al., EGF activates its receptor by removing interactions that autoinhibit ectodomain dimerization, Mol. Cell, 2003, pp. 507-517, vol. 11.
Fotouhi et al., Small Molecule Inhibitors of p53/MDM2 Interaction, Curr. Top. Med. Chem., 2005, pp. 159-165, vol. 5, Issue 2.
Garcio-Calvo et al., Purification and catalytic properties of human caspase family members, Cell Death Differ., 1999, pp. 362-369, vol. 6.
Gopalakrishnan et al., Application of micro arrayed compound screening (pcARCS) to identify inhibitors of caspase-3, J. Biomol. Screening, 2002, pp. 317-323, vol. 7.
Grasberger et al., Discovery and Cocrystal Structure of Benzodiazepinedione HDM2 Antagonists That Activate p53 in Cells, J. Med. Chem., 2005, pp. 909-912, vol. 48, No. 4.
Hamman et al., Synthesis and Biological Activity of a Novel Series of Nonsteroidal, Peripherally Selective Androgen Receptor Antagonists Derived from 1,2-Dihydropyridono[5,6-g]quinolines, J. Med. Chem., 1998, pp. 623-639, vol. 41, No. 4.
Hardcastle, Inhibitors of the MDM2-p53 interaction as anticancer drugs, Drugs of the Future, 2007, pp. 883-896, vol. 32, No. 10.
Herbst et al., Monoclonal Antibodies to Target Epidermal Growth Factor Receptor-Positive Tumors, Cancer, 2002, pp. 1593-1611, vol. 94, No. 5.
Hotz et al., Flow Cytometric Detection of Apoptosis: Comparison of the Assays of In Situ DNA Degradation and Chromatin Changes, Cytometry, 1994, pp. 237-244, vol. 15.
International Search Report and Written Opinion in related PCT Application No. PCT/US11/20414 dated May 26, 2011, 11 pages.
International Search Report in related PCT Application No. PCT/US11/20418 dated Jul. 7, 2011, 2 pages.
International Search Report and Written Opinion in related PCT Application No. PCT/US11/44882 dated Dec. 7, 2011, 7 pages.
Irwin et al., Zinc—A Free Database of Commercially Available Compounds for Virtual Screening, J. Chem. Inf. Model, 2005, pp. 177-182, vol. 45, No. 1.
Issaeva et al. Small molecule RITA binds to p53, blocks p53—HDM-2 interaction and activates p53 function in tumors, Nature Med., 2004, pp. 1321-1328, vol. 10, No. 4.
Karvinen et al., Homogeneous time-resolved fluorescence quenching assay (LANCE) for capsase-3, J. Biomol. Screen, 2002, pp. 223-231, vol. 7.
Korc et al., Overexpression of the epidermal growth factor receptor in human pancreatic cancer is associated with concomitant increases in the levels of epidermal growth factor and transforming growth factor alpha, J. Clin. Invest., 1992, pp. 1352-1360, vol. 90.
Kumabe et al., Amplification of alpha-platelet-derived growth factor receptor gene lacking an exon coding for a portion of the extracellular region in a primary brain tumor of glial origin, Oncogene, 1992, pp. 627-633, vol. 7, No. 4, Abstract only, 1 page.
Larson et al., Perform Multiplexed Cell-Based Assays on Automated Platforms, Cell Notes, 2005, pp. 13-16, No. 12.
Lawrence et al., Identification of a Disruptor of the MDM2-p53 Protein-Protein Interaction Facilitated by High-throughput in Silico Docking, Bioorg. Med. Chem. Lett., 2009, pp. 3756-375919, vol. 19, No. 14.
Le et al., Caspase activation and neuroprotection in caspase-3-deficient mice after in vivo cerebral ischemia and in vitro oxygen glucose deprivation, Proc. Natl. Acad. Sci, 2002, pp. 15188-15193, vol. 99, No. 23.
Lee et al., Intracellular retention of membrane-anchored v-sis protein abrogates autocrine signal-transduction, J. Cell. Biol., 1992, pp. 1057-1070, vol. 118, No. 5.
Li et al., Structural basis for inhibition of the epidermal growth factor receptor by cetuximab, Cancer Cell, 2005, vol. 7, pp. 301-311.
Lipinski, Drug-like properties and the causes of poor solubility and poor permeability, J. Pharm. Tox. Methods, 2000, pp. 235-249, vol. 44.
Lokeshwar et al., Protamine Enhances Epidermal Growth Factor (EGF)-stimulated Mitogenesis by Increasing Cell Surface EGF Receptor Number, J. Biol. Chem., 1989, 19318-19326, vol. 264, No. 32.

(56) References Cited

OTHER PUBLICATIONS

Lu et al., Discovery of a Nanomolar Inhibitor of the Human Murine Double Minute 2 (MDM2)-p53 Interaction through an Integrated, Virtual Database Screening Strategy, J. Med. Chem., 2006, pp. 3759-3762, vol. 49.
Ma et al., A Small-Molecule E2F Inhibitor Blocks Growth in a Melanoma Culture Model, Cancer Res, 2008, pp. 6292-6299, vol. 68, No. 15, CAS abstract, 1 page.
Magesh et al., Ocimum sanctum Induces Apoptosis in A549 Lung Cancer Cells and Suppresses the In Vivo Growth of Lewis Lung Carcinoma Cells, 2009, Phytother. Res., 2009, pp. 1385-1391, vol. 23.
Mexican Office Action Summary in English in related Mexican Application MX/a/2012/007872 dated Mar. 18, 2014, 5 pages.
Mexican Office Action in related Mexican Application MX/a/2012/007872 dated Mar. 18, 2014 in English and Spanish, 4 pages.
Modjtahedi et al., Phase I trial and tumour localisation of the anti-EGFR monoclonal antibody ICR62 in head and neck or lung cancer, Br. J. Cancer, 1996, pp. 228-235, vol. 73.
Mooney et al., Apoptotic mechanisms in T47D and MCF-7 human breast cancer cells, Br. J. Cancer, 2002, pp. 909-917, vol. 87.
Moy et al., High-Throughput Screen for Novel Antimicrobials Using a Whole Animal Infection Model, ACS Chem Bio., pp. 527-533, 2009, vol. 4, No. 7, CAS abstract, 2 pages.
Mukku, Regulation of Epidermal Growth Factor Receptor Levels by Thyroid Hormone*, J. Biol. Chem., 1984, pp. 6543-6546, vol. 259, No. 10.
Naumov et al., Combined Vascular Endothelial Growth Factor Receptor and Epidermal Growth Factor Receptor (EGFR) Blockade Inhibits Tumor Growth in Xenograft Models of EGFR Inhibitor Resistance, Clin. Cancer Res., 2009, pp. 3484-3494, vol. 15, No. 10.
Nicholson et al., Caspases: killer proteases, Trends Biochem. Sci., 1997, pp. 299-306, vol. 22.
Oehm et al., Purification and Molecular Cloning of the APO-1 Cell Surface Antigen, a Member of the Tumor Necrosis Factor/Nerve Growth Factor Receptor Superfamily, J. Biol. Chem., 1992, pp. 10709-10715, vol. 267, No. 15.
Olive, Quantitative methods for the analysis of protein phosphorylation in drug development, Expert Rev. Proteomics, 2004, pp. 327-341, vol. 1, No. 3.
Phillips et al., The Reaction of Anils with 8-Quinolinol, J Org Chem., 1954, pp. 907-909, vol. 19, CAS abstract, 2 pages.
Phillips et al., The Betti Reaction, Trans Kent Acad Sci., 1964, pp. 95-100, vol. 24, No. 3-4, CAS abstract, 1 page.
Preaudat et al. J. Biomol. Screening, a Homogeneous Caspase-3 Activity Assay Using HTRF Technology, 2002, pp. 267-274, vol. 7, No. 3.
Reddy et al., Novel Coumarin-3-(N-aryl)carboxamides arrest breast cancer cell growth by inhibiting ErbB-2 and ERK1, Bioorganic and Medicinal Chemistry Letters, 2005, pp. 3141-3147, vol. 13.
Roxas-Duncan et al., Identification and Biochemical Characterization of Small-Molecule Inhibitors of Clostridium botulinum Neurotoxin Serotype A, Antimicrobial Agents and Chemotherapy, 2009, pp. 3478-3486, vol. 53, No. 8.
Sanderson, The Mechanism of Lymphocyte-Mediated Cytotoxicity, Biol. Rev., 1981, 153-197, vol. 56.
Scanlon et al., Cytolysis by tumor necrosis factor is preceded by a rapid and specific dissolution of microfilaments, Proc. Natl. Acad. Sci. USA, 1989, pp. 182-186, vol. 86.
Schlegel et al., CPP32/Apopain Is a Key Interleukin 1β Converting Enzyme-like Protease Involved in Fas-mediated Apoptosis*, J. Biol. Chem., 1996, pp. 1841-1844, vol. 271, No. 4.
Sen et al., Reaction of Aldehydes and Amines with 8-Hydroxyquinaldine and 8-Quinolinol. II, J. Indian Chem. Soc., 1960, pp. 640-642, vol. 37, CAS abstract, 1 page.
Sergiev et al., Plant Growth Regulating Activity of Some Novel N-(6-methylpyrid-2-yl)-alpha-(8-hydroxy-quinolin-7-yl)-substituted benzylamines, Dokladi Na Bulgarskata Akademiya Na Naukite, 1998, pp. 67-70, vol. 51, No. 5-6, CAS abstract, 6 pages.
Shikhaliev et al., 2-Quinazolylguanidines in Heterocyclization Reactions. 3. Synthesis of 2-[(6-R-4-Methyl-2-quinazolyl)amino]pyrimidine-(1H)-ones, Chem. Het. Compounds, 2002, pp. 1368-1370, vol. 38, No. 11.
Slamon et al., Studies of the HER-2-neu proto-oncogene in human breast and ovarian cancer, Science, 1989, pp. 707-712, vol. 244.
Sporn et al., Proliferative Diseases, AM J Medicine, 1981, pp. 1231-1236, vol. 70, No. 6, 1 page abstract.
Stach et al., Biological Activity of the β Nerve Growth Factor: The Effects of Various Added Proteins, J. Neurochem., 1979, pp. 257-261, vol. 33.
Studier, Protein production by auto-induction in high-density shaking cultures, Protein Expr. Purif., 2005, pp. 207-234, vol. 41, No. 1.
Tang et al., Synergistic effect of triptolide combined with 5-fluorouracil on colon carcinoma, Postgrad. Med. J., 2007, pp. 338-343, vol. 83.
Tang et al., Dual MET-EGFR combinatorial inhibition against T790M-EGFR-mediated erlotinib-resistant lung cancer, Br. J. Cancer, 2008, pp. 911-922, vol. 99.
Teague et al., The design of leadlike combinatorial libraries, Angewandte Chemie Int. Ed., 1999, pp. 3743-3748, vol. 38, No. 24.
Telford et al., Comparative Evaluation of Several DNA Binding Dyes in the Detection of Apoptosis-Associated Chromatin Degradation by Flow Cytometry, Cytometry, 1992, pp. 137-143, vol. 13.
Thornberry et al., A Combinatorial Approach Defines Specificities of Members of the Caspase Family and Granzyme B, J. Biol. Chem., 1997, pp. 17907-17911, vol. 272, No. 29.
Thornberry et al., Caspases: Enemies Within, Science, 1998, pp. 1312-1316, vol. 281.
Tomlinson et al., A chemical genomic approach identifies matrix metalloproteinases as playing an essential and specific role in xenopus melanophore migration, Chemistry & Biology, 2009, pp. 93-104, vol. 16.
Torp et al., Expression of the epidermal growth factor receptor gene in human brain metastases, APMIS, 1992, pp. 713-719, vol. 100.
Trauth et al., Monoclonal Antibody-Mediated Tumor Regression by Induction of Apoptosis, Science, 1989, pp. 301-305, vol. 245.
Tuzi et al., Expression of growth factor receptors in human brain tumours, Br. J. Cancer, 1991, pp. 227-233, vol. 63.
Vassilev, p53 Activation by Small Molecules: Application in Oncology, J. Med. Chem. 2005, pp. 4491-4499, vol. 48, No. 14.
Vassilev, MDM2 inhibitors for cancer therapy, Trends in Molecular Medicine, 2006, pp. 23-31, vol. 13, No. 1.
Vermes et al., A novel assay for apoptosis Flow cytometric detection of phosphatidylserine expression on early apoptotic cells using fluorescein labelled Annexin V, J. Immun. Meth., 1995, pp. 39-51, vol. 184.
Webb et al., Quinazolines As Adenosine Receptor Antagonists: SAR and Selectivity for A2B Receptors, 2003, pp. 77-85, Bioorg. Med. Chem. vol. 11, No. 1.
Weis et al., Cellular Events in Fas/APO-1-Mediated Apoptosis in Jurkat T Lymphocytes, Exp. Cell Res., 1995, pp. 699-708, vol. 219.
Written Opinion in related PCT Application No. PCT/US11/20418 dated Jul. 7, 2011, 5 pages.
Wyllie et al., Cell Death: The Significance of Apoptosis, Int. Rev. of Cytol., 1980, pp. 251-306, vol. 68.
Yamada et al., Radiation-induced interphase death of rat thymocytes is internally programmed (apoptosis), Int. J. Radiat. Biol., 1988, pp. 65-75, vol. 53, No. 1.
Yonehara et al., A Cell-Killing Monoclonal Antibody (Anti-Fas) to a Cell Surface Antigen Co-Downregulated with the Receptor of Tumor Necrosis Factor, J. Exp. Med., 1989, pp. 1747-1756, vol. 169.
Zhang et al., A Simple Statistical Parameter for Use in Evaluation and Validation of High Throughput Screening Assays, J. Biomol. Screening, 1999, pp. 67-73, vol. 4.
Zhang et al., Apoptosis of human colon carcinoma HT-29 cells induced by Ceramide, 2006, Worl. J. Gastroenterol., pp. 3581-3584, vol. 12, No. 22.

COMBINATION THERAPY WITH MDM2 AND EFGR INHIBITORS

CROSS-REFERENCE TO RELATED APPLICATIONS

The present application is a Divisional of U.S. Nonprovisional application Ser. No. 13/188,351 filed 21 Jul. 2011, which is a Continuation in Part of U.S. Nonprovisional application Ser. No. 12/986,146 filed 6 Jan. 2011, now U.S. Pat. No. 8,618,302 issued 31 Dec. 2013, which claims the benefit of U.S. Provisional Application Ser. No. 61/292,776 filed 6 Jan. 2010; the present application also is a Continuation in Part of International Application No. PCT/US11/20414 filed 6 Jan. 2011 and International Application No. PCT/US11/20418 filed 6 Jan. 2011; the present application also claims the benefit of U.S. Provisional Application Ser. No. 61/366,480 filed 21 Jul. 2010, all of which are incorporated herein by reference in their entireties.

FIELD OF THE INVENTION

The present invention generally relates to development of new chemical entities for use in the treatment of disease, and more particularly to methods of identifying lead molecules for use in quasi-rational drug design.

BACKGROUND OF THE INVENTION

Tumor protein 53 (P53) is a tumor suppressing protein that regulates the cell cycle, suppresses tumors, and thereby prevents cancer. Murine double minute 2 (MDM2) is an important negative regulator of p53 and inhibitor of p53 transcriptional activation (see Vassilev 2006 Trends in Molecular Medicine 13(1), 23-31). MDM2 binds and inactivates p53 by directly blocking the p53 transactication domain and by serving as an E3 ubiquitin ligase for p53, thereby targeting p53 protein for ubiquitin-dependent degradation in the proteasome. About 11 million cancer patients have an inactivating mutation in the p53 protein.

EGFR is involved in the same cellular signaling pathway as MDM2. EGFR is a known cancer-associated molecule and EGFR inhibitors, such as Tarceva, provide targeted cancer treatment. Significant numbers of cancer patients become resistant to treatment with approved EGFR inhibitors, such as Tarceva. There is currently no approach to overcome such resistance.

SUMMARY OF THE INVENTION

Disclosed herein are small molecule MDM2 inhibitor compounds useful for cancer treatment alone or in synergistic combination with an inhibitor of Epidermal Growth Factor Receptor (EGFR).

An MDM2 inhibitor used in combination with an EGFR inhibitor, such as Tarceva, can provide treatment for patients with developed resistance. Combinatorial treatment with an MDM2 inhibitor and an EGFR inhibitor, such as Tarceva, can have synergistic anti-cancer effects and can overcome developed resistance.

One aspect provides a method of treating a proliferative disease, disorder, or condition. The method of combinatorial treatment can include administering to an MDM2 inhibitor and an EGFR inhibitor to a subject. The subject can be in need of such treatment. The amount of the MDM2 inhibitor and the EGFR inhibitor can be an amount sufficient to produce a therapeutic effect.

In some embodiments, the proliferative disease, disorder, or condition includes cancer. In some embodiments, administering the MDM2 inhibitor and the EGFR inhibitor results in a synergistic reduction in cell proliferation in a tumor of the subject or a synergistic increase in apoptosis in a tumor of the subject as compared to administration of either the MDM2 inhibitor or the EGFR inhibitor alone.

In some embodiments, a pharmaceutical composition comprising an MDM2 inhibitor, an EGFR inhibitor, and a pharmaceutically acceptable carrier or excipient is administered to the subject. In some embodiments, a first pharmaceutical composition comprising an MDM2 inhibitor and a pharmaceutically acceptable carrier or excipient and a second pharmaceutical composition comprising an EGFR inhibitor and a pharmaceutically acceptable carrier or excipient is administered to the subject.

In some embodiments, the subject has one or more of (i) an inactivating P53 mutation or deletion in the subject; (ii) a defect in an upstream component of a p53 pathway; (iii) a defect in a downstream component of the p53 pathway; (iv) increased expression an MDM2 gene as compared to a control; (v) increased levels of MDM2 protein as compared to a control; or (vi) resistance to treatment with an EGFR inhibitor alone. In some embodiments, the method includes selecting or modifying a treatment on the basis of detecting in a subject one or more of (i) an inactivating P53 mutation or deletion in the subject; (ii) a defect in an upstream component of a p53 pathway; (iii) a defect in a downstream component of the p53 pathway; (iv) increased expression an MDM2 gene as compared to a control; (v) increased levels of MDM2 protein as compared to a control; or (vi) resistance to treatment with an EGFR inhibitor alone.

In some embodiments, the EGFR inhibitor is selected from the group consisting of cetuximab, panitumumab, nimotuzumab, zalutumumab, matuzumab, potato carboxypeptidase inhibitor, gefitinib, lapatinib, and erlotinib, or a combination thereof. In some embodiments, the EGFR inhibitor is erlotinib (tradename Tarceva).

In some embodiments, the MDM2 inhibitor (i) inhibits MDM2 activity; (ii) increases phosphorylated p53; (iii) re-activates p53; (iv) inhibits binding of p53 and MDM2; or a combination thereof. In some embodiments, the MDM2 inhibitor inhibits binding of p53 and MDM2.

In some embodiments, the MDM2 inhibitor comprises a compound of Formula (2) as defined herein. In some embodiments, the MDM2 inhibitor comprises a compound of Formula (10) as defined herein. In some embodiments, the MDM2 inhibitor comprises a compound of Formula (11) as defined herein.

Another aspect provides a pharmaceutical composition including an MDM2 inhibitor; an EGFR inhibitor, and a pharmaceutically acceptable carrier or excipient.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
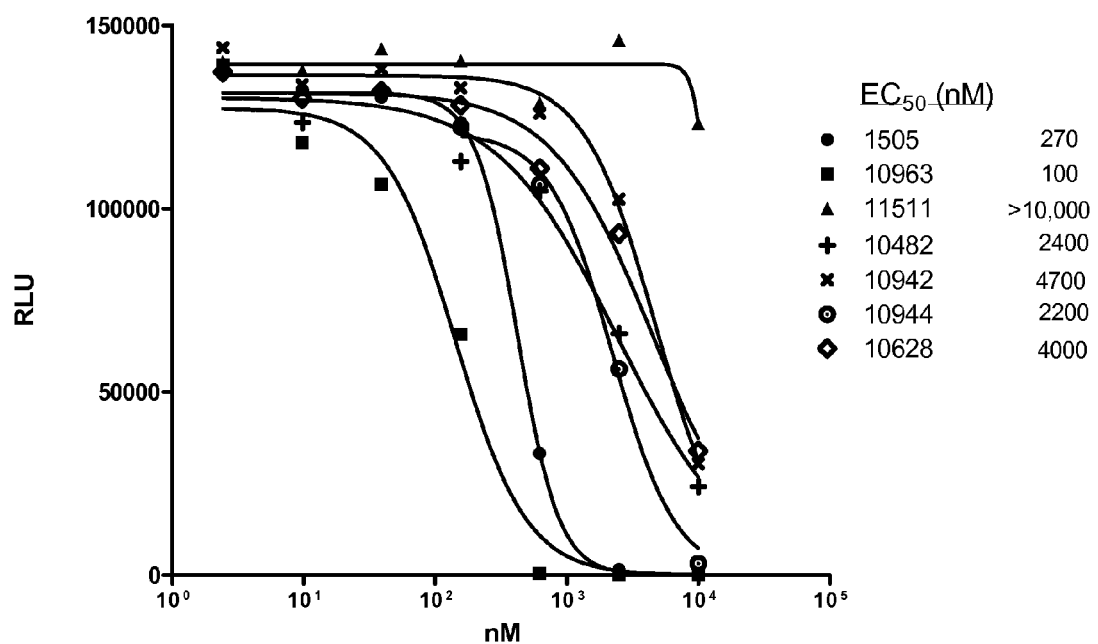
FIG. 1 is a line and scatter plot showing inhibition of p53/MDM2 binding. RLU is shown as a function of nm, with $EC_{50}$ determined for each of AD4-1505, AD4-10963, AD4-11511, AD4-10482, AD4-10942, AD4-10944, and AD4-10628.
Figure 2:
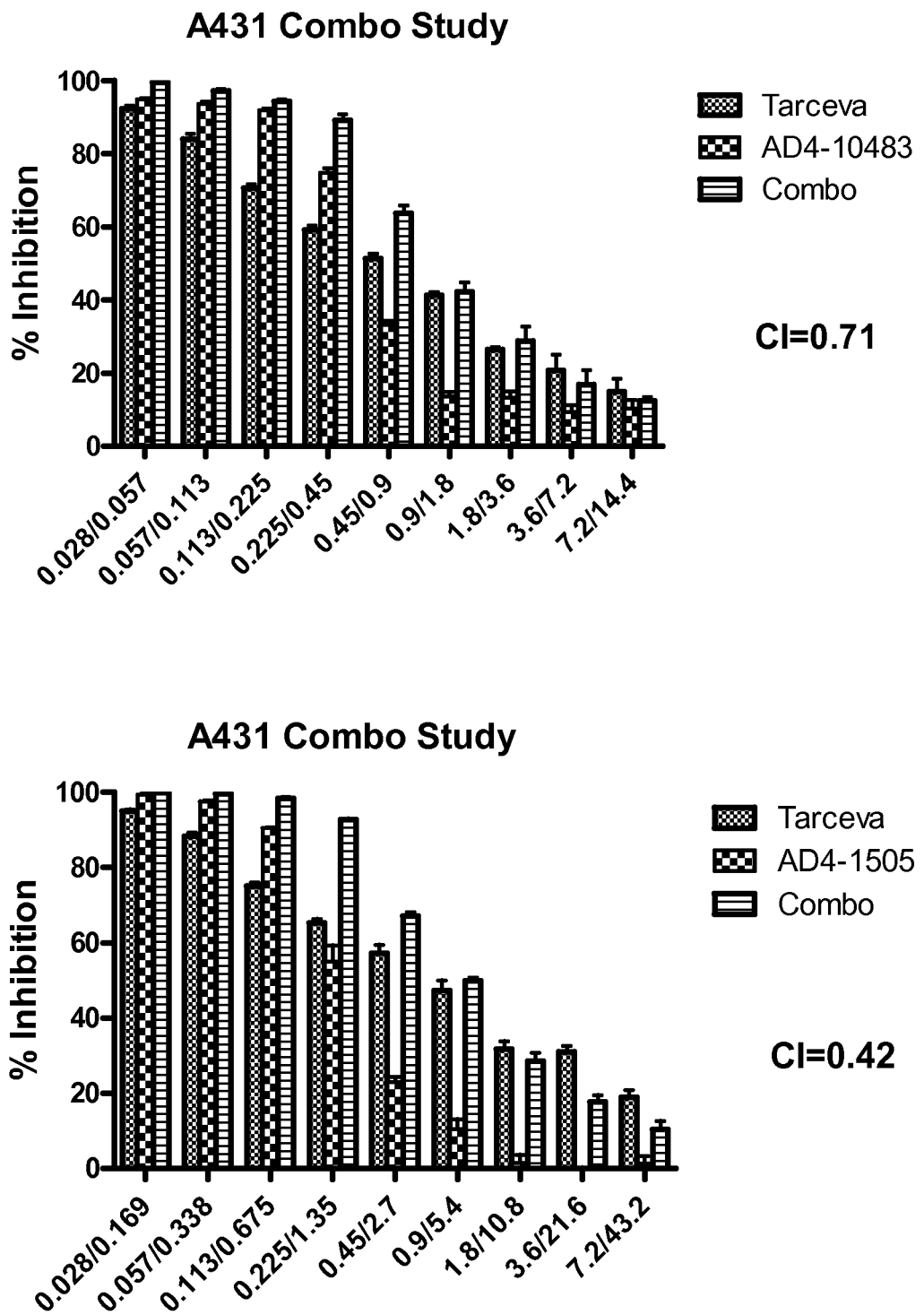
FIG. 2 is a series of bar graphs showing percent inhibition of proliferation in A431 cells resulting from a combination of Tarceva and each of compounds AD4-10483, AD4-1505, AD4-10963, and AD4-10628-2. CI, an indication of synergy when less than 0.8, was determined for each combination.
Figure 2:
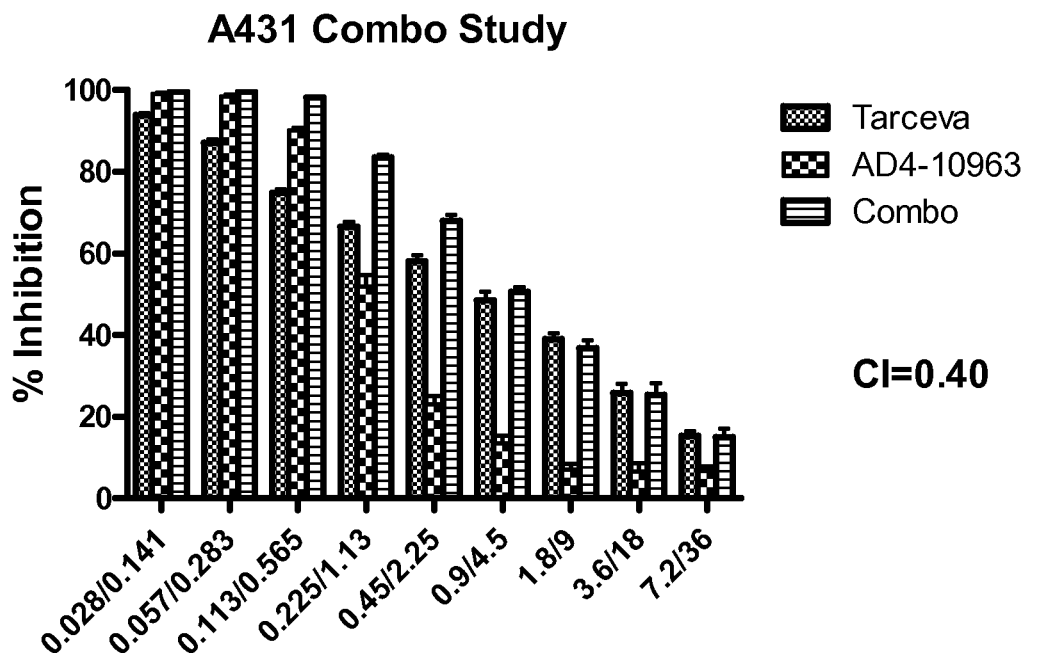
Figure 2:
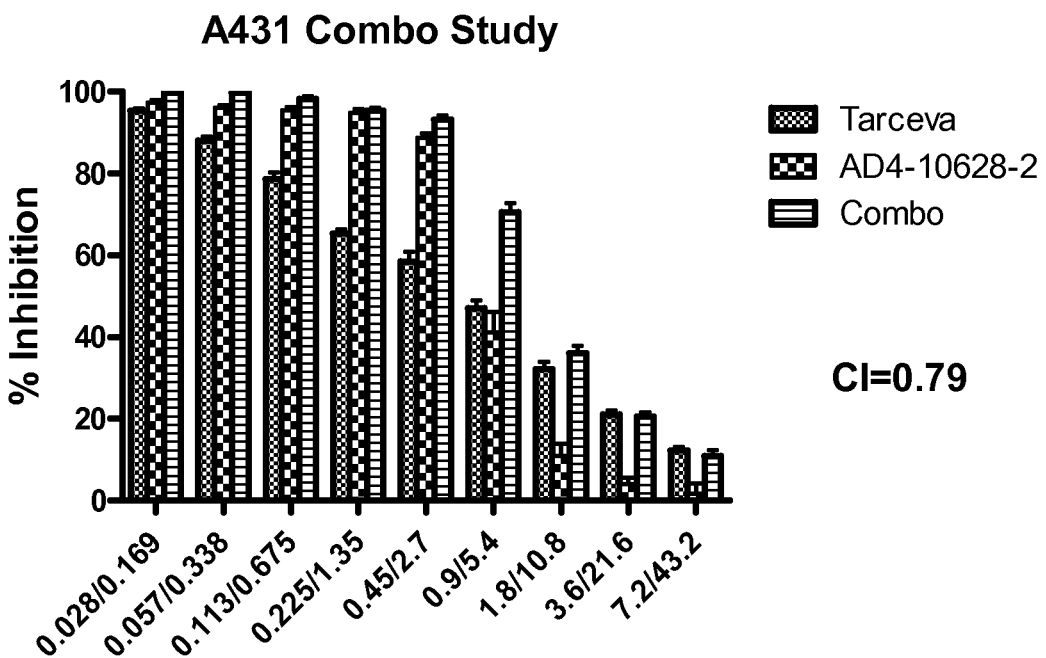

The present disclosure is based, at least in part, on the discovery that combinatorial administration of a compound that inhibits binding of p53 and MDM2 along with an EGFR inhibitor (e.g., Tarceva) can provide synergistic anti-cancer effects and can overcomes developed resistance. A compounds ability to inhibit binding of p53 and MDM2 can be an indicator of synergistic anti-cancer effect when in combination with an EGFR inhibitor, especially in a subject with or at risk for resistance to such EGFR inhibitor.

U.S. application Ser. No. 11/626,324, published as US Application Publication No. 2008/0015194, is hereby incorporated by reference in its entirety. U.S. application Ser. No. 12/986,146 is hereby incorporated by reference in its entirety. PCT/US2011/020414, published as WO 2011/085126, is hereby incorporated by reference in its entirety. PCT/US2011/020418, published as WO 2011/085129, is hereby incorporated by reference in its entirety.

A second target in cancer treatment is EGFR, a protein frequently dysregulated in cancer cells. Overexpression of EGFR is known to be associated with cancers of many tissues. Approved EGFR inhibitors, such as Tarceva, provide anti-cancer effects but patients can develop resistance.

oEGFR stimulates several cellular pathways, including the ras/raf pathway which leads to the subsequent stimulation of MEK and ERK interaction with p53-MDM2 complex.

Further, as described herein, combinatorial administration of a compound that inhibits p53 binding to MDM2 and an EGFR inhibitor (e.g., Tarceva) can provide synergistic anti-cancer effects and can overcome developed resistance. Further, administration of MDM2 inhibitors in combination with an EGFR inhibitor, such as Tarceva, can result in synergistic tumor reduction and can overcome resistance to the EGFR inhibitor. The EGFR and p53/MDM2 signaling are interconnected through the interaction of ERK and MDM2. Provided herein are methods and materials to identify novel small molecule drug candidates that inhibit MDM2-p53 binding and demonstrate synergystic anti-cancer effects with EGFR kinase inhibitors (e.g., approved EGFR kinase inhibitors).

Working examples provided herein show at least the following. A compound with the ability to inhibit p53/MDM2 binding can: (a) inhibit cell proliferation in the A431 cell line that over-expresses the EGF receptor; (b) produce a synergistic effect with Tarceva, an EGFR kinase inhibitor, in a cell proliferation assay in the A431 cell line; (c) induce apoptosis in the A431 cell line as measured by an increase in caspase activity, to a similar extent as Tarceva; (d) produce a synergistic effect with Tarceva in an apoptosis assay in the A431 cell line; (e) increases apoptosis in the A549 cell line, as measured by increased DNA fragmentation; (f) produce a synergistic effect with Tarceva in an apoptosis assay in the A431 cell line; or (g) increase phosphorylated p53; or a combination thereof. Examples 1-7 describe assays used in further examples. Examples 8-9 show compounds inhibit EFG-mediated cell proliferation and have a synergistic effect with Tarceva. Examples 10-13 show compounds inhibit interaction of p53 and MDM2. Example 14 shows correlation of p53 inhibition and synergistic cell proliferation. Examples 15-18 show compounds induce apoptosis (as measured by DNA fragmentation assay and caspase assay). Example 17 shows compounds increase phosphorylated p53 compounds.

Inhibitor of P53/MDM2 Binding

The present disclosure provides several novel classes of compounds that inhibit MDM2, re-activate p53, or inhibit the binding of p53 and MDM2. A pharmacophore-based class of compounds that inhibits MDM2 and thereby re-activates p53 has been identified. Such compounds can be used alone as anti-cancer therapeutic agents, or in synergistic combination with therapeutic EGFR inhibitors, as described further herein. Also provided herein are in silico pharmacophore-based design, in vitro assays, and in vivo animal models to identify and optimize compounds that inhibit MDM2.

MDM2 is an inhibitor of activation of P53, which is a tumor suppressing protein that prevents cancer. Over-expression of MDM2 can cause inactivation of tumor suppressor p53, which can result in many types of cancer. A drug inhibiting MDM2 (e.g., inhibition of MDM2-p53 binding) can re-activate or restore the function of p53, resulting in tumor reduction and providing therapeutic approach for cancer treatment.

An MDM2 inhibitor, as that term is used herein, can refer to anyone of, or a combination of, MDM2 activity inhibition, increase of phosphorylated p53, re-activation of p53, or inhibition of the binding of p53 and MDM2. An MDM2 inhibitor can inhibit the activity of MDM2. An MDM2 inhibitor can increase of phosphorylated p53. An MDM2 inhibitor can re-activate p53. An MDM2 inhibitor can inhibit p53/MDM2 binding. Increase of a phosphorylated form of p53 can decrease binding of p53 and MDM2.

An MDM2 inhibitor compound can be identified through one or more of the following: (a) ability to inhibit cell proliferation in the A431 cell line that over-expresses the EGF receptor; (b) ability to produce a synergistic effect with Tarceva, an EGFR kinase inhibitor, in a cell proliferation assay in the A431 cell line; (c) ability to induce apoptosis in the A431 cell line as measured by an increase in caspase activity; (d) ability to produce a synergistic effect with Tarceva in an apoptosis assay in the A431 cell line; (e) ability to increases apoptosis in the A549 cell line, as measured by increased DNA fragmentation; (f) ability to induce apoptosis in the A431 cell line to a similar extent as Tarceva; and (g) ability to increase phosphorylated p53. Guidance as to pertinent assays for demonstration of the above are provided in Examples 1-7. Exemplary results using such assays to assess candidate compounds are provided in: Examples 8-9 (inhibition of EFG-mediated cell proliferation and synergy with EGFR inhibitor); Examples 10-13 (inhibition of interaction of p53 and MDM2); Example 14 (correlation of p53 inhibition and synergistic cell proliferation); Examples 15-18 (induction of apoptosis as measured by DNA fragmentation assay and caspase assay); and Example 17 (increased phosphorylated p53).

One of ordinary skill will understand that any compound demonstrating activity as described above can be used in the combinatorial therapeutic approach described herein. Exemplary MDM2 inhibitor compounds are further discussed below.

An MDM2 inhibitor can be a compound as disclosed in U.S. application Ser. No. 11/626,324, published as US Application Publication No. 2008/0015194; U.S. Nonprovisional application Ser. No. 12/986,146; International Application No. PCT/US11/20414, published as WO 2011/085126; or International Application No. PCT/US11/20418, published as WO 2011/085129; each of which is incorporated herein by reference.

An MDM2 inhibitor can be a compound as disclosed in Vassilev 2006 Trends in Molecular Medicine 13(1), 23-31. For example, an MDM2 inhibitor can be a nutlin (e.g., a cis-imidazole compound, such as nutlin-3a); a benzodiazepine as disclosed in Grasberger et al. 2005 J Med Chem 48, 909-912; a RITA compound as disclosed in Issaeva et al. 2004 Nat Med 10, 1321-1328; a spiro-oxindole compound as disclosed in Ding et al. 2005 J Am Chem Soc 127, 10130-10131 and Ding et al. 2006 J Med Chem 49, 3432-3435; or a quininol compound as disclosed in Lu et al. 2006 J Med Chem 49, 3759-3762. As a further example, an MDM2 inhibitor can be a compound as disclosed in Chene 2003 Nat. Rev. Cancer 3, 102-109; Fotouhi and Graves 2005 Curr Top Med Chem 5, 159-165; or Vassilev 2005 J Med Chem 48, 4491-4499.

Type A AD4-1505-like compounds.

An MDM2 inhibitor can be a compound according to Formula 2 (a Type A AD4-1505-like compound) as follows:

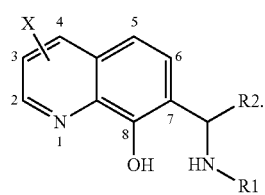

Formula (2)

In the above structure, $X^1$ of Formula (2) can represent one or more functional group from the following Hydrogen atom, 2-Methyl, 5-Chloro, 5-Nitro, or 6-Hydroxyl group.

$R^1$ of Formula (2) can represent:

a 2-Pyridyl ring of Formula (3) wherein $R^{23}$ is selected from the group consisting of hydrogen; fluoro; chloro; trifluoromethyl; methyl; ethyl; and methoxy; $R^3$ is selected from the group consisting of hydrogen; fluoro; chloro; methyl; ethyl; methoxy; a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; $R^{24}$ is selected from the group consisting of: hydrogen; fluoro; chloro; and trifluoromethyl; and $R^4$ is selected from the group consisting of hydrogen; methyl; a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom;

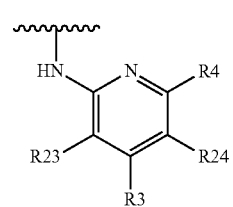

Formula (3)

a 3-Pyridyl ring of Formula (4) wherein $R^5$, $R^6$, and $R^7$ are independently selected from the group consisting of: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group in the above definition) (e.g., AD4-12908, AD4-13051, AD4-13021, AD4-13021, AD4-13063, AD4-013064, AD4-13065, AD4-13066, AD4-13101);

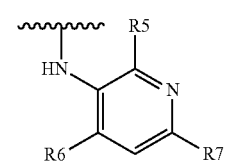

Formula (4)

a 4-Pyridyl ring of Formula (5) wherein $R^8$ and $R^9$ are independently selected from the group consisting of: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group in the above definition);

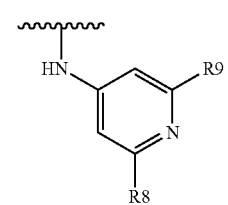

Formula (5)

an unsubstituted phenyl ring or, preferably, a phenyl ring substituted with one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, alkoxy (—$OR^{10}$ where $R^{10}$ is defined as a lower alkyl group or cycloalkyl group as in the above definition), trifluoromethyl, trifluoromethoxy, difluoromethoxy, 3,4-methylenedioxy, 2,3-methylenedioxy, Nitro or Halogen (F, Cl, Br, I); or an unsubstituted heteroaryl five or six membered ring containing from 1 to 4 N, O, or S atoms, or a heteroaryl five or six membered ring containing from 1 to 4 N, O, or S atoms which has one or more optional substitution with the substituent defined as one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl five or six membered ring containing from 1 to 4 N, O, or S atoms, Alkoxy (—$OR^{10}$ where $R^{10}$ is defined as a lower alkyl group or cycloalkyl group in the above definition).

It has been found that where $R^1$ is a 2-pyridyl ring of Formula (3) and $R^{24}$ is chloro or $R^{23}$ is methyl, the resulting compound can exhibit increased stability.

It has been found that where $R^1$ is a 2-pyridyl ring of Formula (3) having combinations of substituted halogens and alkyl groups, the resulting compound can exhibit increased antiproliferative activity. For example, where $R^1$ is a 2-pyridyl ring of Formula (3), the following substitutions can provide increased antiproliferative activity: $R^4$ is hydrogen, $R^{24}$ is fluoro, $R^3$ is hydrogen, and $R^{23}$ is fluoro; $R^4$ is methyl, $R^{24}$ is chloro, $R^3$ is hydrogen, and $R^{23}$ is fluoro; $R^4$ is hydrogen, $R^{24}$ is chloro, $R^3$ is ethyl, and $R^{23}$ is fluoro; $R^4$ is hydrogen, $R^{24}$ is fluoro, $R^3$ is methyl, and $R^{23}$ is fluoro; $R^4$ is hydrogen, $R^{24}$ is chloro, $R^3$ is hydrogen, and $R^{23}$ is ethyl; $R^4$ is methyl, $R^{24}$ is chloro, $R^3$ is hydrogen, and $R^{23}$ is chloro; $R^4$ is hydrogen, $R^{24}$ is chloro, $R^3$ is methyl, and $R^{23}$ is fluoro; $R^4$ is hydrogen, $R^{24}$ is trifluoromethyl, $R^3$ is hydrogen, and $R^{23}$ is hydrogen; $R^4$ is hydrogen, $R^{24}$ is chloro, $R^3$ is hydrogen, and $R^{23}$ is methyl; $R^4$ is hydrogen, $R^{24}$ is chloro, $R^3$ is hydrogen, and $R^{23}$ is chloro; $R^4$ is hydrogen, $R^{24}$ is chloro, $R^3$ is methyl, and $R^{23}$ is hydrogen; or $R^4$ is hydrogen, $R^{24}$ is chloro, $R^3$ is chloro, and $R^{23}$ is hydrogen.

It has been found that where $R^1$ is a 2-pyridyl ring of Formula (3) and $R^{24}$ is chloro and there is additionally a chloro or methyl at one or both of $R^3$ or $R^{23}$, the resulting compound can exhibit increased apoptosis. For example, where $R^1$ is a 2-pyridyl ring of Formula (3), the following substitutions can provide increased apoptosis: $R^{24}$ is chloro, $R^3$ is hydrogen, and $R^{23}$ is methyl; $R^{24}$ is chloro, $R^3$ is methyl, and $R^{23}$ is fluoro; $R^{24}$ is chloro, $R^3$ is chloro, and $R^{23}$ is hydrogen; and $R^{24}$ is chloro, $R^3$ is hydrogen, and $R^{23}$ is chloro.

It has been found that, where $R^1$ of Formula (2) is a 2-Pyridyl ring of Formula (3), the group at $R^{24}$ of the aminopyridine can block metabolism in cultured hepatocytes.

As preferred examples, $R^1$ of Formula (2) can represent: an unsubstituted 2-(1,3-thiazoyl) ring (see Formula (6)) or a 2-(1,3-thiazoyl) ring with groups at the 4- or 5-position of the thiazole ring, for example a 2-(4,5-Dimethyl-1,3-thiazoyl) ring (see Formula (7)):

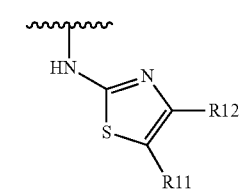

2-(1,3-THIAZOYL) RING SUBSTITUTION

Formula (6)

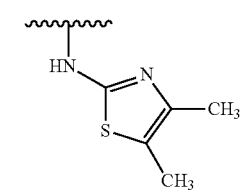

2-(4,5-DIMETHYL-1,3-THIAZOYL) GROUP

Formula (7)

$R^2$ of Formula (2) can represent:

an unsubstituted Phenyl ring or a Phenyl ring substituted at the 2-, 3-, 4-, 5- or 6-position with one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group as in the above definition), 2,3-Methylenedioxy or 3,4-Methylenedioxy group, Dialkylamino (—$NR_{13}R_{14}$ where $R_{13}$ and $R_{14}$ are independently selected from a Hydrogen atom or lower alkyl group as previously described); Trifluoromethyl, Trifluoromethoxy, Difluoromethyl, 3,4-methylenedioxy, 2,3-methylenedioxy, Nitro or Halogen (F, Cl, Br, I);

a 2-Thiophene ring of Formula (8) wherein $R^{15}$, $R^{16}$, and $R^{17}$ are independently selected from the group consisting of: hydrogen, lower alkyl, cycloalkyl, Alkoxy, Dialkylamino, Trifluoromethyl, Difluoromethyl, Trifluoromethoxy or halogen as described above;

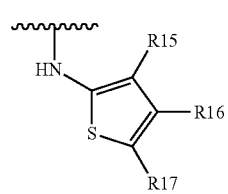

2-THIOPHENE RING SUBSTITUTION

Formula (8)

a 3-Thiophene ring of Formula (9) wherein $R^{18}$, $R^{19}$, and $R^{20}$ are independently selected from the group consisting of: lower alkyl, cycloalkyl, Alkoxy, Dialkylamino, Trifluoromethyl, Difluoromethyl, Trifluoromethoxy or halogen as described above;

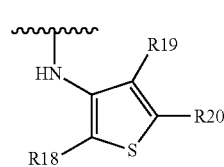

3-THIOPHENE RING SUBSTITUTION

Formula (9)

an unsubstituted 2-Pyridyl ring or a 2-Pyridyl ring substituted at the 4- or 6-position of the pyridine ring with one or more of the following groups: lower alkyl group as defined above, cycloalkyl group as defined above;

an unsubstituted 3-Pyridyl ring or a 3-Pyridyl ring substituted at the 2-, 4- or 6-position of the pyridine ring with one or more of the following groups: lower alkyl group as defined above, cycloalkyl group as defined above; or an unsubstituted 4-Pyridyl ring or a 4-Pyridyl ring substituted at the 2- or 6-position of the pyridine ring with one or more of the following groups: lower alkyl group as defined above, cycloalkyl group as defined above.

It has been found that where $R^2$ is a phenyl ring substituted at the 2- and 4-positions, the resulting compound can exhibit increased stability. For example, where $R^2$ is 4-trifluoromethylphenyl; 2-fluoro,4-trifluoromethylphenyl; or 2,4-dichlorophenyl, the resulting compound can exhibit increased stability.

It has been found that where R² is a phenyl ring substituted with a combination of halogens and trifluoromethyl groups, the resulting compound can exhibit increased antiproliferative activity. For example, where R² is 4-chlorophenyl; 2-fluoro,4-trifluoromethylphenyl; 3-fluoro,4-chlorophenyl; 2-fluoro,4-chlorophenyl; 2,3-dichlorophenyl; 2,3,5-trichlorophenyl; 2,4-dichlorophenyl; 3,4-dichlorophenyl; or 3,5-dichlorophenyl, the resulting compound can exhibit increased antiproliferative activity.

It has been found that where R² is a phenyl ring substituted at the 4 position with chloro and additionally substituted at the 2- or 3-position with chloro or fluoro, the resulting compound exhibits increased apoptosis. For example, where R² is 2,4-dichlorophenyl or 2-chloro,4-fluorophenyl, the resulting compound can exhibits increased apoptosis.

In some embodiments, the compound(s) are the enantiomeric isomers of Formula (2).

In some embodiments, the compound(s) of Formula (2) are according to R¹ and R² as provided in the following TABLE 1, TABLE 2, TABLE 3, and TABLE 4.

TABLE 1

| R2 phenyl substitution | R1 = 5ClPyr | R1 = 5FPyr | R1 = 4ClPyr | R1 = 4Me—5ClPyr | R1 = 4Me—5FPyr |
|---|---|---|---|---|---|
| 2Cl | AD4-13087 | AD4-13104 | | AD4-13141 | AD4-13116 |
| 3Cl | AD4-13151 | | | | |
| 4Cl | AD4-13152 | | | AD4-13157 | |
| 2,3-diCl | AD4-13086 | AD4-13103 | | AD4-13153 | AD4-13126 |
| 3,4-diCl | AD4-13054 | AD4-13113 | AD4-13069 | AD4-13166 | AD4-13127 |
| 2,4-diCl | AD4-13097 | AD4-13110 | | AD4-13123 | AD4-13128 |
| 2,5-diCl | AD4-13095 | AD4-13102 | | AD4-13158 | AD4-13118 |
| 3,5-diCl | AD4-13094 | AD4-13098 | | AD4-13122 | AD4-13114 |
| 2,6-diCl | AD4-13109 | AD4-13120 | | AD4-13148 | AD4-13125 |
| 2,3,5-triCl | AD4-13111 | AD4-13132 | | AD4-13156 | |
| 2Cl—4F | AD4-13088 | AD4-13099 | | AD4-13149 | AD4-13115 |
| 2Cl—6F | AD4-13091 | AD4-13112 | | AD4-13140 | AD4-13117 |
| 3F—4Cl | | | | | |
| 3Cl—4F | | | | | |
| 4CF3 | AD4-13053 | | AD4-13044 | AD4-13121 | |
| 3F—4CF3 | AD4-13055 | AD4-13061 | AD4-13048 | AD4-13106 | |
| 2Cl—5CF3 | AD4-13052 | AD4-13049 | AD4-13060 | | |
| 4Cl—5CF3 | AD4-13067 | AD4-13071 | AD4-13047 | AD4-13108 | |
| 2,4-diCF3 | | | | AD4-13124 | |
| 3CF3 | | | | AD4-13107 | |
| 2F—4CF3 | | | AD4-13046 | AD4-13129 | |
| 2,3,5,6-F4 | | AD4-13070 | | AD4-13136 | |
| 2,4-diF | | AD4-13050 | AD4-13045 | | |
| 3-Me-4-OMe | | | | | |
| 2-F | | | | | |
| 2,3,5,6-F4-4-OCH2CF3 | | | | | |
| 2-Me | | | | | |
| 3-F | | | | | |
| 4-OCF3 | | | | | |
| 3-OH-4-OMe | | | | AD4-13186 | |
| 2-OH-5-Me | | | | | |
| 3,4-diOMe | | | | AD4-13194 | |
| 2,3,4-triOMe | | | | AD4-13196 | |

TABLE 2

| R2 phenyl substitution | R1 = 3Me—5Cl | R1 = 5-CF3Pyr | R1 = Pyr | R1 = 4-MePyr | R1 = 6-MePyr | R1 = 3,5-diFPyr |
|---|---|---|---|---|---|---|
| 2Cl | AD4-13134 | | | AD4-12907 | AD4-12904 | AD4-13183 |
| 3Cl | AD4-13159 | | | | | AD4-13173 |
| 4Cl | AD4-13154 | | | | | AD4-13174 |
| 2,3-diCl | AD4-13147 | | AD4-10051 | AD4-12906 | AD4-12905 | |
| 3,4-diCl | AD4-13119 | AD4-13030 | AD4-13037 | AD4-12917 | AD4-12916 | AD4-13182 |
| 2,4-diCl | AD4-13130 | AD4-13033 | AD4-13039 | AD4-12912 | AD4-12911 | AD4-13175 |
| 2,5-diCl | AD4-13137 | | AD4-12910 | AD4-12954 | AD4-12955 | AD4-13155 |
| 3,5-diCl | AD4-13131 | | AD4-12914 | AD4-12915 | AD4-12913 | AD4-13176 |
| 2,6-diCl | AD4-13142 | | AD4-13019 | | | AD4-13138 |
| 2,3,5-triCl | AD4-13167 | | | AD4-13072 | AD4-13023 | AD4-13181 |
| 2Cl—4F | AD4-13139 | | AD4-13027 | AD4-13026 | AD4-13024 | AD4-13146 |
| 2Cl—6F | AD4-13135 | | | AD4-13020 | AD4-12959 | AD4-13133 |
| 3F—4Cl | AD4-13229 | | | | | |
| 3Cl—4F | | | | | | |
| 4CF3 | AD4-13041 | AD4-13028 | AD4-10460 | AD4-10486 | AD4-10628 | |
| 3F—4CF3 | AD4-13043 | AD4-13034 | AD4-13040 | | | |

TABLE 2-continued

R1 and R2 substitution combinations (Pyr = pyridine; Ani = aniline)

| R2 phenyl substitution | R1 = 3Me—5Cl | R1 = 5-CF3Pyr | R1 = Pyr | R1 = 4-MePyr | R1 = 6-MePyr | R1 = 3,5-diFPyr |
|---|---|---|---|---|---|---|
| 2Cl—5CF3 | AD4-13058 | AD4-13056 | AD4-13035 | | | |
| 4Cl—5CF3 | | AD4-13032 | AD4-13057 | | | |
| 2,4-diCF3 | | | | | | |
| 3CF3 | | AD4-13164 | | | AD4-12903 | |
| 2F—4CF3 | AD4-13042 | AD4-13031 | AD4-13038 | AD4-13096 | | |
| 2,3,5,6-F4 | AD4-13059 | | | | AD4-12918 | |
| 2,4-diF | AD4-13068 | AD4-13029 | AD4-13036 | | | |
| 3-Me-4-OMe | | | AD4-12965 | | | |
| 2-F | | | | | | |
| 2,3,5,6-F4-4-OCH2CF3 | | | AD4-13093 | AD4-13092 | AD4-13085 | |
| 2-Me | | | | AD4-12935 | | |
| 3-F | | | | AD4-12953 | | |
| 4-OCF3 | | | | | AD4-12902 | |
| 3-OH-4-OMe | AD4-13190 | | | AD4-1505 | AD4-12909 | |
| 2-OH-5-Me | | | | | AD4-12936 | |
| 3,4-diOMe | AD4-13193 | | | | | |
| 2,3,4-triOMe | AD4-13208 | | | | | |
| 2,4-diCl (2MeQ) | AD4-13200 | | | | | |

TABLE 3

R1 and R2 substitution combinations (Pyr = pyridine; Ani = aniline)

| R2 phenyl substitution | R1 = 3F—5ClPyr | R1 = 5-Cl-6-MePyr | R1 = 3-F-5-CF3Pyr | R1 = 4,5-diClPyr | R1 = 3-F-4-Me-5-ClPyr | R1 = 3,5-diCl-6-MePyr |
|---|---|---|---|---|---|---|
| 2Cl | | | | | | |
| 3Cl | | | | AD4-13188 | | |
| 4Cl | | AD4-13161 | | AD4-13187 | | |
| 2,3-diCl | | | | AD4-13172 | AD4-13192 | AD4-13211 |
| 3,4-diCl | AD4-13150 | | | AD4-13177 | | AD4-13202 |
| 2,4-diCl | AD4-13143 | | AD4-13165 | AD4-13178 | AD4-13199 | AD4-13206 |
| 2,5-diCl | | | | AD4-13179 | | AD4-13220 |
| 3,5-diCl | | | | AD4-13189 | | AD4-13223 |
| 2,6-diCl | | | | | | |
| 2,3,5-triCl | | AD4-13209 | | AD4-13180 | | AD4-13213 |
| 2Cl—4F | | | | AD4-13185 | | |
| 2Cl—6F | | | | | | |
| 3F—4Cl | | | | AD4-13224 | | AD4-13230 |
| 3Cl—4F | | | | | | |
| 4CF3 | AD4-13162 | | | | | |
| 3F—4CF3 | AD4-13144 | | | | | |
| 2Cl—5CF3 | | | | | | |
| 3CF3-4-Cl | | | | AD4-13184 | | |
| 2,4-diCF3 | | | | | | |
| 3CF3 | AD4-13145 | | | | | |
| 2F—4CF3 | | | | | | |
| 2,3,5,6-F4 | AD4-13163 | | | | | |
| 2,4-diF | | | | | | |
| 3-Me-4-OMe | | | | | | |
| 2-F | | | | | | |
| 2,3,5,6-F4-4-OCH2CF3 | | | | | | |
| 2-Me | | | | | | |
| 3-F | | | | | | |
| 4-OCF3 | | | | | | |
| 3-OH-4-OMe | | | | AD4-13191 | AD4-13203 | |
| 2-OH-5-Me | | | | | | |
| 3,4-diOMe | | | | AD4-13195 | | |
| 2,3,4-triOMe | | | | AD4-13197 | | AD4-13210 |

TABLE 4

R1 and R2 substitution combinations (Pyr = pyridine; Ani = aniline)

| R2 phenyl substitution | R1 = 2-Me-4-Cl-Ani | R1 = 3-Me-4-Cl-Ani | R1 = 3-MeO-5-ClPyr | R1 = 3-Et-5-ClPyr | R1 = 3-F-4-Et-5-ClPyr | R1 = 3,5-diClPyr |
|---|---|---|---|---|---|---|
| 2Cl | | | | | | |
| 3Cl | | | | | | |
| 4Cl | | | | AD4-13225 | | |
| 2,3-diCl | | | | AD4-13215 | AD4-13222 | |
| 3,4-diCl | AD4-13204 | AD4-13207 | | | | |
| 2,4-diCl | AD4-13201 | | | AD4-13217 | AD4-13218 | AD4-13231 |
| 2,5-diCl | | | AD4-13221 | AD4-13227 | | |
| 3,5-diCl | | | AD4-13216 | AD4-13226 | | |
| 2,6-diCl | | | | | | |
| 2,3,5-triCl | | | AD4-13228 | | | |
| 2Cl—4F | AD4-13198 | AD4-13205 | | | | |
| 2Cl—6F | | | | | | |
| 3F—4Cl | | | | | | |
| 3Cl—4F | | | | | | |
| 4CF3 | | | | | | |
| 3F—4CF3 | | | | | | |
| 2Cl—5CF3 | | | | | | |
| 3CF3-4-Cl | | | | | | |
| 2,4-diCF3 | | | | | | |
| 3CF3 | | | | | | |
| 2F—4CF3 | | | | | | |
| 2,3,5,6-F4 | | | | | | |
| 2,4-diF | | | | | | |
| 3-Me-4-OMe | | | | | | |
| 2-F | | | | | | |
| 2,3,5,6-F4-4-OCH2CF3 | | | | | | |
| 2-Me | | | | | | |
| 3-F | | | | | | |
| 4-OCF3 | | | | | | |
| 3-OH-4-OMe | | | | | | |
| 2-OH-5-Me | | | | | | |
| 3,4-diOMe | | | | | | |
| 2,3,4-triOMe | | | AD4-13214 | | AD4-13219 | |

In some embodiments, the compound of Formula (2) is AD4-1505.

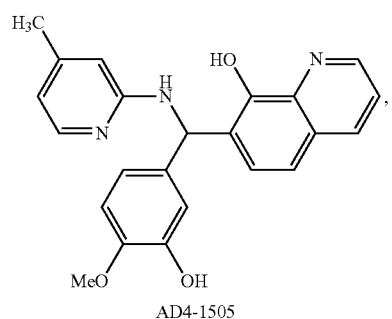

AD4-1505

Formula (1)

In some embodiments, the compound of Formula (2) is selected from a compound of TABLE 5.

TABLE 5

Exemplary Compounds of Formula (2)

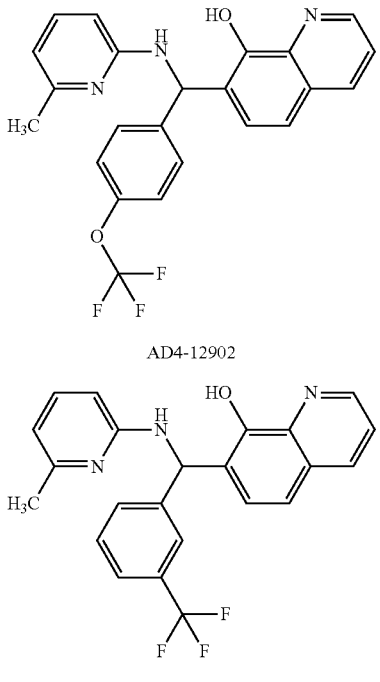

AD4-12902

AD4-12903

TABLE 5-continued
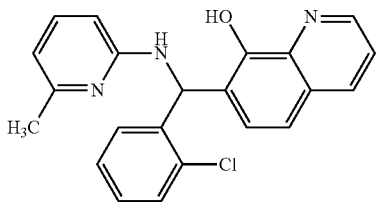 [SMILES: Cc1cccc(NC(c2ccccc2Cl)c2ccc3cccnc3c2O)n1]
AD4-12904
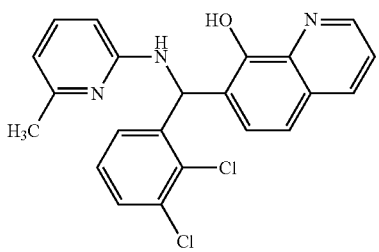 [SMILES: Cc1cccc(NC(c2cccc(Cl)c2Cl)c2ccc3cccnc3c2O)n1]
AD4-12905
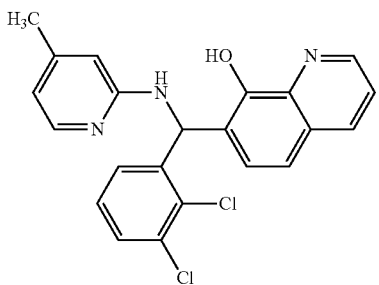 [SMILES: Cc1ccnc(NC(c2cccc(Cl)c2Cl)c2ccc3cccnc3c2O)c1]
AD4-12906
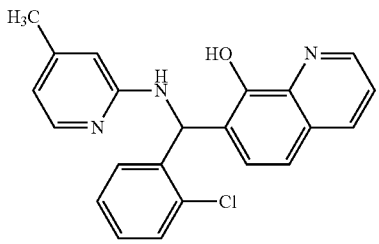 [SMILES: Cc1ccnc(NC(c2ccccc2Cl)c2ccc3cccnc3c2O)c1]
AD4-12907
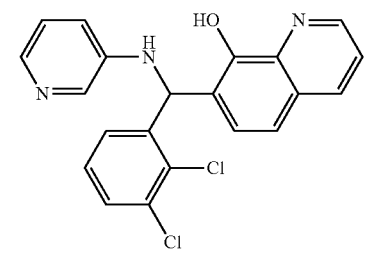 [SMILES: Oc1c(C(Nc2cccnc2)c2cccc(Cl)c2Cl)ccc2cccnc12]
AD4-12908
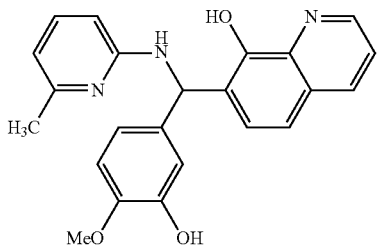 [SMILES: COc1ccc(C(Nc2cccc(C)n2)c2ccc3cccnc3c2O)cc1O]
AD4-12909
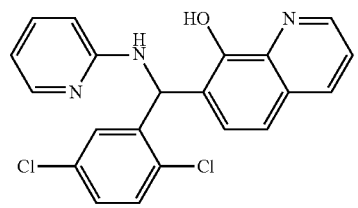 [SMILES: Oc1c(C(Nc2ccccn2)c2cc(Cl)ccc2Cl)ccc2cccnc12]
AD4-12910
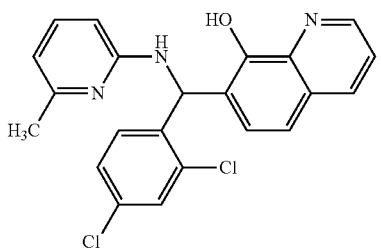 [SMILES: Cc1cccc(NC(c2ccc(Cl)cc2Cl)c2ccc3cccnc3c2O)n1]
AD4-12911
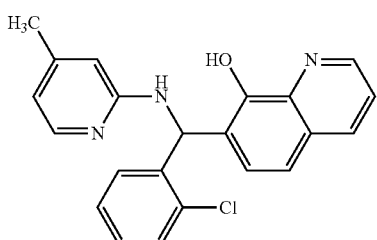
AD4-12912
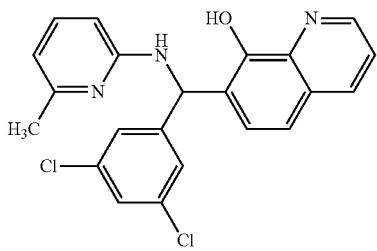 [SMILES: Cc1cccc(NC(c2cc(Cl)cc(Cl)c2)c2ccc3cccnc3c2O)n1]
AD4-12913

TABLE 5-continued
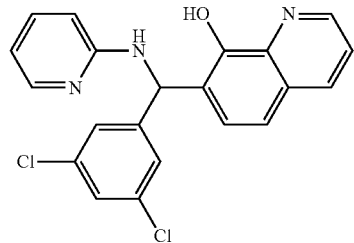 [SMILES: Oc1c(C(Nc2ccccn2)c2cc(Cl)cc(Cl)c2)ccc2cccnc12]
AD4-12914
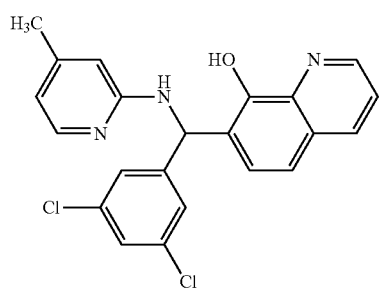 [SMILES: Cc1ccnc(NC(c2cc(Cl)cc(Cl)c2)c2ccc3cccnc3c2O)c1]
AD4-12915
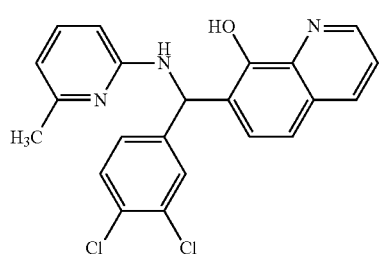
AD4-12916
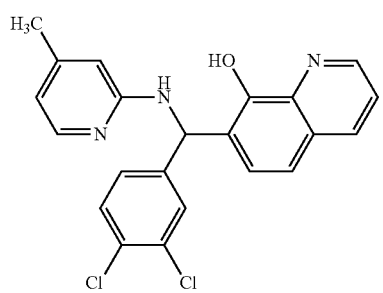 [SMILES: Cc1ccnc(NC(c2ccc(Cl)c(Cl)c2)c2ccc3cccnc3c2O)c1]
AD4-12917
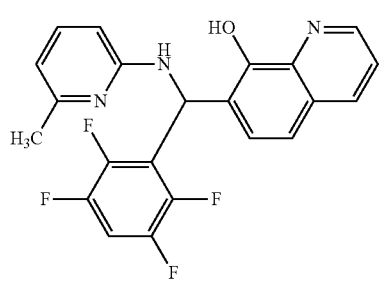 [SMILES: Cc1cccc(NC(c2ccc3cccnc3c2O)c2c(F)c(F)cc(F)c2F)n1]
AD4-12918
TABLE 5-continued
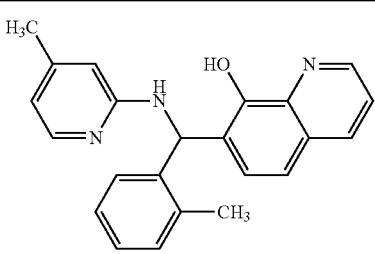
AD4-12935
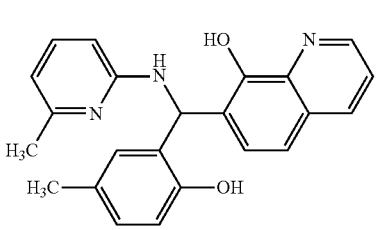
AD4-12936
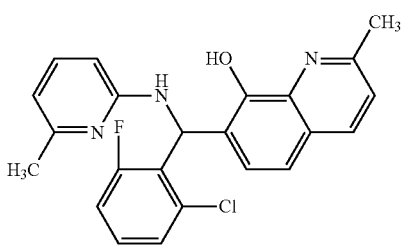 [SMILES: Cc1cccc(NC(c2ccc3ccc(C)nc3c2O)c2c(F)cccc2Cl)n1]
AD4-12937
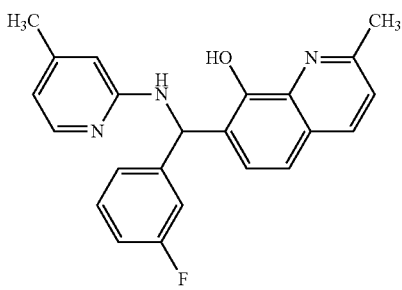 [SMILES: Cc1ccnc(NC(c2cccc(F)c2)c2ccc3ccc(C)nc3c2O)c1]
AD4-12953
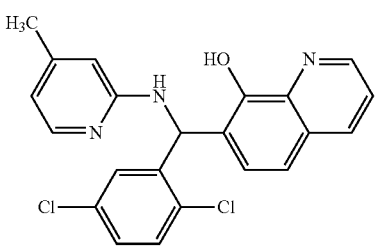 [SMILES: Cc1ccnc(NC(c2cc(Cl)ccc2Cl)c2ccc3cccnc3c2O)c1]
AD4-12954

TABLE 5-continued
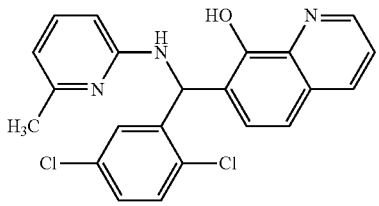 [SMILES: Cc1cccc(NC(c2cc(Cl)ccc2Cl)c2ccc3cccnc3c2O)n1]
AD4-12955
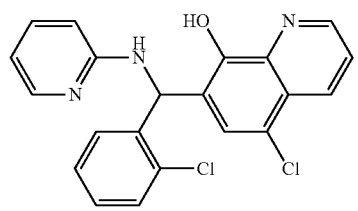 [SMILES: Oc1c(C(Nc2ccccn2)c2ccccc2Cl)cc(Cl)c2cccnc12]
AD4-12958
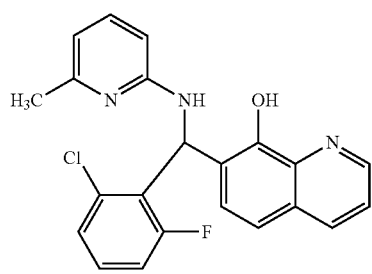 [SMILES: Cc1cccc(NC(c2ccc3cccnc3c2O)c2c(F)cccc2Cl)n1]
AD4-12959
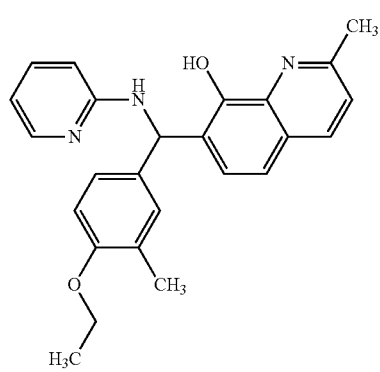 [SMILES: CCOc1ccc(C(Nc2ccccn2)c2ccc3ccc(C)nc3c2O)cc1C]
AD4-12965
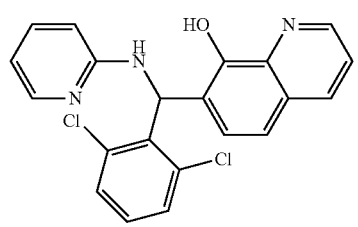 [SMILES: Oc1c(C(Nc2ccccn2)c2c(Cl)cccc2Cl)ccc2cccnc12]
AD4-12966
TABLE 5-continued
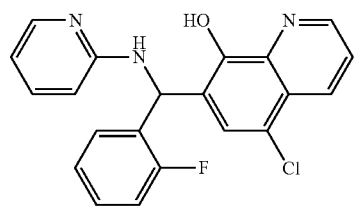 [SMILES: Oc1c(C(Nc2ccccn2)c2ccccc2F)cc(Cl)c2cccnc12]
AD4-12990
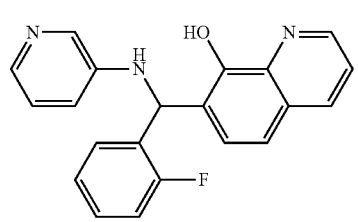 [SMILES: Oc1c(C(Nc2cccnc2)c2ccccc2F)ccc2cccnc12]
AD4-12991
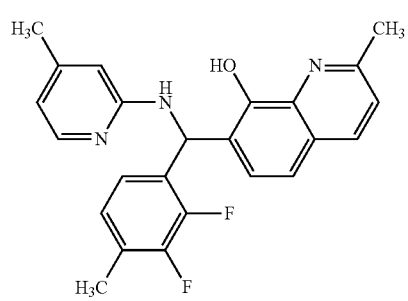 [SMILES: Cc1ccnc(NC(c2ccc(C)c(F)c2F)c2ccc3ccc(C)nc3c2O)c1]
AD4-13018
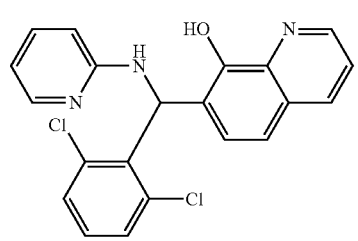 [SMILES: Oc1c(C(Nc2ccccn2)c2c(Cl)cccc2Cl)ccc2cccnc12]
AD4-13019
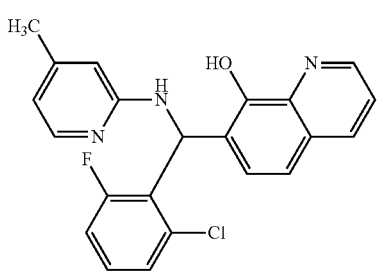 [SMILES: Cc1ccnc(NC(c2ccc3cccnc3c2O)c2c(F)cccc2Cl)c1]
AD4-13020

TABLE 5-continued
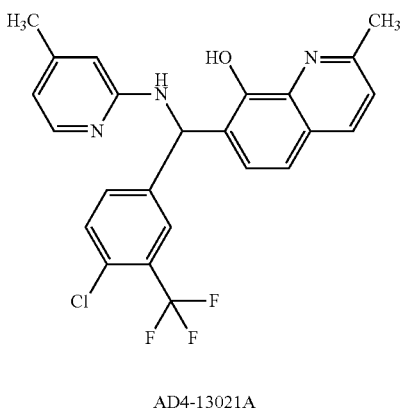
AD4-13021A
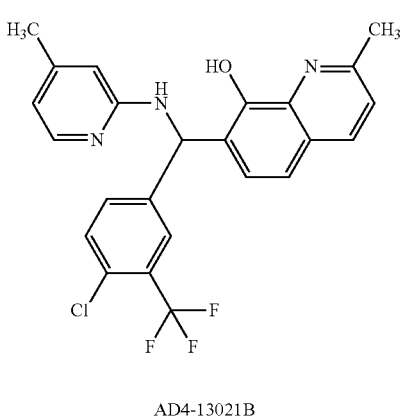
AD4-13021B
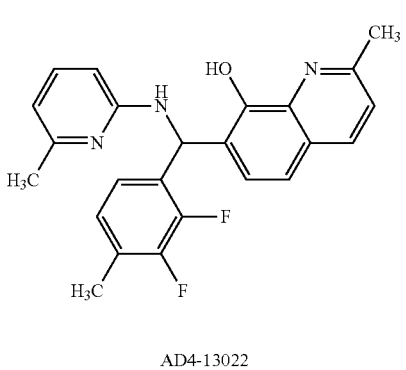
AD4-13022
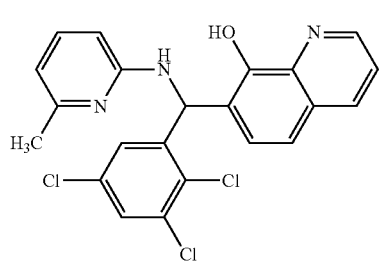 [SMILES: Cc1cccc(NC(c2cc(Cl)cc(Cl)c2Cl)c2ccc3cccnc3c2O)n1]
AD4-13023
TABLE 5-continued
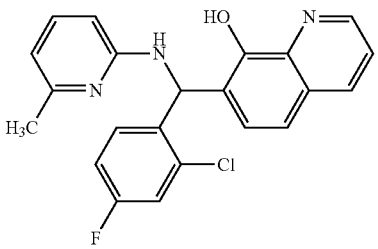 [SMILES: Cc1cccc(NC(c2ccc(F)cc2Cl)c2ccc3cccnc3c2O)n1]
AD4-13024
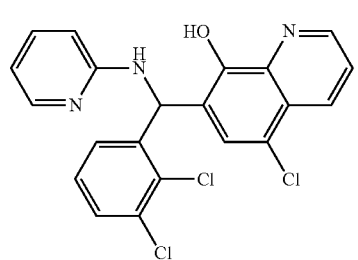 [SMILES: Oc1c(C(Nc2ccccn2)c2cccc(Cl)c2Cl)cc(Cl)c2cccnc12]
AD4-13025
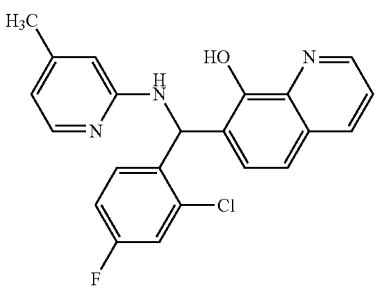
AD4-13026
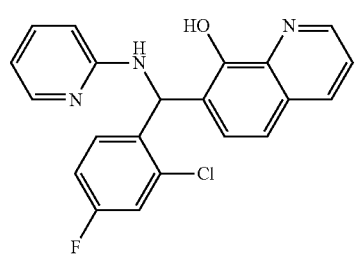 [SMILES: Oc1c(C(Nc2ccccn2)c2ccc(F)cc2Cl)ccc2cccnc12]
AD4-13027
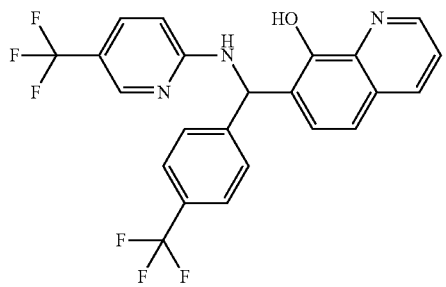
AD4-13028

TABLE 5-continued
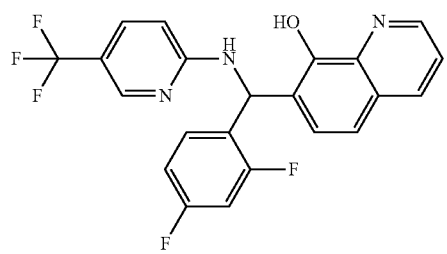
AD4-13029
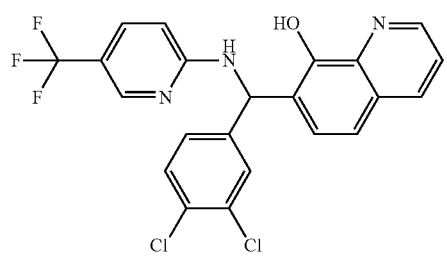
AD4-13030
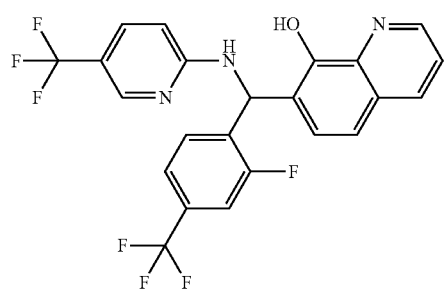
AD4-13031
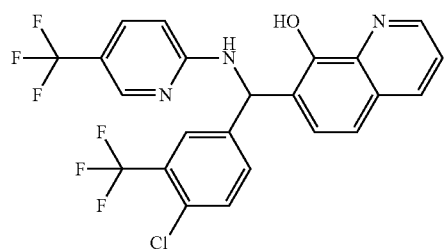 [SMILES: Oc1c(C(Nc2ccc(C(F)(F)F)cn2)c2ccc(Cl)c(C(F)(F)F)c2)ccc2cccnc12]
AD4-13032
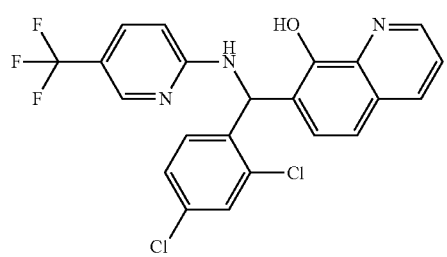
AD4-13033-1
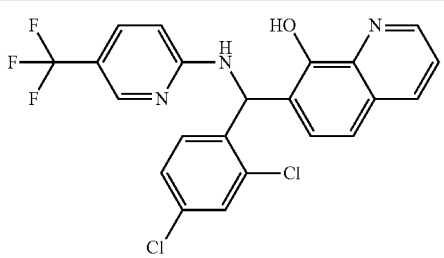
AD4-13033-2
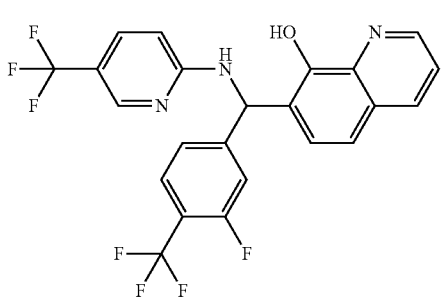 [SMILES: Oc1c(C(Nc2ccc(C(F)(F)F)cn2)c2ccc(C(F)(F)F)c(F)c2)ccc2cccnc12]
AD4-13034
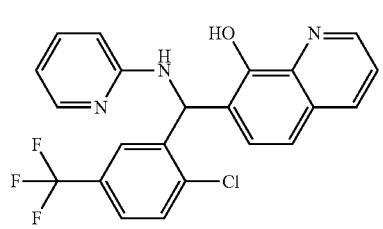 [SMILES: Oc1c(C(Nc2ccccn2)c2cc(C(F)(F)F)ccc2Cl)ccc2cccnc12]
AD4-13035
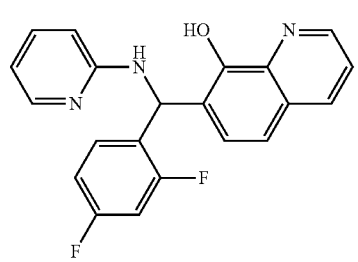 [SMILES: Oc1c(C(Nc2ccccn2)c2ccc(F)cc2F)ccc2cccnc12]
AD4-13036
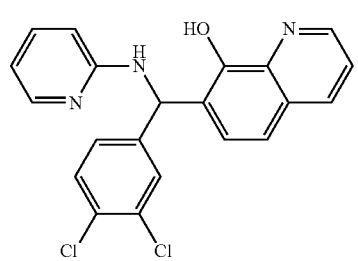 [SMILES: Oc1c(C(Nc2ccccn2)c2ccc(Cl)c(Cl)c2)ccc2cccnc12]
AD4-13037

TABLE 5-continued
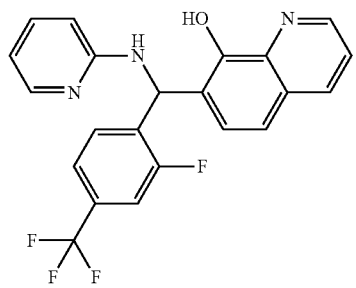 [SMILES: Oc1c(C(Nc2ccccn2)c2ccc(C(F)(F)F)cc2F)ccc2cccnc12]
AD4-13038
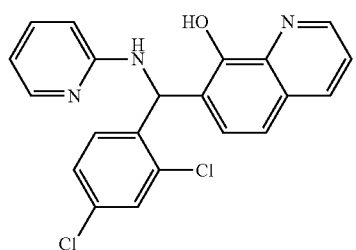 [SMILES: Oc1c(C(Nc2ccccn2)c2ccc(Cl)cc2Cl)ccc2cccnc12]
AD4-13039
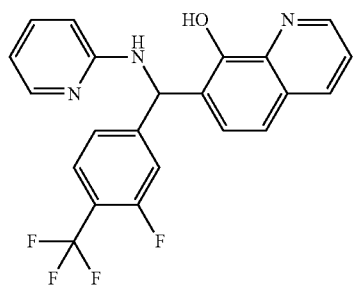 [SMILES: Oc1c(C(Nc2ccccn2)c2ccc(C(F)(F)F)c(F)c2)ccc2cccnc12]
AD4-13040
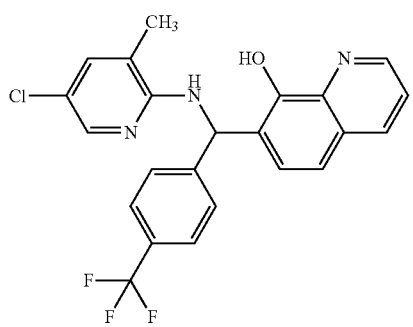 [SMILES: Cc1cc(Cl)cnc1NC(c1ccc(C(F)(F)F)cc1)c1ccc2cccnc2c1O]
AD4-13041
TABLE 5-continued
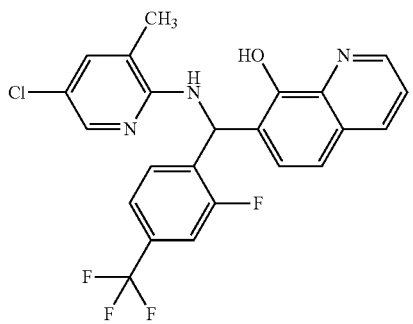 [SMILES: Cc1cc(Cl)cnc1NC(c1ccc(C(F)(F)F)cc1F)c1ccc2cccnc2c1O]
AD4-13042
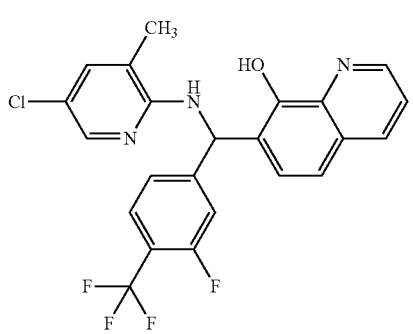 [SMILES: Cc1cc(Cl)cnc1NC(c1ccc(C(F)(F)F)c(F)c1)c1ccc2cccnc2c1O]
AD4-13043
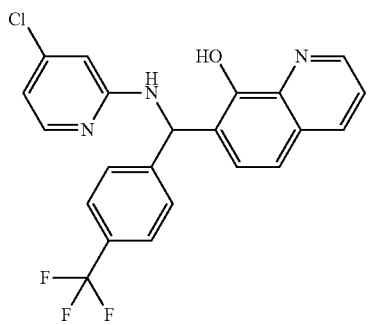 [SMILES: Oc1c(C(Nc2cc(Cl)ccn2)c2ccc(C(F)(F)F)cc2)ccc2cccnc12]
AD4-13044
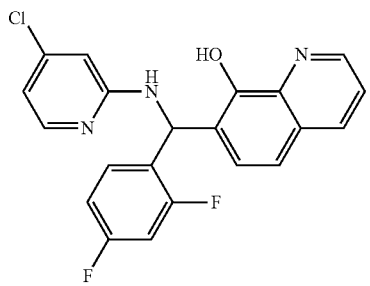 [SMILES: Oc1c(C(Nc2cc(Cl)ccn2)c2ccc(F)cc2F)ccc2cccnc12]
AD4-13045

TABLE 5-continued
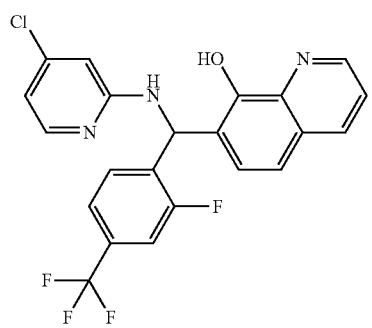 [SMILES: Oc1c(C(Nc2cc(Cl)ccn2)c2ccc(C(F)(F)F)cc2F)ccc2cccnc12]
AD4-13046
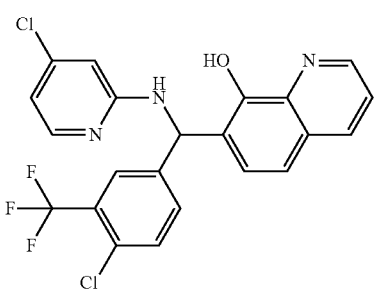 [SMILES: Oc1c(C(Nc2cc(Cl)ccn2)c2ccc(Cl)c(C(F)(F)F)c2)ccc2cccnc12]
AD4-13047
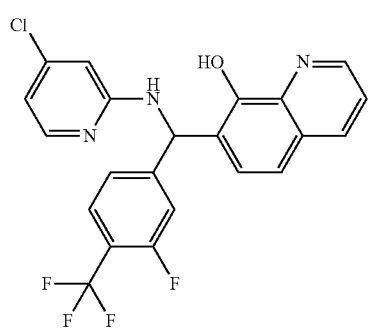 [SMILES: Oc1c(C(Nc2cc(Cl)ccn2)c2ccc(C(F)(F)F)c(F)c2)ccc2cccnc12]
AD4-13048
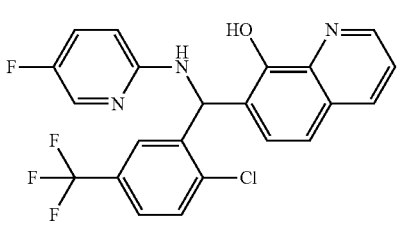 [SMILES: Oc1c(C(Nc2ccc(F)cn2)c2cc(C(F)(F)F)ccc2Cl)ccc2cccnc12]
AD4-13049
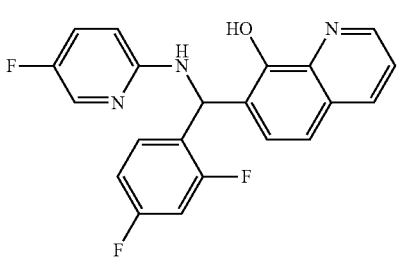 [SMILES: Oc1c(C(Nc2ccc(F)cn2)c2ccc(F)cc2F)ccc2cccnc12]
AD4-13050
TABLE 5-continued
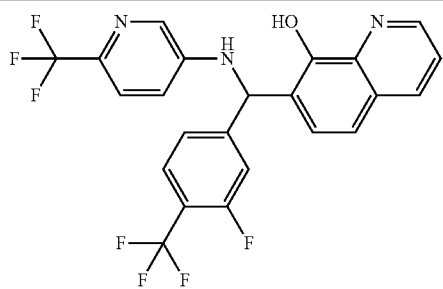 [SMILES: Oc1c(C(Nc2ccc(C(F)(F)F)nc2)c2ccc(C(F)(F)F)c(F)c2)ccc2cccnc12]
AD4-13051
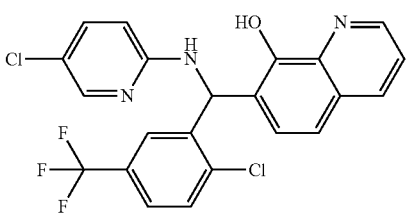 [SMILES: Oc1c(C(Nc2ccc(Cl)cn2)c2cc(C(F)(F)F)ccc2Cl)ccc2cccnc12]
AD4-13052
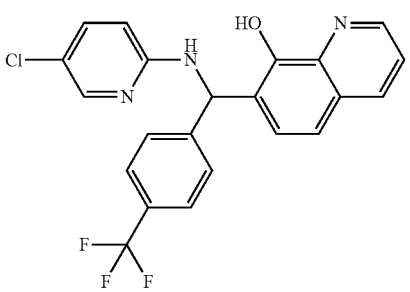 [SMILES: Oc1c(C(Nc2ccc(Cl)cn2)c2ccc(C(F)(F)F)cc2)ccc2cccnc12]
AD4-13053
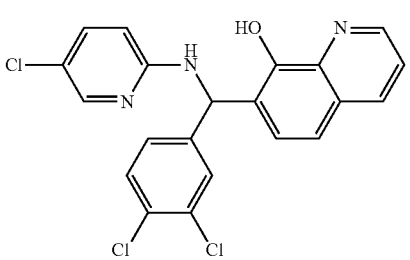
AD4-13054
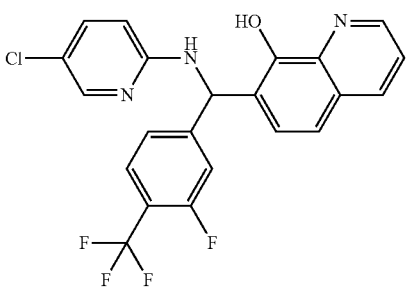 [SMILES: Oc1c(C(Nc2ccc(Cl)cn2)c2ccc(C(F)(F)F)c(F)c2)ccc2cccnc12]
AD4-13055

TABLE 5-continued
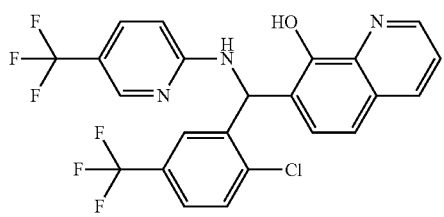
AD4-13056
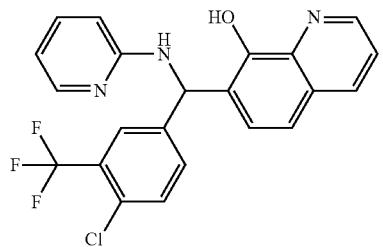 [SMILES: Oc1c(C(Nc2ccccn2)c2ccc(Cl)c(C(F)(F)F)c2)ccc2cccnc12]
AD4-13057
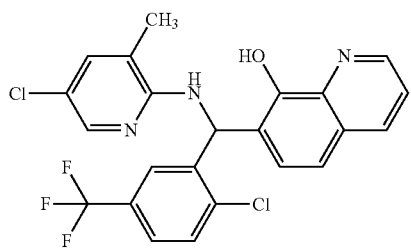 [SMILES: Cc1cc(Cl)cnc1NC(c1cc(C(F)(F)F)ccc1Cl)c1ccc2cccnc2c1O]
AD4-13058
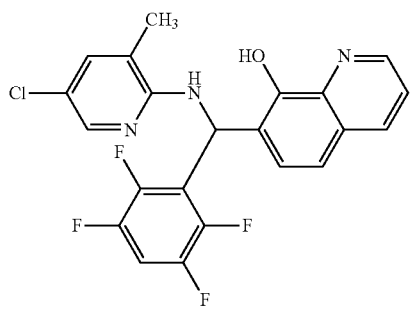 [SMILES: Cc1cc(Cl)cnc1NC(c1ccc2cccnc2c1O)c1c(F)c(F)cc(F)c1F]
AD4-13059
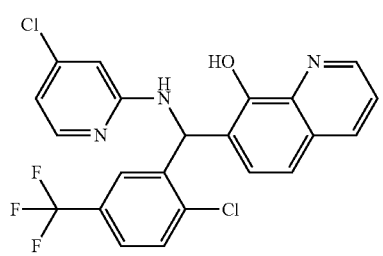 [SMILES: Oc1c(C(Nc2cc(Cl)ccn2)c2cc(C(F)(F)F)ccc2Cl)ccc2cccnc12]
AD4-13060
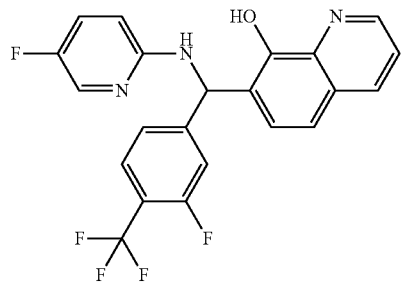 [SMILES: Oc1c(C(Nc2ccc(F)cn2)c2ccc(C(F)(F)F)c(F)c2)ccc2cccnc12]
AD4-13061
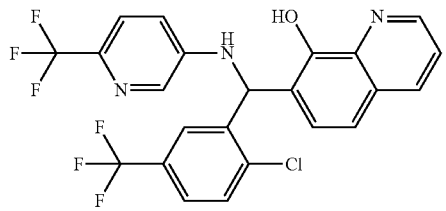 [SMILES: Oc1c(C(Nc2ccc(C(F)(F)F)nc2)c2cc(C(F)(F)F)ccc2Cl)ccc2cccnc12]
AD4-13062
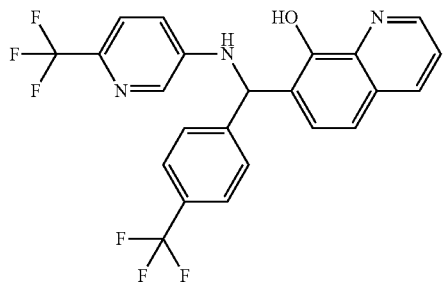 [SMILES: Oc1c(C(Nc2ccc(C(F)(F)F)nc2)c2ccc(C(F)(F)F)cc2)ccc2cccnc12]
AD4-13063
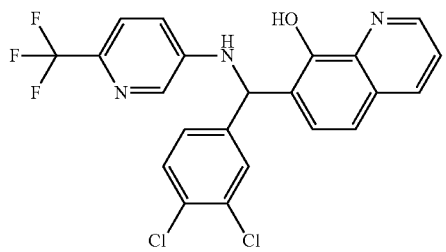 [SMILES: Oc1c(C(Nc2ccc(C(F)(F)F)nc2)c2ccc(Cl)c(Cl)c2)ccc2cccnc12]
AD4-13064
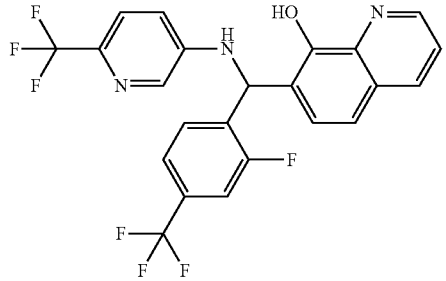 [SMILES: Oc1c(C(Nc2ccc(C(F)(F)F)nc2)c2ccc(C(F)(F)F)cc2F)ccc2cccnc12]
AD4-13065

TABLE 5-continued
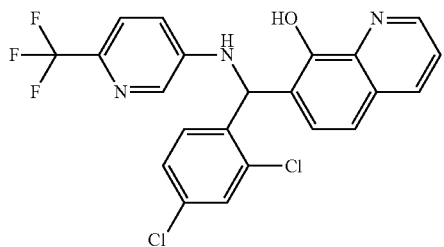 [SMILES: Oc1c(C(Nc2ccc(C(F)(F)F)nc2)c2ccc(Cl)cc2Cl)ccc2cccnc12]
AD4-13066
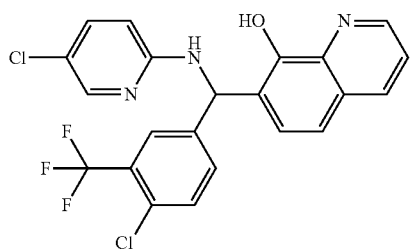 [SMILES: Oc1c(C(Nc2ccc(Cl)cn2)c2ccc(Cl)c(C(F)(F)F)c2)ccc2cccnc12]
AD4-13067
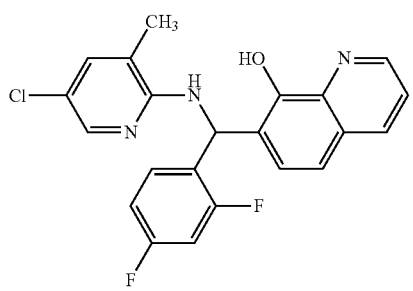
AD4-13068
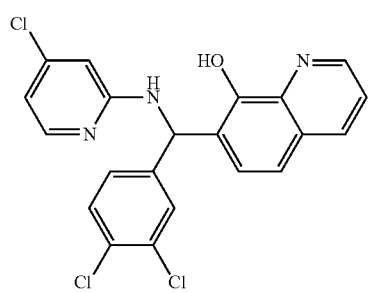 [SMILES: Oc1c(C(Nc2cc(Cl)ccn2)c2ccc(Cl)c(Cl)c2)ccc2cccnc12]
AD4-13069
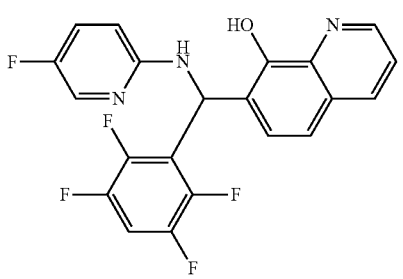 [SMILES: Oc1c(C(Nc2ccc(F)cn2)c2c(F)c(F)cc(F)c2F)ccc2cccnc12]
AD4-13070
TABLE 5-continued
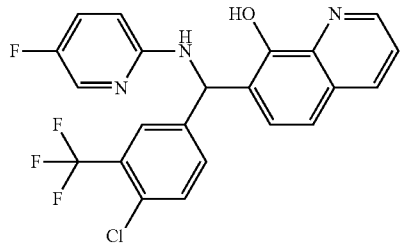 [SMILES: Oc1c(C(Nc2ccc(F)cn2)c2ccc(Cl)c(C(F)(F)F)c2)ccc2cccnc12]
AD4-13071
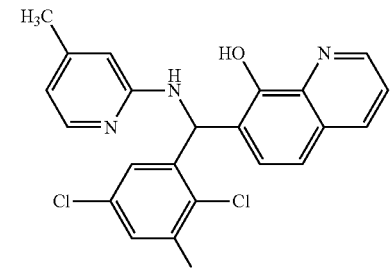
AD4-13072
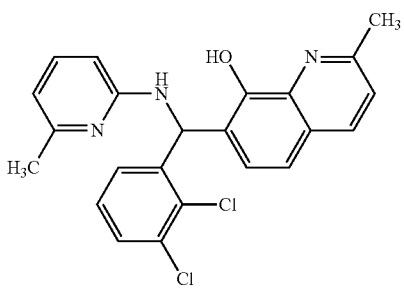 [SMILES: Cc1cccc(NC(c2cccc(Cl)c2Cl)c2ccc3ccc(C)nc3c2O)n1]
AD4-13073
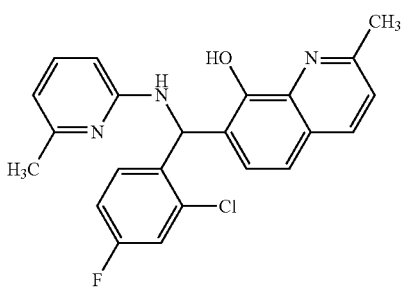 [SMILES: Cc1cccc(NC(c2ccc(F)cc2Cl)c2ccc3ccc(C)nc3c2O)n1]
AD4-13074
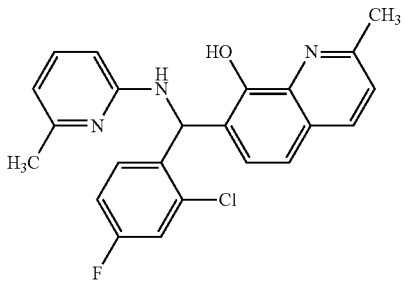 [SMILES: Cc1cccc(NC(c2ccc(F)cc2Cl)c2ccc3ccc(C)nc3c2O)n1]
AD4-13074-2

TABLE 5-continued
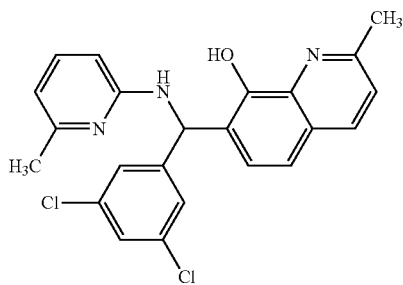 [SMILES: Cc1cccc(NC(c2cc(Cl)cc(Cl)c2)c2ccc3ccc(C)nc3c2O)n1]
AD4-13075
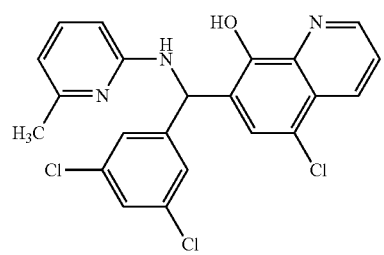 [SMILES: Cc1cccc(NC(c2cc(Cl)cc(Cl)c2)c2cc(Cl)c3cccnc3c2O)n1]
AD4-13076
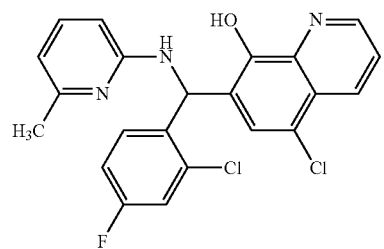 [SMILES: Cc1cccc(NC(c2ccc(F)cc2Cl)c2cc(Cl)c3cccnc3c2O)n1]
AD4-13077
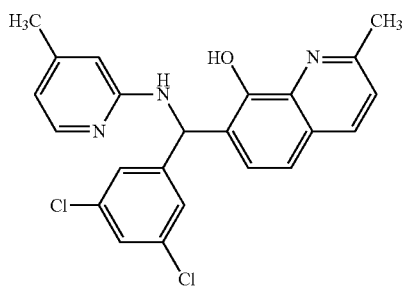 [SMILES: Cc1ccnc(NC(c2cc(Cl)cc(Cl)c2)c2ccc3ccc(C)nc3c2O)c1]
AD4-13078
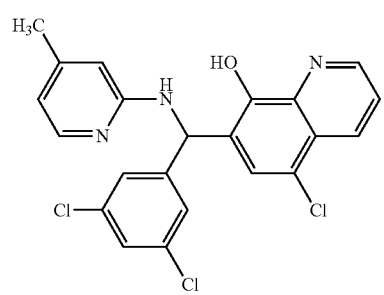 [SMILES: Cc1ccnc(NC(c2cc(Cl)cc(Cl)c2)c2cc(Cl)c3cccnc3c2O)c1]
AD4-13079
TABLE 5-continued
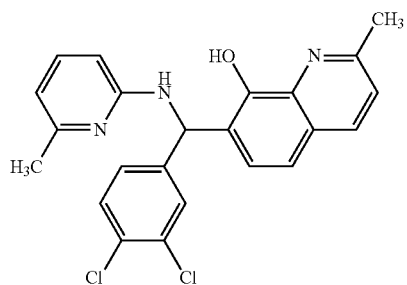 [SMILES: Cc1cccc(NC(c2ccc(Cl)c(Cl)c2)c2ccc3ccc(C)nc3c2O)n1]
AD4-13080
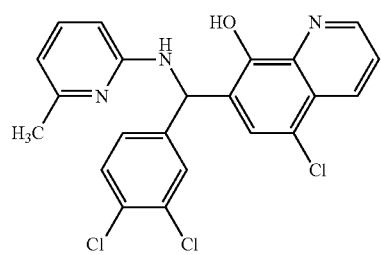 [SMILES: Cc1cccc(NC(c2ccc(Cl)c(Cl)c2)c2cc(Cl)c3cccnc3c2O)n1]
AD4-13081
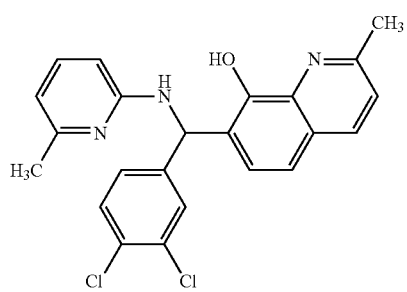 [SMILES: Cc1cccc(NC(c2ccc(Cl)c(Cl)c2)c2ccc3ccc(C)nc3c2O)n1]
AD4-13080
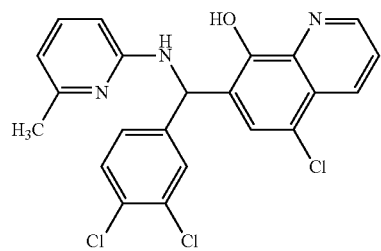 [SMILES: Cc1cccc(NC(c2ccc(Cl)c(Cl)c2)c2cc(Cl)c3cccnc3c2O)n1]
AD4-13081
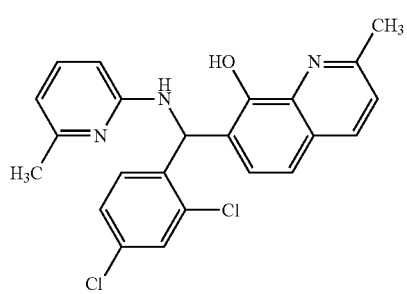 [SMILES: Cc1cccc(NC(c2ccc(Cl)cc2Cl)c2ccc3ccc(C)nc3c2O)n1]
AD4-13082

TABLE 5-continued
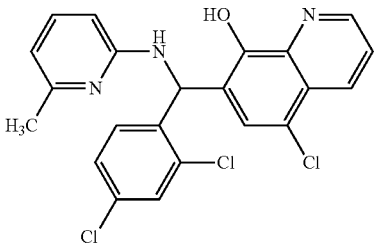
AD4-13083
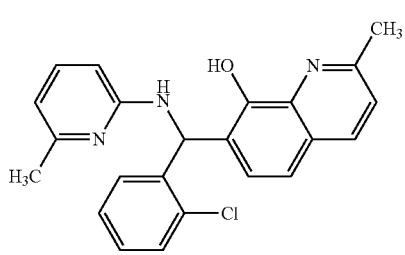 [SMILES: Cc1cccc(NC(c2ccccc2Cl)c2ccc3ccc(C)nc3c2O)n1]
AD4-13084
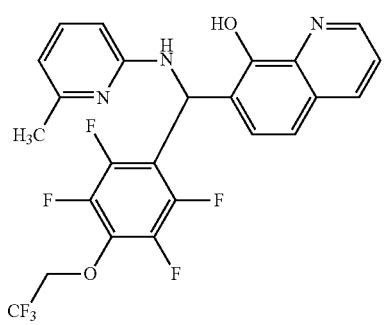 [SMILES: Cc1cccc(NC(c2ccc3cccnc3c2O)c2c(F)c(F)c(OCC(F)(F)F)c(F)c2F)n1]
AD4-13085
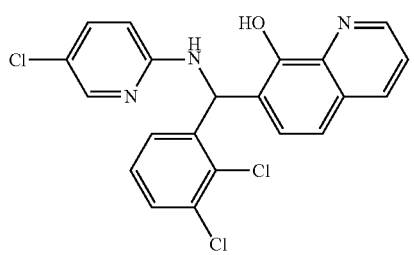 [SMILES: Oc1c(C(Nc2ccc(Cl)cn2)c2cccc(Cl)c2Cl)ccc2cccnc12]
AD4-13086
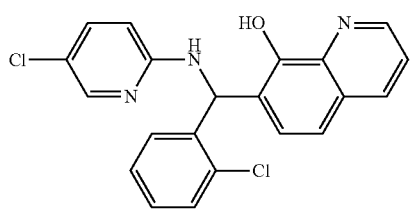 [SMILES: Oc1c(C(Nc2ccc(Cl)cn2)c2ccccc2Cl)ccc2cccnc12]
AD4-13087
TABLE 5-continued
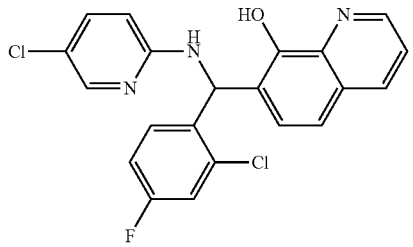 [SMILES: Oc1c(C(Nc2ccc(Cl)cn2)c2ccc(F)cc2Cl)ccc2cccnc12]
AD4-13088
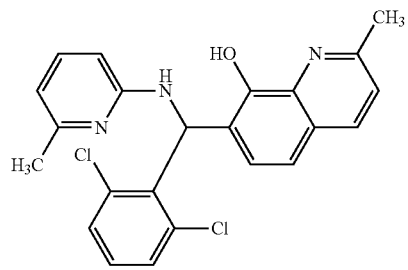 [SMILES: Cc1cccc(NC(c2ccc3ccc(C)nc3c2O)c2c(Cl)cccc2Cl)n1]
AD4-13089
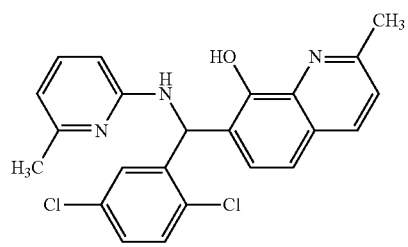 [SMILES: Cc1cccc(NC(c2cc(Cl)ccc2Cl)c2ccc3ccc(C)nc3c2O)n1]
AD4-13090
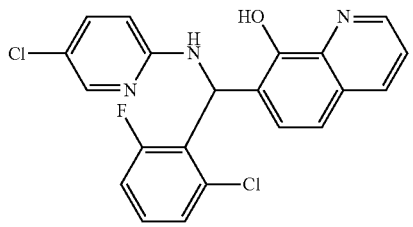 [SMILES: Oc1c(C(Nc2ccc(Cl)cn2)c2c(F)cccc2Cl)ccc2cccnc12]
AD4-13091
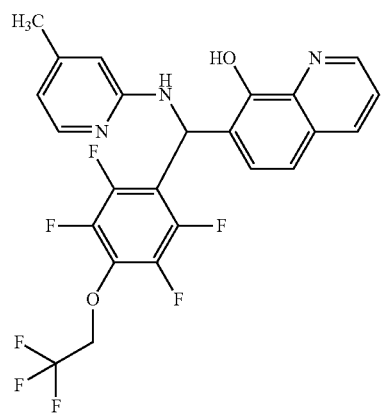 [SMILES: Cc1ccnc(NC(c2ccc3cccnc3c2O)c2c(F)c(F)c(OCC(F)(F)F)c(F)c2F)c1]
AD4-13092

TABLE 5-continued
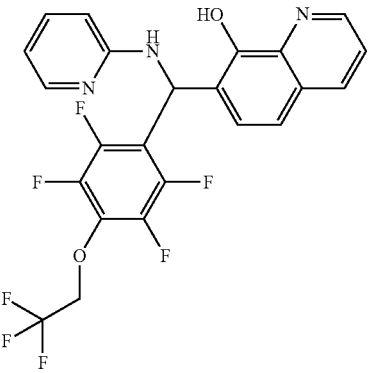 [SMILES: Oc1c(C(Nc2ccccn2)c2c(F)c(F)c(OCC(F)(F)F)c(F)c2F)ccc2cccnc12]
AD4-13093
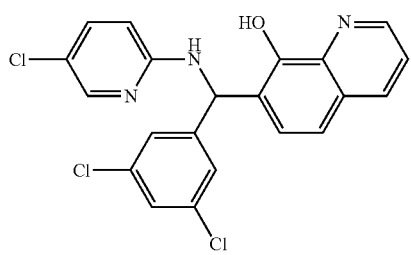 [SMILES: Oc1c(C(Nc2ccc(Cl)cn2)c2cc(Cl)cc(Cl)c2)ccc2cccnc12]
AD4-13094
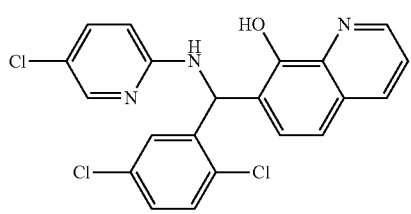 [SMILES: Oc1c(C(Nc2ccc(Cl)cn2)c2cc(Cl)ccc2Cl)ccc2cccnc12]
AD4-13095
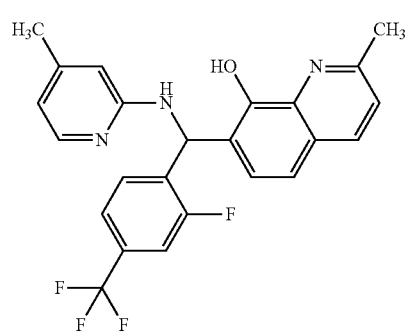 [SMILES: Cc1ccnc(NC(c2ccc(C(F)(F)F)cc2F)c2ccc3ccc(C)nc3c2O)c1]
AD4-13096
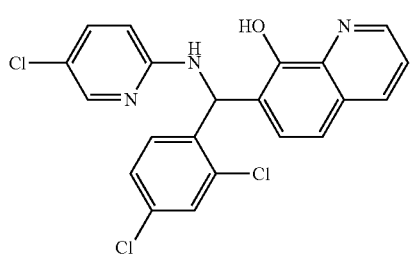 [SMILES: Oc1c(C(Nc2ccc(Cl)cn2)c2ccc(Cl)cc2Cl)ccc2cccnc12]
AD4-13097
TABLE 5-continued
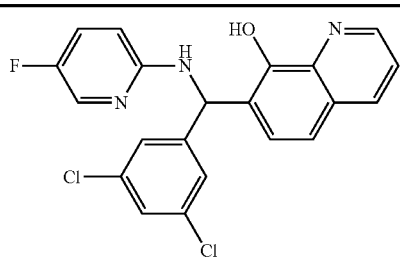
AD4-13098
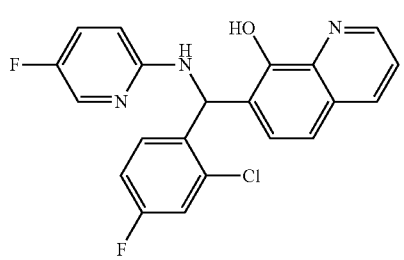
AD4-13099
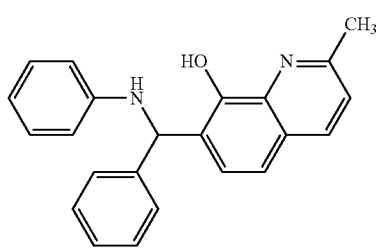 [SMILES: Cc1ccc2ccc(C(Nc3ccccc3)c3ccccc3)c(O)c2n1]
AD4-13100
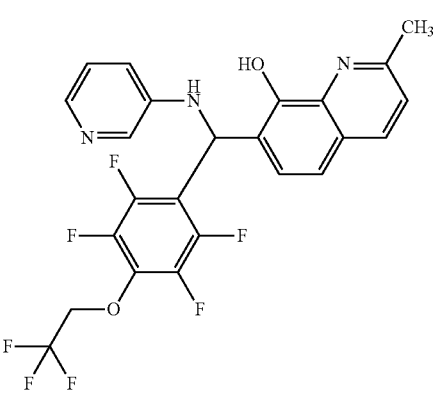 [SMILES: Cc1ccc2ccc(C(Nc3cccnc3)c3c(F)c(F)c(OCC(F)(F)F)c(F)c3F)c(O)c2n1]
AD4-13101
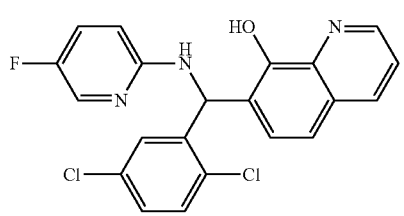 [SMILES: Oc1c(C(Nc2ccc(F)cn2)c2cc(Cl)ccc2Cl)ccc2cccnc12]
AD4-13102

TABLE 5-continued
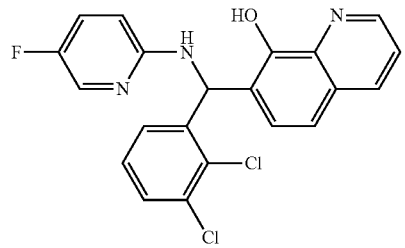 [SMILES: Oc1c(C(Nc2ccc(F)cn2)c2cccc(Cl)c2Cl)ccc2cccnc12]
AD4-13103
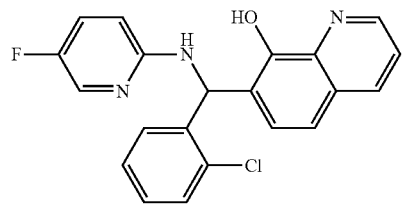 [SMILES: Oc1c(C(Nc2ccc(F)cn2)c2ccccc2Cl)ccc2cccnc12]
AD4-13104
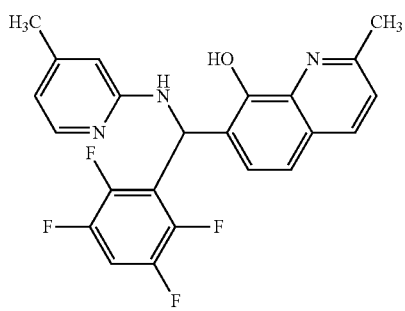 [SMILES: Cc1ccnc(NC(c2ccc3ccc(C)nc3c2O)c2c(F)c(F)cc(F)c2F)c1]
AD4-13105
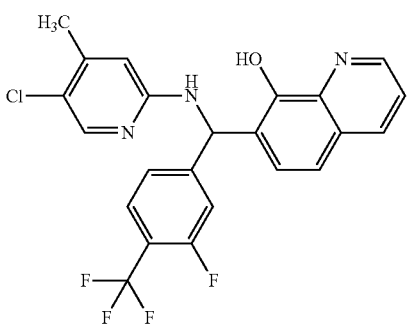 [SMILES: Cc1cc(NC(c2ccc(C(F)(F)F)c(F)c2)c2ccc3cccnc3c2O)ncc1Cl]
AD4-13106
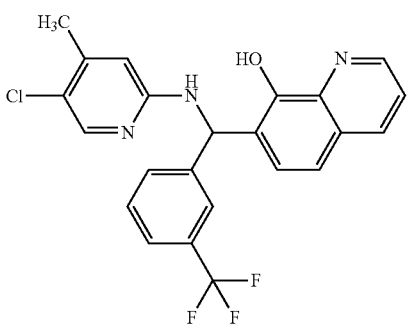 [SMILES: Cc1cc(NC(c2cccc(C(F)(F)F)c2)c2ccc3cccnc3c2O)ncc1Cl]
AD4-13107
TABLE 5-continued
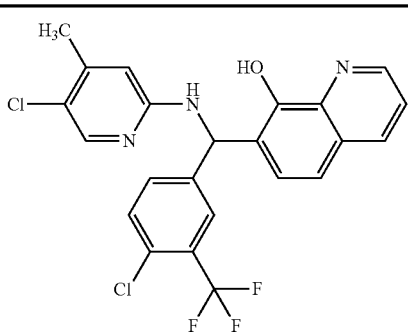
AD4-13108
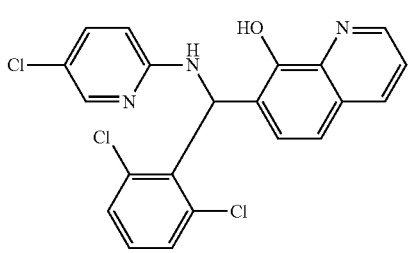 [SMILES: Oc1c(C(Nc2ccc(Cl)cn2)c2c(Cl)cccc2Cl)ccc2cccnc12]
AD4-13109
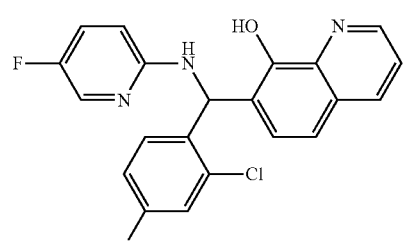
AD4-13110
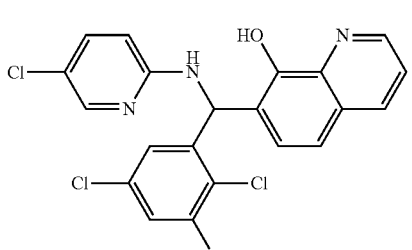
AD4-13111
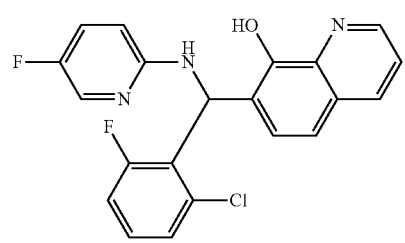 [SMILES: Oc1c(C(Nc2ccc(F)cn2)c2c(F)cccc2Cl)ccc2cccnc12]
AD4-13112

TABLE 5-continued
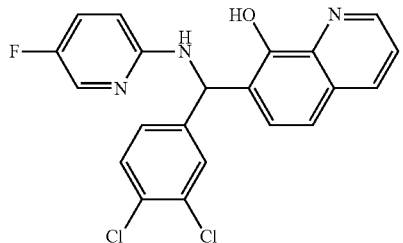 [SMILES: Oc1c(C(Nc2ccc(F)cn2)c2ccc(Cl)c(Cl)c2)ccc2cccnc12]
AD4-13113
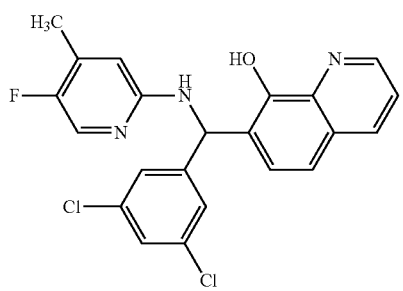 [SMILES: Cc1cc(NC(c2cc(Cl)cc(Cl)c2)c2ccc3cccnc3c2O)ncc1F]
AD4-13114
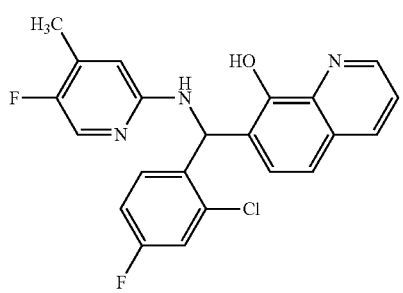 [SMILES: Cc1cc(NC(c2ccc(F)cc2Cl)c2ccc3cccnc3c2O)ncc1F]
AD4-13115
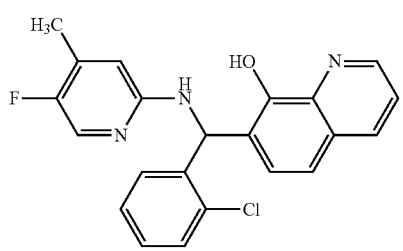 [SMILES: Cc1cc(NC(c2ccccc2Cl)c2ccc3cccnc3c2O)ncc1F]
AD4-13116
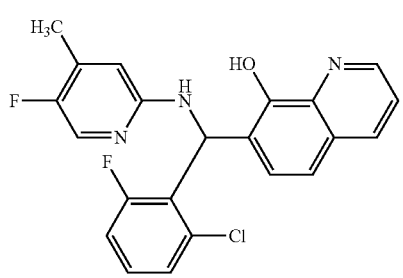 [SMILES: Cc1cc(NC(c2ccc3cccnc3c2O)c2c(F)cccc2Cl)ncc1F]
AD4-13117
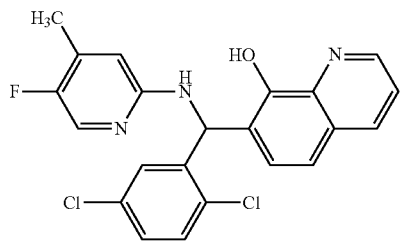 [SMILES: Cc1cc(NC(c2cc(Cl)ccc2Cl)c2ccc3cccnc3c2O)ncc1F]
AD4-13118
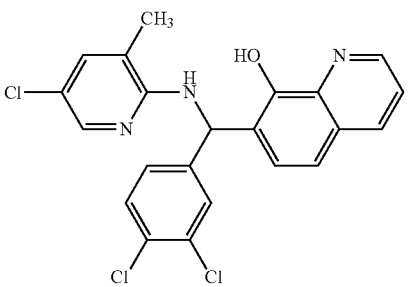 [SMILES: Cc1cc(Cl)cnc1NC(c1ccc(Cl)c(Cl)c1)c1ccc2cccnc2c1O]
AD4-13119
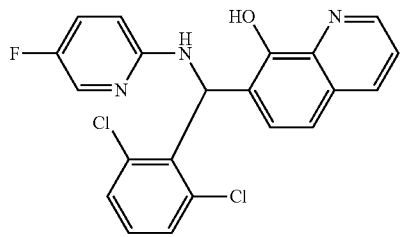 [SMILES: Oc1c(C(Nc2ccc(F)cn2)c2c(Cl)cccc2Cl)ccc2cccnc12]
AD4-13120
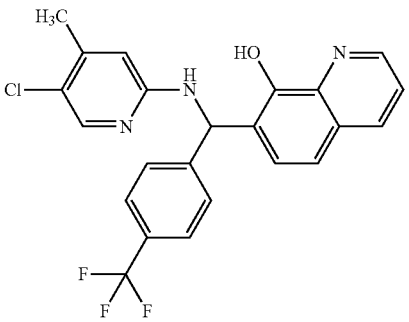 [SMILES: Cc1cc(NC(c2ccc(C(F)(F)F)cc2)c2ccc3cccnc3c2O)ncc1Cl]
AD4-13121
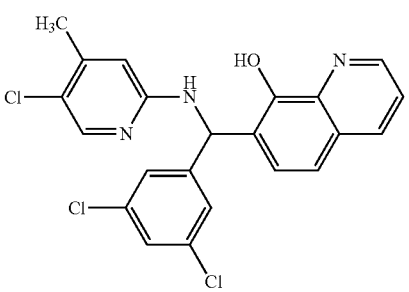 [SMILES: Cc1cc(NC(c2cc(Cl)cc(Cl)c2)c2ccc3cccnc3c2O)ncc1Cl]
AD4-13122

TABLE 5-continued
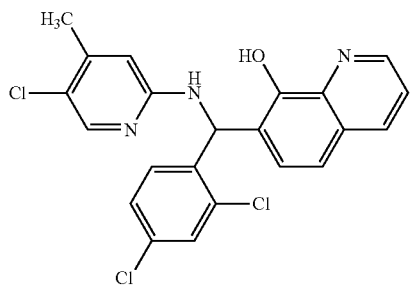
AD4-13123
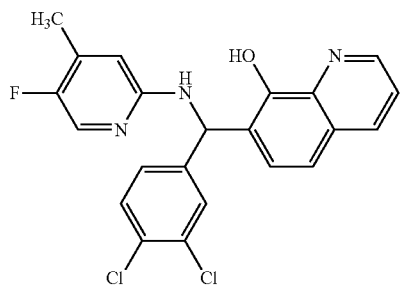
AD4-13127
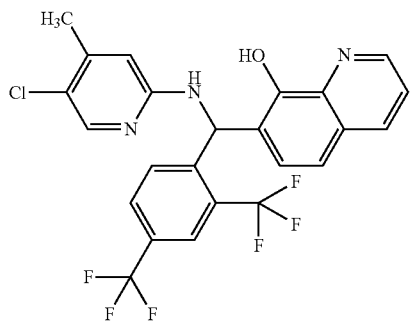 [SMILES: Cc1cc(NC(c2ccc(C(F)(F)F)cc2C(F)(F)F)c2ccc3cccnc3c2O)ncc1Cl]
AD4-13124
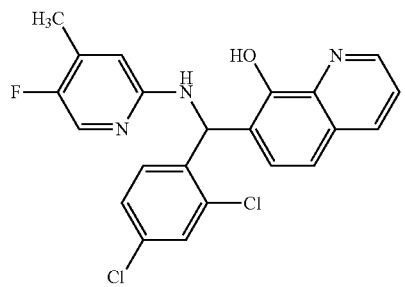
AD4-13128
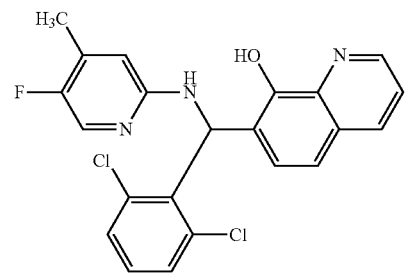 [SMILES: Cc1cc(NC(c2ccc3cccnc3c2O)c2c(Cl)cccc2Cl)ncc1F]
AD4-13125
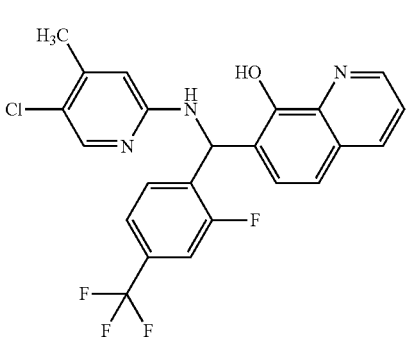
AD4-13129
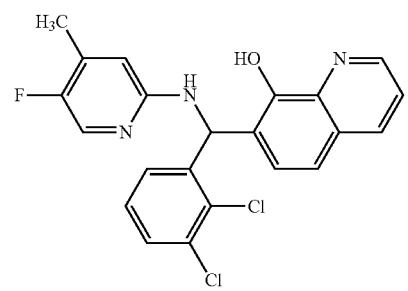 [SMILES: Cc1cc(NC(c2cccc(Cl)c2Cl)c2ccc3cccnc3c2O)ncc1F]
AD4-13126
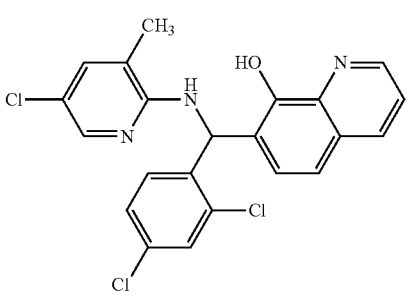
AD4-13130

TABLE 5-continued
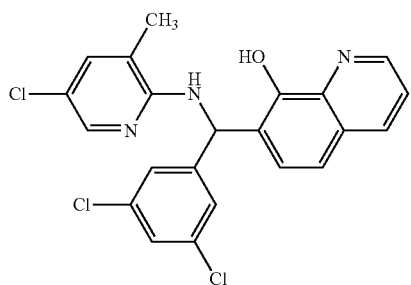 [SMILES: Cc1cc(Cl)cnc1NC(c1cc(Cl)cc(Cl)c1)c1ccc2cccnc2c1O]
AD4-13131
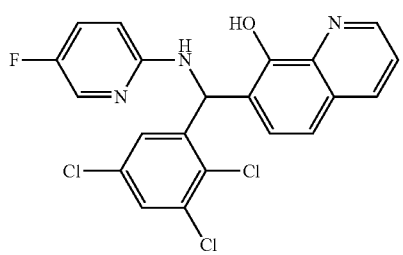 [SMILES: Oc1c(C(Nc2ccc(F)cn2)c2cc(Cl)cc(Cl)c2Cl)ccc2cccnc12]
AD4-13132
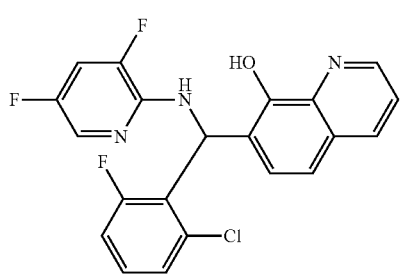 [SMILES: Oc1c(C(Nc2ncc(F)cc2F)c2c(F)cccc2Cl)ccc2cccnc12]
AD4-13133
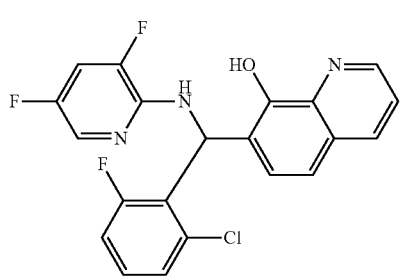 [SMILES: Oc1c(C(Nc2ncc(F)cc2F)c2c(F)cccc2Cl)ccc2cccnc12]
AD4-13133
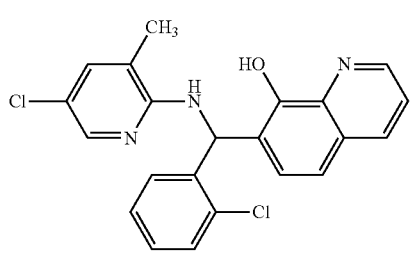 [SMILES: Cc1cc(Cl)cnc1NC(c1ccccc1Cl)c1ccc2cccnc2c1O]
AD4-13134
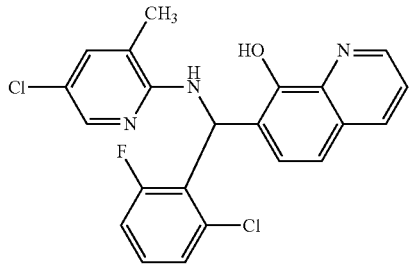 [SMILES: Cc1cc(Cl)cnc1NC(c1ccc2cccnc2c1O)c1c(F)cccc1Cl]
AD4-13135
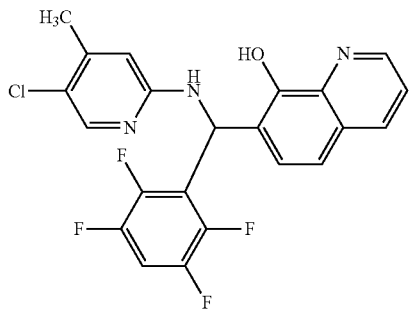 [SMILES: Cc1cc(NC(c2ccc3cccnc3c2O)c2c(F)c(F)cc(F)c2F)ncc1Cl]
AD4-13136
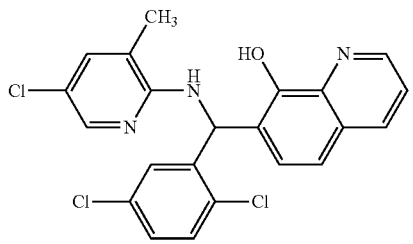
AD4-13137
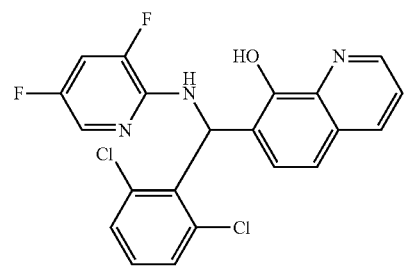 [SMILES: Oc1c(C(Nc2ncc(F)cc2F)c2c(Cl)cccc2Cl)ccc2cccnc12]
AD4-13138
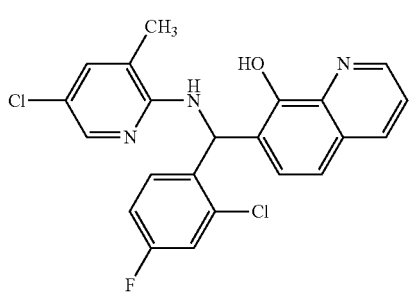
AD4-13139

TABLE 5-continued
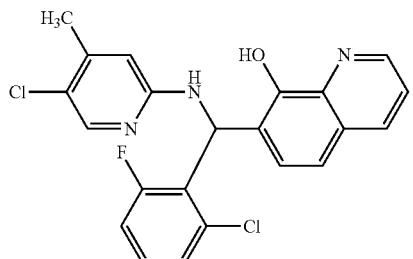
AD4-13140
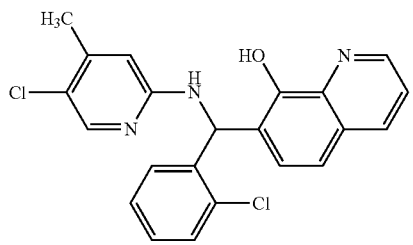 [SMILES: Cc1cc(NC(c2ccccc2Cl)c2ccc3cccnc3c2O)ncc1Cl]
AD4-13141
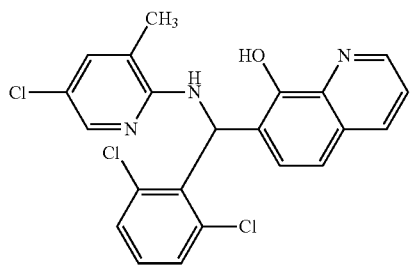 [SMILES: Cc1cc(Cl)cnc1NC(c1ccc2cccnc2c1O)c1c(Cl)cccc1Cl]
AD4-13142
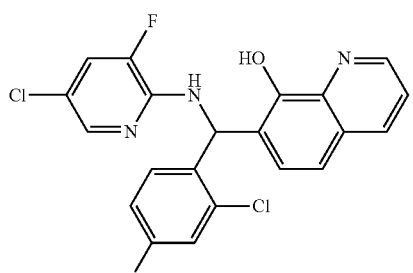
AD4-13143
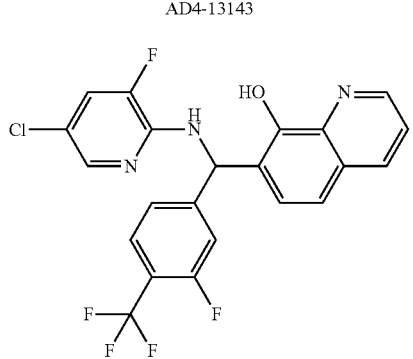
AD4-13144
TABLE 5-continued
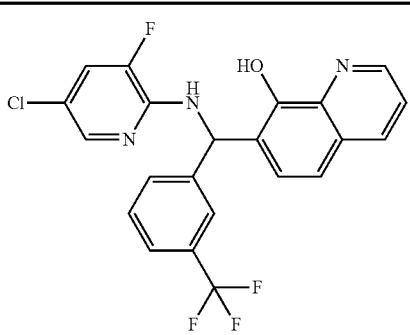
AD4-13145
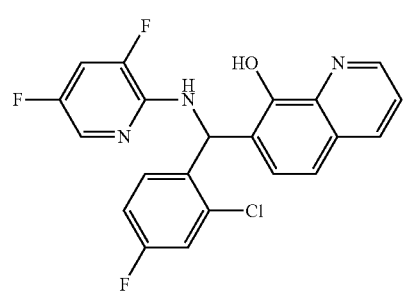 [SMILES: Oc1c(C(Nc2ncc(F)cc2F)c2ccc(F)cc2Cl)ccc2cccnc12]
AD4-13146
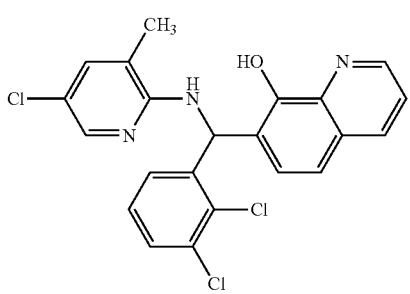 [SMILES: Cc1cc(Cl)cnc1NC(c1cccc(Cl)c1Cl)c1ccc2cccnc2c1O]
AD4-13147
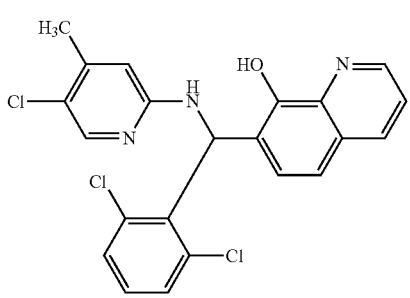 [SMILES: Cc1cc(NC(c2ccc3cccnc3c2O)c2c(Cl)cccc2Cl)ncc1Cl]
AD4-13148

TABLE 5-continued
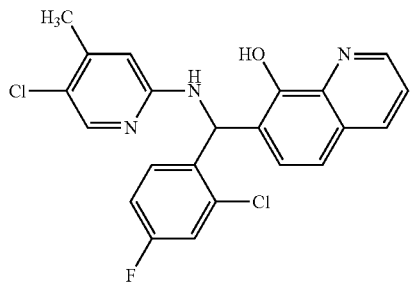 [SMILES: Cc1cc(NC(c2ccc(F)cc2Cl)c2ccc3cccnc3c2O)ncc1Cl]
AD4-13149
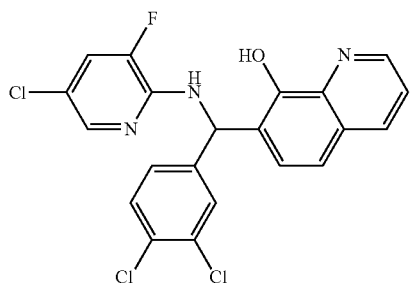 [SMILES: Oc1c(C(Nc2ncc(Cl)cc2F)c2ccc(Cl)c(Cl)c2)ccc2cccnc12]
AD4-13150
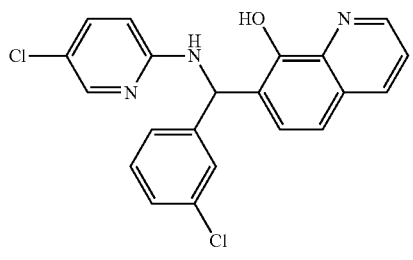 [SMILES: Oc1c(C(Nc2ccc(Cl)cn2)c2cccc(Cl)c2)ccc2cccnc12]
AD4-13151
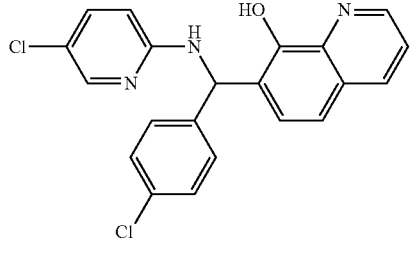 [SMILES: Oc1c(C(Nc2ccc(Cl)cn2)c2ccc(Cl)cc2)ccc2cccnc12]
AD4-13152
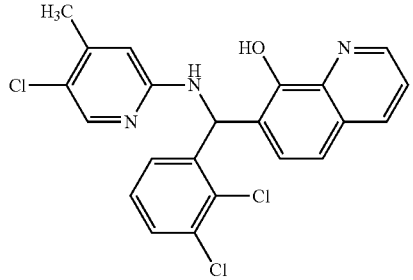 [SMILES: Cc1cc(NC(c2cccc(Cl)c2Cl)c2ccc3cccnc3c2O)ncc1Cl]
AD4-13153
TABLE 5-continued
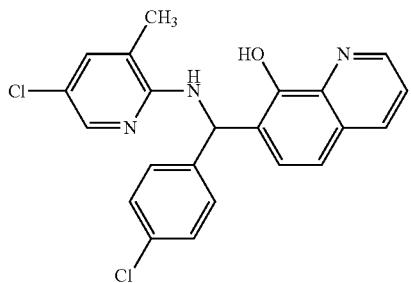 [SMILES: Cc1cc(Cl)cnc1NC(c1ccc(Cl)cc1)c1ccc2cccnc2c1O]
AD4-13154
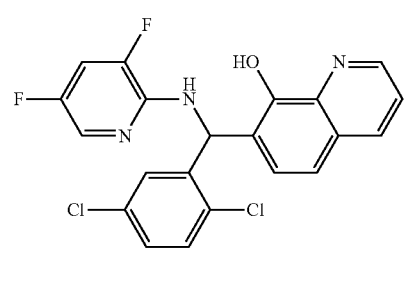 [SMILES: Oc1c(C(Nc2ncc(F)cc2F)c2cc(Cl)ccc2Cl)ccc2cccnc12]
AD4-13155
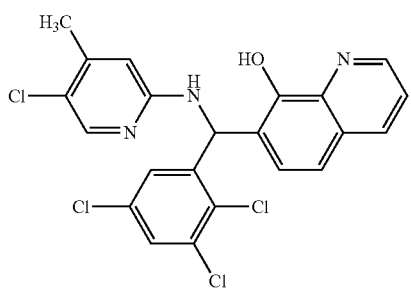
AD4-13156
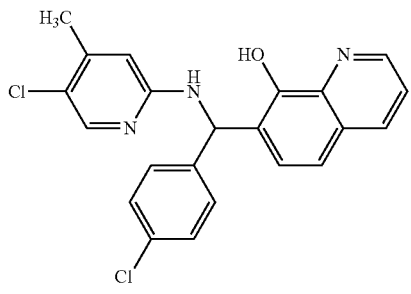 [SMILES: Cc1cc(NC(c2ccc(Cl)cc2)c2ccc3cccnc3c2O)ncc1Cl]
AD4-13157
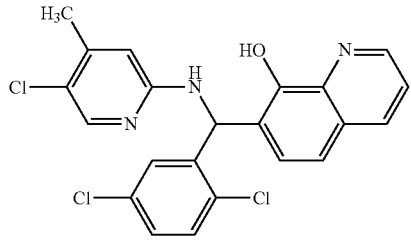
AD4-13158

TABLE 5-continued
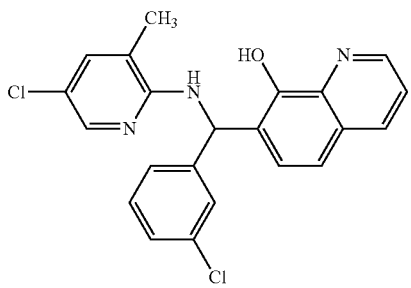
AD4-13159
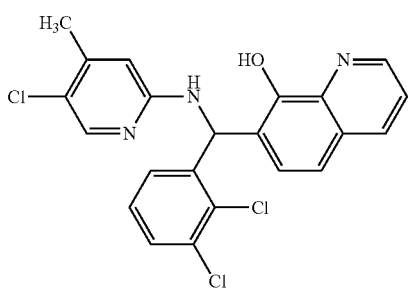
AD4-13160
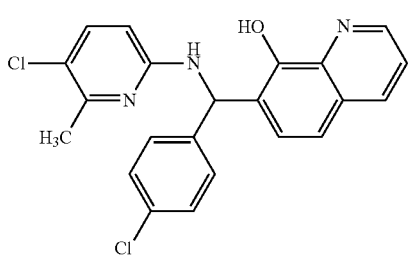 [SMILES: Cc1nc(NC(c2ccc(Cl)cc2)c2ccc3cccnc3c2O)ccc1Cl]
AD4-13161
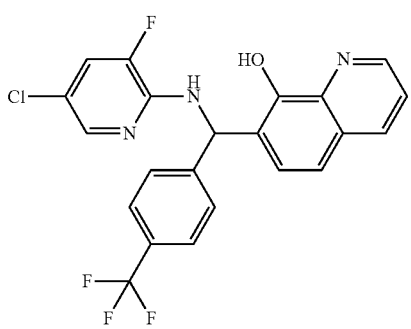 [SMILES: Oc1c(C(Nc2ncc(Cl)cc2F)c2ccc(C(F)(F)F)cc2)ccc2cccnc12]
AD4-13162
TABLE 5-continued
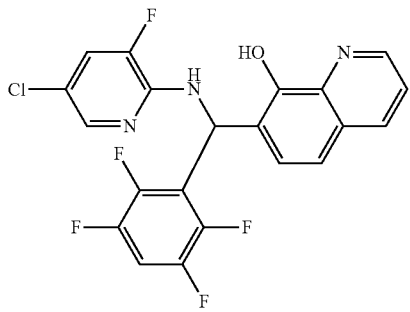 [SMILES: Oc1c(C(Nc2ncc(Cl)cc2F)c2c(F)c(F)cc(F)c2F)ccc2cccnc12]
AD4-13163
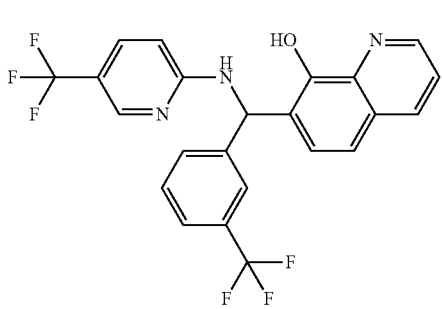 [SMILES: Oc1c(C(Nc2ccc(C(F)(F)F)cn2)c2cccc(C(F)(F)F)c2)ccc2cccnc12]
AD4-13164
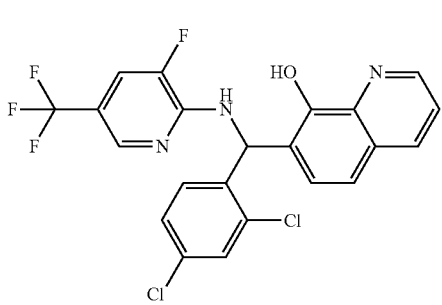 [SMILES: Oc1c(C(Nc2ncc(C(F)(F)F)cc2F)c2ccc(Cl)cc2Cl)ccc2cccnc12]
AD4-13165
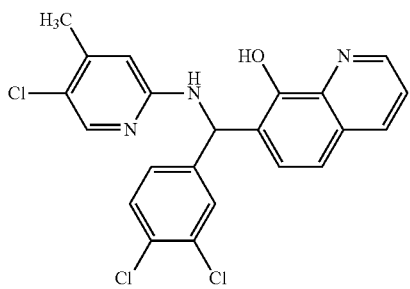 [SMILES: Cc1cc(NC(c2ccc(Cl)c(Cl)c2)c2ccc3cccnc3c2O)ncc1Cl]
AD4-13166

TABLE 5-continued
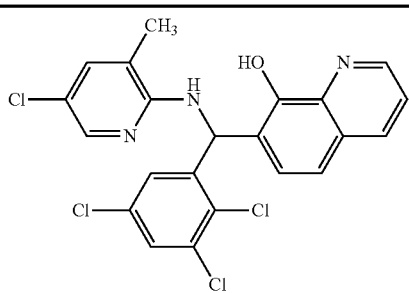
AD4-13167
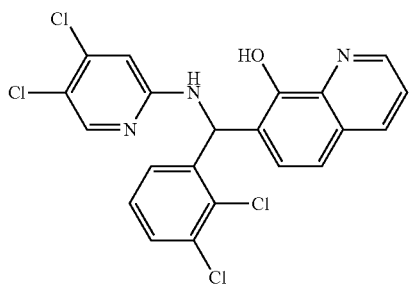 [SMILES: Oc1c(C(Nc2cc(Cl)c(Cl)cn2)c2cccc(Cl)c2Cl)ccc2cccnc12]
AD4-13172
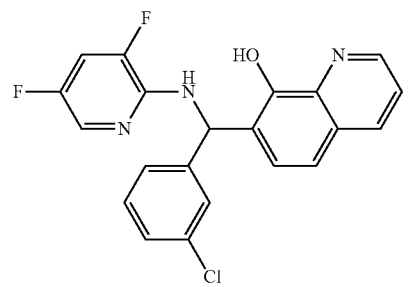 [SMILES: Oc1c(C(Nc2ncc(F)cc2F)c2cccc(Cl)c2)ccc2cccnc12]
AD4-13173
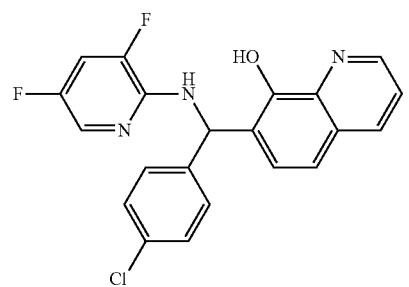 [SMILES: Oc1c(C(Nc2ncc(F)cc2F)c2ccc(Cl)cc2)ccc2cccnc12]
AD4-13174
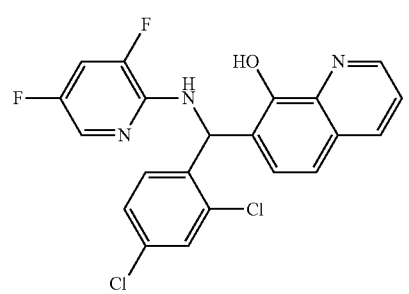 [SMILES: Oc1c(C(Nc2ncc(F)cc2F)c2ccc(Cl)cc2Cl)ccc2cccnc12]
AD4-13175
TABLE 5-continued
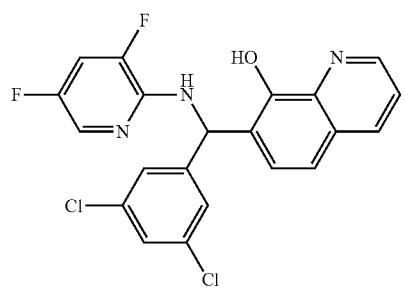 [SMILES: Oc1c(C(Nc2ncc(F)cc2F)c2cc(Cl)cc(Cl)c2)ccc2cccnc12]
AD4-13176
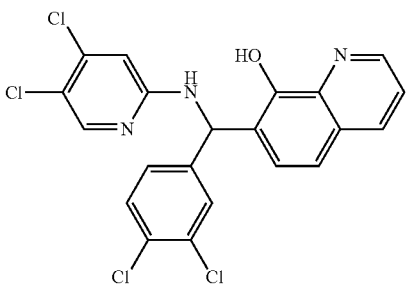 [SMILES: Oc1c(C(Nc2cc(Cl)c(Cl)cn2)c2ccc(Cl)c(Cl)c2)ccc2cccnc12]
AD4-13177
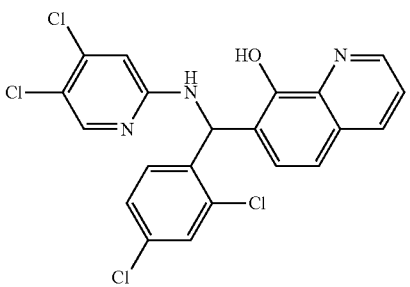 [SMILES: Oc1c(C(Nc2cc(Cl)c(Cl)cn2)c2ccc(Cl)cc2Cl)ccc2cccnc12]
AD4-13178
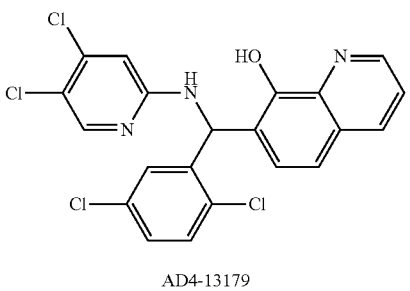
AD4-13179
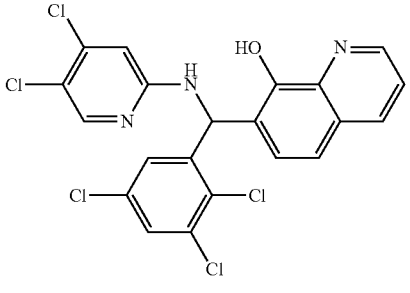 [SMILES: Oc1c(C(Nc2cc(Cl)c(Cl)cn2)c2cc(Cl)cc(Cl)c2Cl)ccc2cccnc12]
AD4-13180

TABLE 5-continued
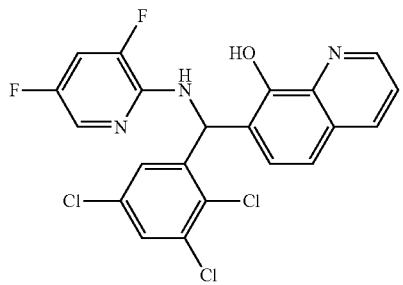 [SMILES: Oc1c(C(Nc2ncc(F)cc2F)c2cc(Cl)cc(Cl)c2Cl)ccc2cccnc12]
AD4-13181
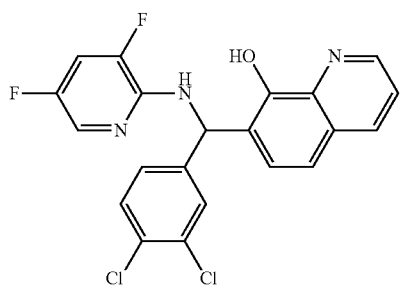 [SMILES: Oc1c(C(Nc2ncc(F)cc2F)c2ccc(Cl)c(Cl)c2)ccc2cccnc12]
AD4-13182
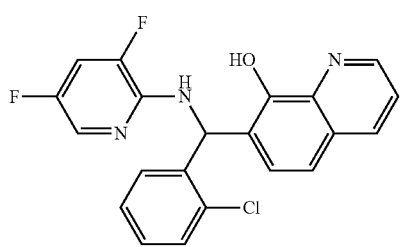
AD4-13183
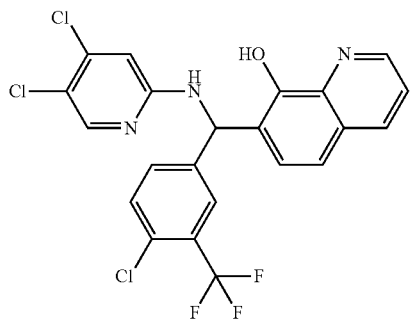
AD4-13184
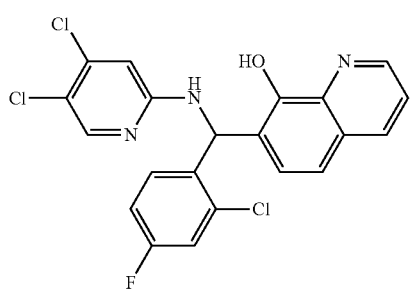
AD4-13185
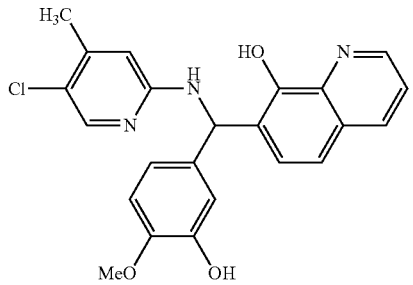
AD4-13186
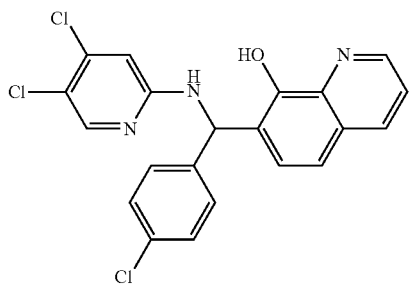 [SMILES: Oc1c(C(Nc2cc(Cl)c(Cl)cn2)c2ccc(Cl)cc2)ccc2cccnc12]
AD4-13187
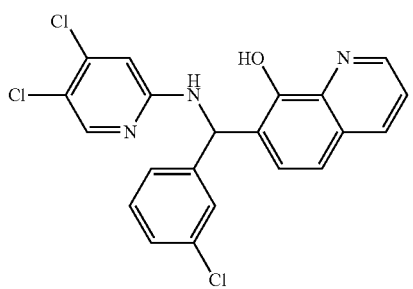 [SMILES: Oc1c(C(Nc2cc(Cl)c(Cl)cn2)c2cccc(Cl)c2)ccc2cccnc12]
AD4-13188
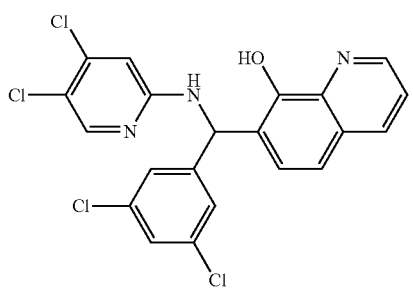 [SMILES: Oc1c(C(Nc2cc(Cl)c(Cl)cn2)c2cc(Cl)cc(Cl)c2)ccc2cccnc12]
AD4-13189
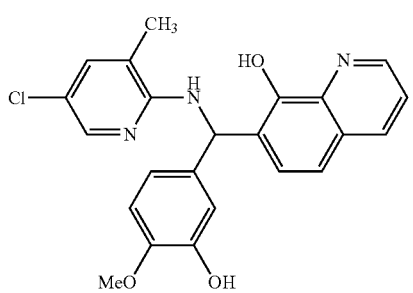 [SMILES: COc1ccc(C(Nc2ncc(Cl)cc2C)c2ccc3cccnc3c2O)cc1O]
AD4-13190

TABLE 5-continued
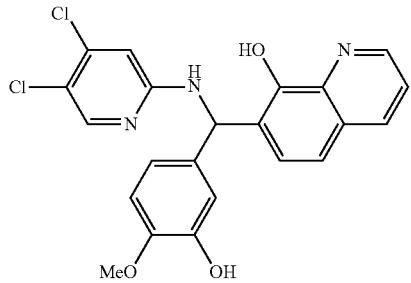 [SMILES: COc1ccc(C(Nc2cc(Cl)c(Cl)cn2)c2ccc3cccnc3c2O)cc1O]
AD4-13191
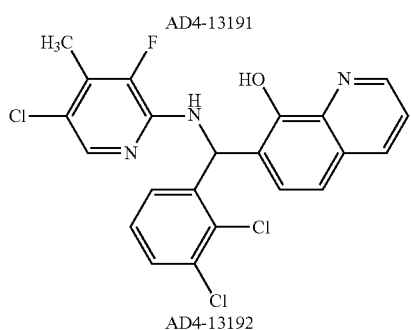
AD4-13192
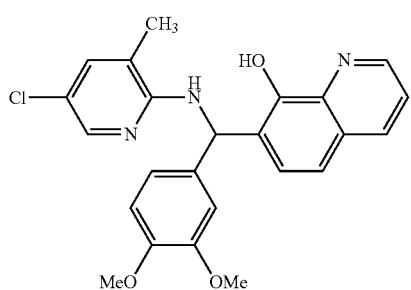 [SMILES: COc1ccc(C(Nc2ncc(Cl)cc2C)c2ccc3cccnc3c2O)cc1OC]
AD4-13193
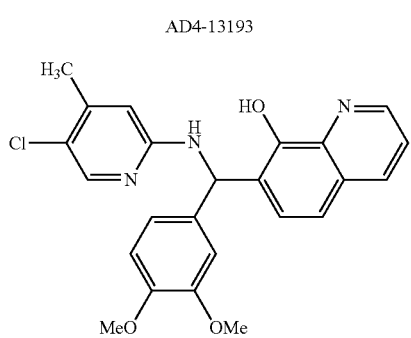
AD4-13194
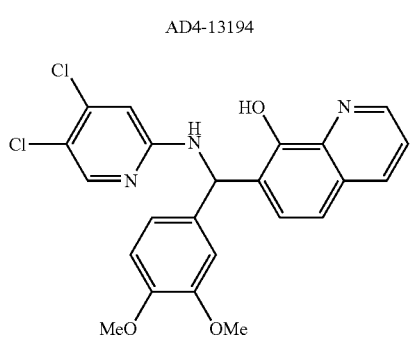
AD4-13195
TABLE 5-continued
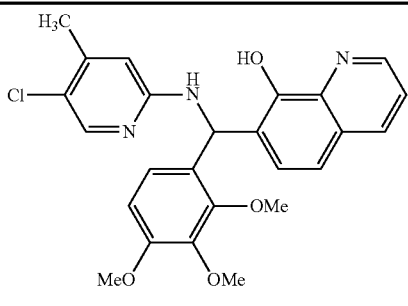
AD4-13196
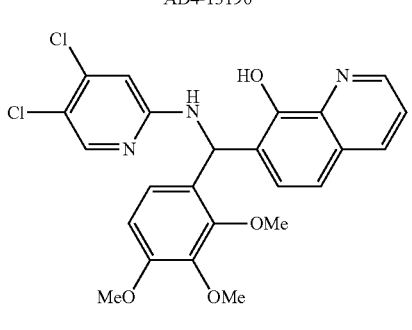
AD4-13197
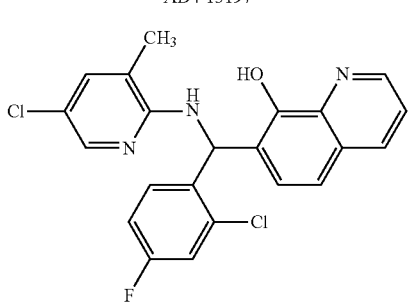
AD4-13198
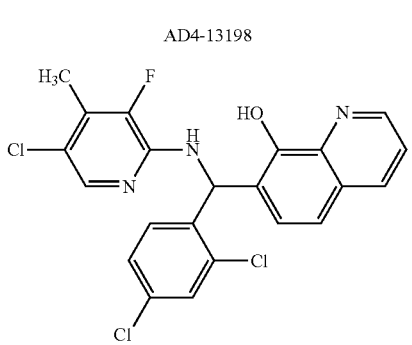
AD4-13199
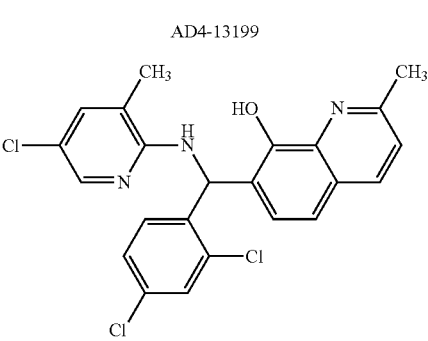
AD4-13200

TABLE 5-continued
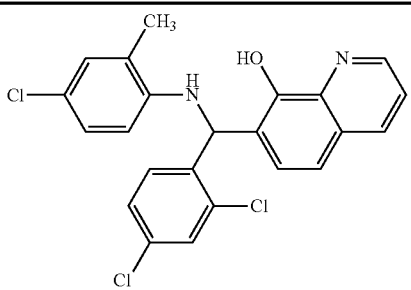
AD4-13201
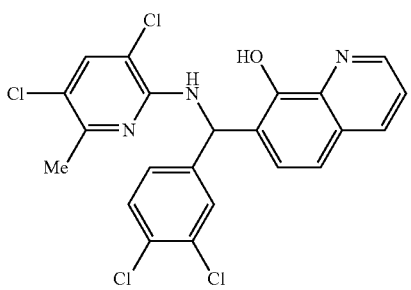 [SMILES: Cc1nc(NC(c2ccc(Cl)c(Cl)c2)c2ccc3cccnc3c2O)c(Cl)cc1Cl]
AD4-13202
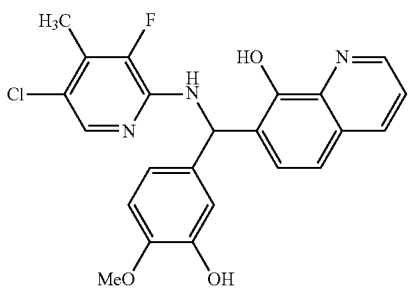 [SMILES: COc1ccc(C(Nc2ncc(Cl)c(C)c2F)c2ccc3cccnc3c2O)cc1O]
AD4-13203
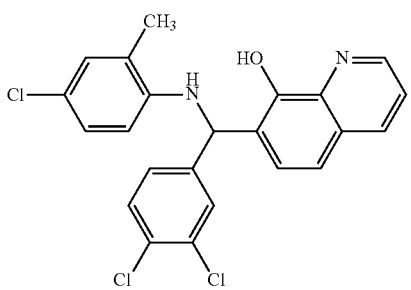 [SMILES: Cc1cc(Cl)ccc1NC(c1ccc(Cl)c(Cl)c1)c1ccc2cccnc2c1O]
AD4-13204
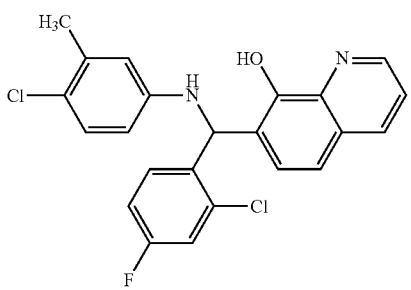
AD4-13205
TABLE 5-continued
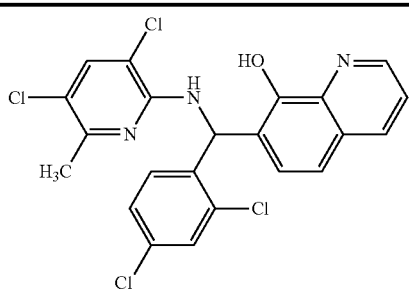
AD4-13206
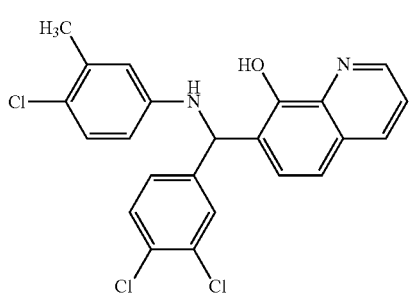 [SMILES: Cc1cc(NC(c2ccc(Cl)c(Cl)c2)c2ccc3cccnc3c2O)ccc1Cl]
AD4-13207
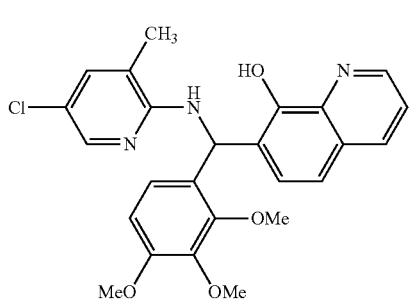 [SMILES: COc1ccc(C(Nc2ncc(Cl)cc2C)c2ccc3cccnc3c2O)c(OC)c1OC]
AD4-13208
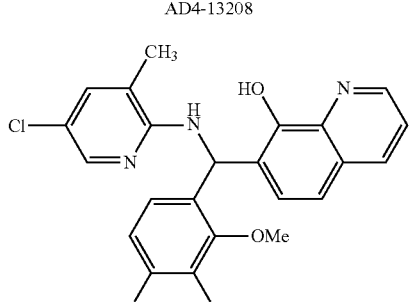
AD4-13208
AD4-13209

TABLE 5-continued
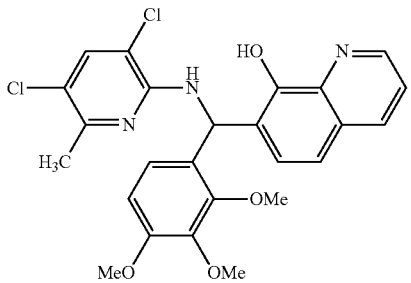 [SMILES: COc1ccc(C(Nc2nc(C)c(Cl)cc2Cl)c2ccc3cccnc3c2O)c(OC)c1OC]
AD4-13210
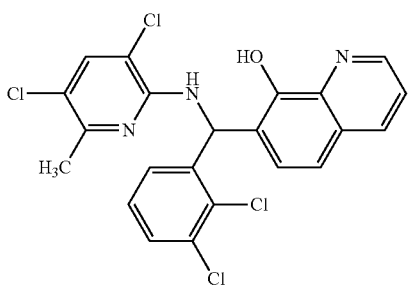 [SMILES: Cc1nc(NC(c2cccc(Cl)c2Cl)c2ccc3cccnc3c2O)c(Cl)cc1Cl]
AD4-13211
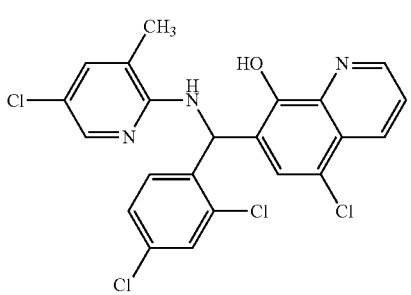 [SMILES: Cc1cc(Cl)cnc1NC(c1ccc(Cl)cc1Cl)c1cc(Cl)c2cccnc2c1O]
AD4-13212
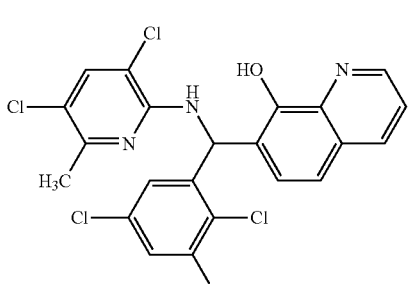
AD4-13213
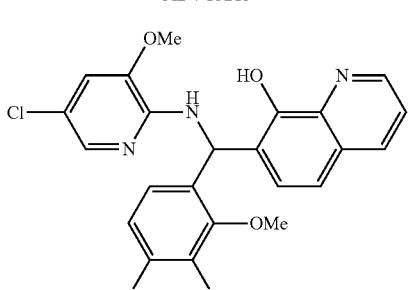
AD4-13214
TABLE 5-continued
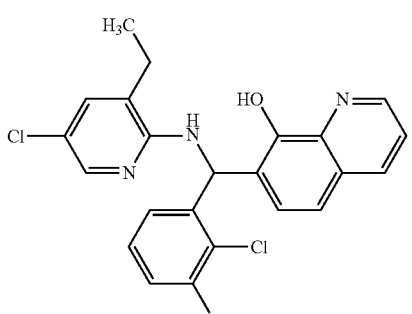
AD4-13215
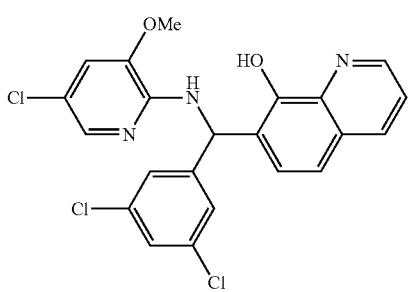
AD4-13216
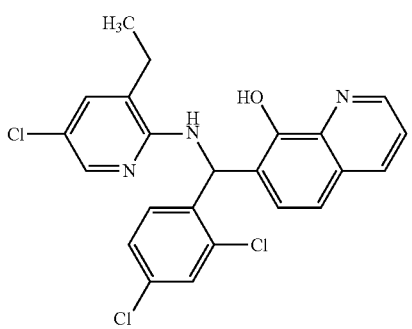
AD4-13217
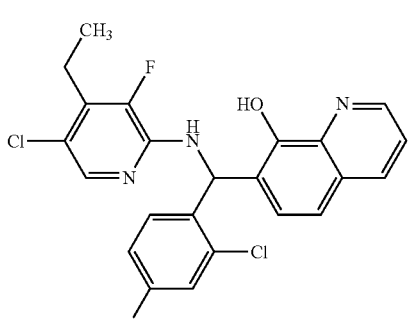
AD4-13218

TABLE 5-continued
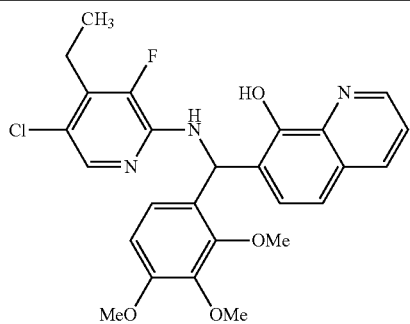
AD4-13219
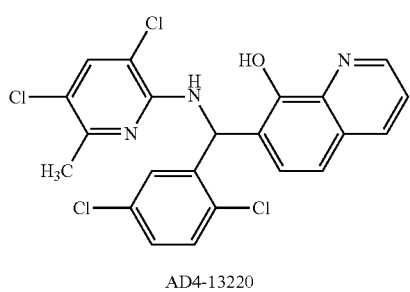 [SMILES: Cc1nc(NC(c2cc(Cl)cc(Cl)c2Cl)c2ccc3cccnc3c2O)c(Cl)cc1Cl]
AD4-13220
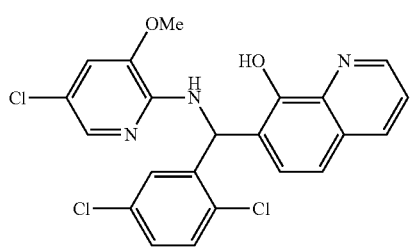 [SMILES: COc1cc(Cl)cnc1NC(c1cc(Cl)ccc1Cl)c1ccc2cccnc2c1O]
AD4-13221
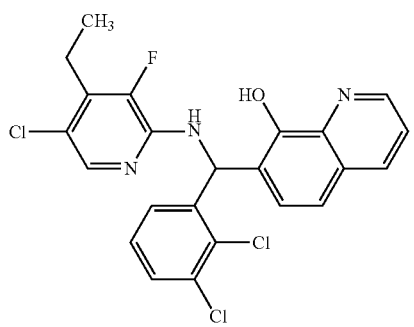 [SMILES: CCc1c(Cl)cnc(NC(c2cccc(Cl)c2Cl)c2ccc3cccnc3c2O)c1F]
AD4-13222
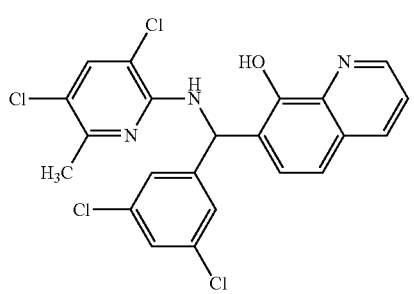 [SMILES: Cc1nc(NC(c2cc(Cl)cc(Cl)c2)c2ccc3cccnc3c2O)c(Cl)cc1Cl]
AD4-13223
TABLE 5-continued
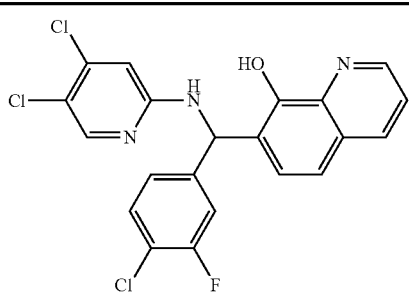
AD4-13224
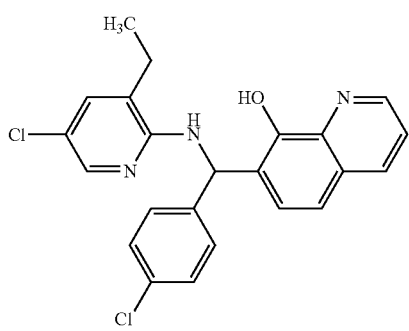 [SMILES: CCc1cc(Cl)cnc1NC(c1ccc(Cl)cc1)c1ccc2cccnc2c1O]
AD4-13225
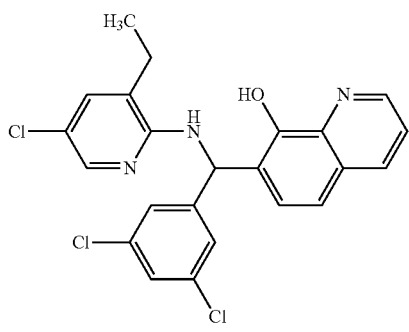 [SMILES: CCc1cc(Cl)cnc1NC(c1cc(Cl)cc(Cl)c1)c1ccc2cccnc2c1O]
AD4-13226
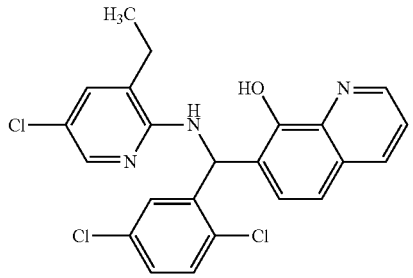 [SMILES: CCc1cc(Cl)cnc1NC(c1cc(Cl)ccc1Cl)c1ccc2cccnc2c1O]
AD4-13227

TABLE 5-continued
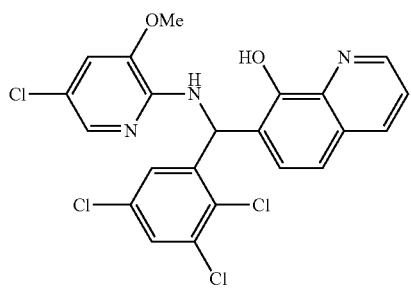
AD4-13228
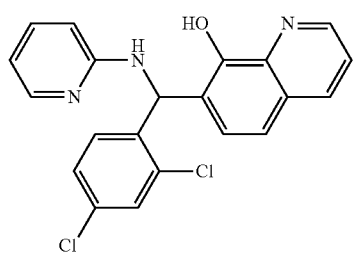 [SMILES: Oc1c(C(Nc2ccccn2)c2ccc(Cl)cc2Cl)ccc2cccnc12]
AD4-10484
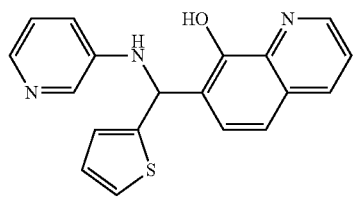 [SMILES: Oc1c(C(Nc2cccnc2)c2cccs2)ccc2cccnc12]
AD4-10315
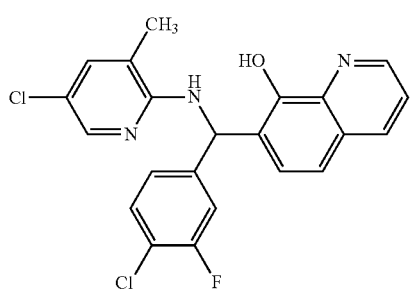
AD4-13229
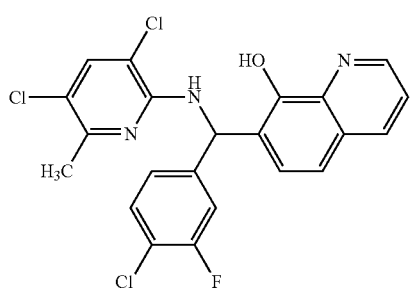 [SMILES: Cc1nc(NC(c2ccc(Cl)c(F)c2)c2ccc3cccnc3c2O)c(Cl)cc1Cl]
AD4-13230
TABLE 5-continued
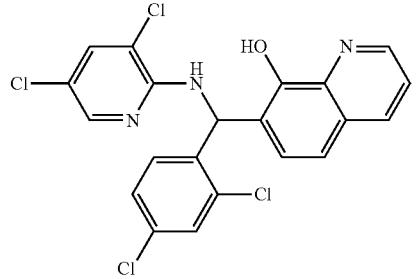 [SMILES: Oc1c(C(Nc2ncc(Cl)cc2Cl)c2ccc(Cl)cc2Cl)ccc2cccnc12]
AD4-13231
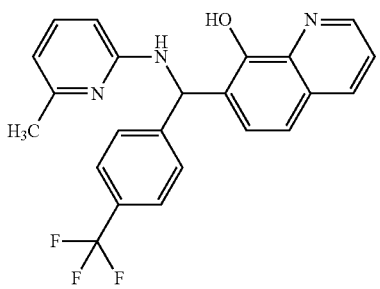 [SMILES: Cc1cccc(NC(c2ccc(C(F)(F)F)cc2)c2ccc3cccnc3c2O)n1]
AD4-10628
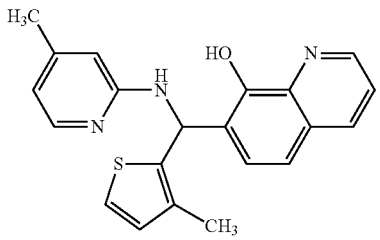
AD4-10963
In some embodiments, the compound(s) of Formula (2) excludes compound AD4-1505, Formula (1).
In some embodiments, the compound(s) of Formula (2) excludes one or more of the following compounds:
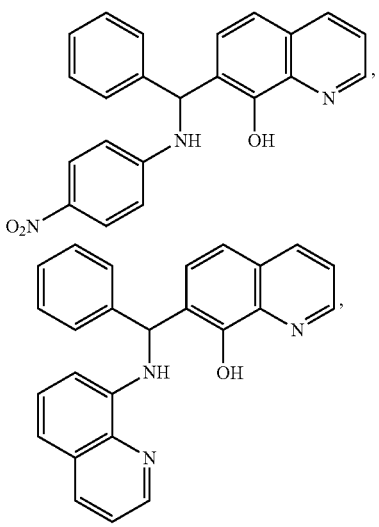

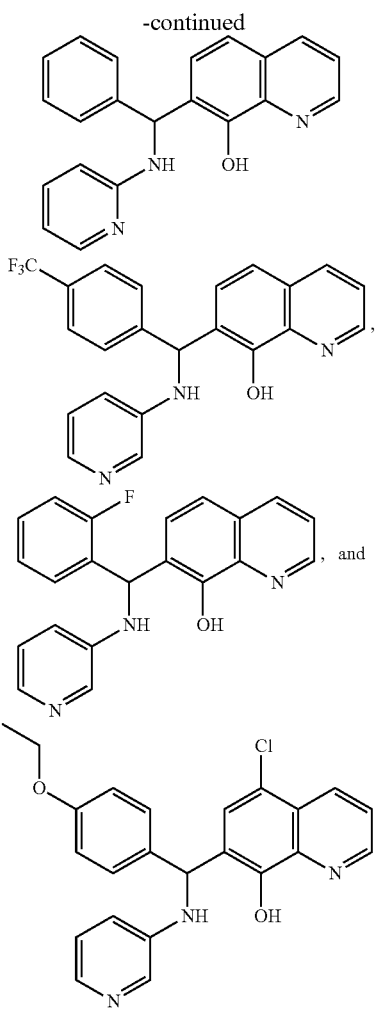

In some embodiments, for example methods of therapeutic treatment, the compound(s) of Formula (2) can include one or more of the above compounds.

Type B AD4-1505-like compounds.

An MDM2 inhibitor can be a compound according to Formula 10 (a Type B AD4-1505-like compound) as follows:

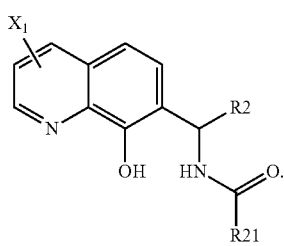

Formula (10)

In the above structure, $X^1$ and $R^2$ of Formula (10) are defined as above for structural sub-class Type A, Formula (2).

$R^{21}$ of Formula (10) can represent:

a lower alkyl group with one to 6 carbons (C-1 to C-6), straight chain, branched, or optionally containing unsaturation, cycloalkyl defined as five or six aliphatic ring (C-1 to C-6) optionally containing unsaturation;

an unsubstituted Phenyl ring or a Phenyl ring substituted at the 2-, 3-, 4-, 5- or 6-position with one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group as in the above definition), 2,3-Methylenedioxy or 3,4-Methylenedioxy group, Dialkylamino (—$NR_{13}R_{14}$, where $R_{13}$ and $R_{14}$ are independently selected from a Hydrogen atom or lower alkyl group as previously described); Trifluoromethyl, Trifluoromethoxy, Difluoromethoxy, 3,4-methylenedioxy, 2,3-methylenedioxy, Nitro or Halogen (F, Cl, Br, I);

an unsubstituted 2-Pyridyl ring or a 2-Pyridyl ring substituted at the 4- or 6-position of the pyridine ring with one or more of the following groups: lower alkyl group as defined above, cycloalkyl group as defined above;

an unsubstituted 3-Pyridyl ring or a 3-Pyridyl ring substituted at the 2-, 4- or 6-position of the pyridine ring with one or more of the following groups: lower alkyl group as defined above, cycloalkyl group as defined above;

an unsubstituted 4-Pyridyl ring or a 4-Pyridyl ring substituted at the 2- or 6-position of the pyridine ring with one or more of the following groups: lower alkyl group as defined above, cycloalkyl group as defined above; or a heteroaryl five or six membered ring containing from 1 to 4 N, O, or S atoms.

In some embodiments, the compound(s) are the enantiomeric isomers of Formula (10).

In some embodiments, the compound of Formula (10) is AD4-10950.

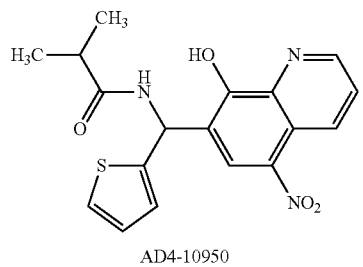 [SMILES: CC(C)C(=O)NC(c1cccs1)c1cc([N+](=O)[O-])c2cccnc2c1O]

AD4-10950

In some embodiments, the compound of Formula (10) is AD4-10960.

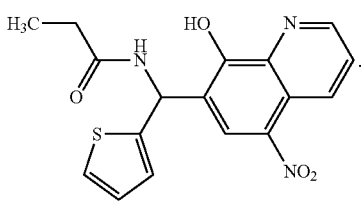

AD4-10960

In some embodiments, the compound(s) of Formula (10) excludes compound AD4-1505, Formula (1).

Type C AD4-1505-like

An MDM2 inhibitor can be a compound according to Formula 11 (a Type C AD4-1505-like compound) as follows:

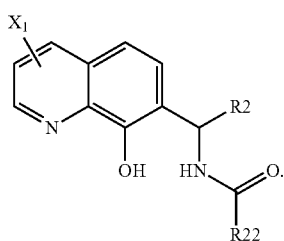

Formula (11)

In the above structure, $X^1$ and $R^2$ of Formula (11) are defined as above for structural sub-class Type A, Formula (2).

$R^{22}$ of Formula (11) can represent a lower alkyl group with one to 6 carbons (C-1 to C-6), straight chain, branched, optionally containing unsaturation, or substitution at the C-1 or C-2 carbons with one or more of the following substituents: an unsubstituted Phenyl ring or a Phenyl ring substituted at the 2-, 3-, 4-, 5- or 6-position with one or more of the following groups: lower alkyl defined as C-1 to C-4, straight chain, branched, or optionally containing unsaturation, cycloalkyl defined as C-1 to C-6 optionally containing unsaturation or one oxygen or nitrogen atom, Heteroaryl containing from 1 to 4 N, O, or S atoms, hydroxyl (—OH), Alkoxy (—OR$^{10}$ where $R^{10}$ is defined as a lower alkyl group or cycloalkyl group as in the above definition), Dialkylamino (—NR$_{13}$R$_{14}$, where $R_{13}$ and $R_{14}$ are independently selected from a Hydrogen atom or lower alkyl group as previously described); Trifluoromethyl, Trifluoromethoxy, Difluoromethoxy, or Halogen (F, Cl, Br, I).

A cycloalkyl is defined as five or six aliphatic ring (C-1 to C-6) optionally containing unsaturation or one oxygen or nitrogen atom.

In some embodiments, the compound(s) are the enantiomeric isomers of Formula (11).

In some embodiments, the compound of Formula (11) is AD4-10535.

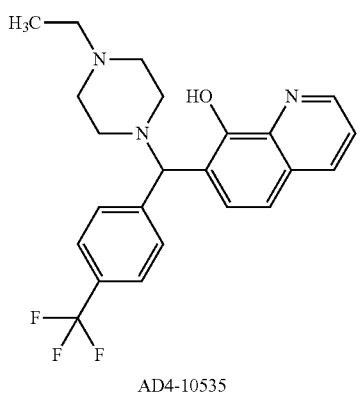 [SMILES: CCN1CCN(C(c2ccc(C(F)(F)F)cc2)c2ccc3cccnc3c2O)CC1]

AD4-10535

In some embodiments, the compound(s) of Formula (11) excludes compound AD4-1505, Formula (1).

Structure and Function.

An MDM2 inhibitor compound described herein can have structural features associated with one or more desired functions, such as stability, antiproliferative activity, or apoptotic activity.

It has been found that groups at the 5-position of the aminopyridine of compounds described herein provide analogs having increased stability (e.g., more stable toward liver microsome incubation). In some embodiments, a compound substituted at the 5-position of the aminopyridine can exhibit increased stability. For example, AD4-13053 and AD4-13041 (both having a chlorine atom at the 5-position of the aminopyridine) show increased stability over AD4-10628. In some embodiments, a compound substituted with a chlorine atom at the 5-position of the aminopyridine can exhibit increased stability increases stability.

It has been found that combinations of halogens and alkyl groups on the aminopyridine ring of compounds described herein provide compounds with increased antiproliferative activity. In some embodiments, a compound with the following aminopyridine ring substitutions provide increased antiproliferative activity: 3,5-diF; 3-F,5-CL,6-Me; 3-F,5-C$_{1-6}$-Me; 3-F,5-C$_{1-4}$-Et; and 3,5-diF,4-Me. In some embodiments, a compound with the following aminopyridine ring substitutions provide further increased antiproliferative activity: 3-Et,5-Cl; 3,5-diCl,6-Me; 3-F,5-C$_{1-4}$-Me; and 5-CF$_3$. In some embodiments, a compound with the following aminopyridine ring substitutions provide even further increased antiproliferative activity: 3-Me,5-Cl; 3,5-diCl; 4-Me,5-Cl; and 4,5-diCl.

It has been found that a chloro group at the 5-position of the aminopyridine ring and additional chloro or methyl groups at the 3- or 4-positions on the aminopyridine ring of compounds described herein provide compounds with increased apoptotic activity. In some embodiments, a compound with the following aminopyridine ring substitutions provide increased apoptotic activity: 3-Me,5-Cl; 3-F,5-C$_{1-4}$-Me; 4,5-diCl; and 3,5-diCl.

It has been found that groups at the 2- and 4-position of the benzene ring of compounds described herein provide analogs having increased stability (e.g., more stable toward liver microsome incubation). In some embodiments, a compound substituted at the 2- and 4-position of the benzene ring of compounds can exhibit increased stability. For example, AD4-13041, AD4-13042, AD4-13165, and AD4-13206 show increased stability. In some embodiments, a compound substituted with a halogen atom at the 2- or 4-position of the benzene ring of the aminopyridine can exhibit increased stability increases stability. For example, a compound substituted with a chlorine atom at the 2- and 4-position of the benzene ring of the aminopyridine can exhibit increased stability increases stability. As another example, a compound substituted with a fluorine atom at the 2- and 4-position of the benzene ring of the aminopyridine can exhibit increased stability increases stability. As another example, a compound substituted with a trifluoromethyl at the 4-position or a fluorine atom at the 2-position and a trifluoromethyl at the 4-position of the benzene ring of the aminopyridine can exhibit increased stability increases stability.

It has been found that combinations of halogens and trifluoromethyl groups on the benzene ring of compounds described herein provide compounds with increased antiproliferative activity. In some embodiments, a compound with the following benzene ring substitutions provide increased antiproliferative activity: 4-Cl; 2-F,4-CF$_3$; and 3-F,4-Cl. In some embodiments, a compound with the following benzene ring substitutions provide further increased antiproliferative activity: 2-F,4-Cl; 2,3-diCl; and 2,3,5-triCl. In some embodiments, a compound with the following benzene ring substitutions provide even further increased antiproliferative activity: 2,4-diCl; 3,4-diCl; and 3,5-diCl.

It has been found that a chloro group at the 4-position of the benzene ring and additional chloro or fluoro groups at the 2- or 3-positions on the benzene ring of compounds described herein provide compounds with increased apoptotic activity. In some embodiments, a compound with the following benzene ring substitutions provide increased apoptotic activity: 2,4-diCl (see e.g., AD4-13130, AD4-13178); and 2-Cl, 4-F (see e.g., AD4-13185).

Synthesis.

Synthesis of the above described compounds can be as described in U.S. application Ser. No. 12/986,146 and WO 2011/085126. In brief, an AD4-1505-like compound can be synthesized by reacting an amino pyridine intermediate compound, an aldehyde intermediate compound and a hydroxyquinoline, as further described in U.S. application Ser. No. 12/986,146 and WO 2011/085126. In some embodiments, the reaction can include combining the amino pyridine intermediate compound, the aldehyde intermediate compound and the hydroxyquinoline in ethanol (e.g., absolute ethanol).

In some embodiments, the MDM2 inhibitor is selected from one or more of the following compounds:

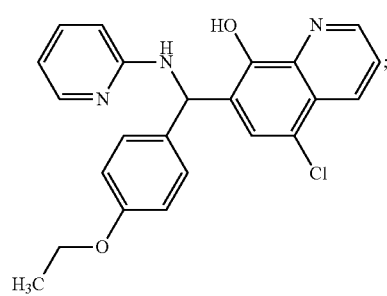
AD4-10953

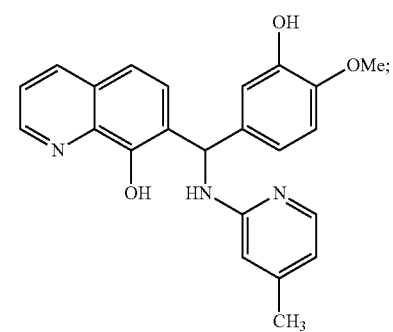
AD4-1505

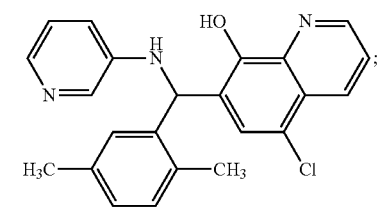
AD4-10944

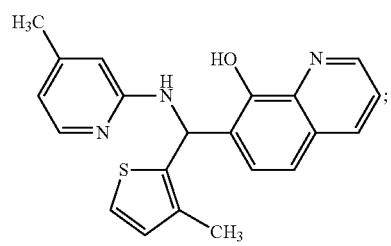
AD4-10963

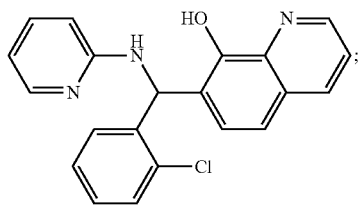
AD4-10482

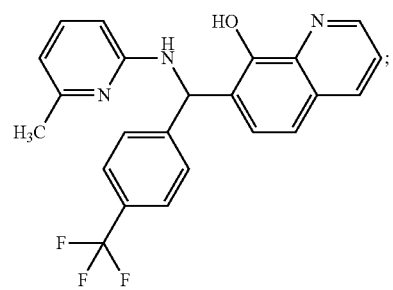
AD4-10483

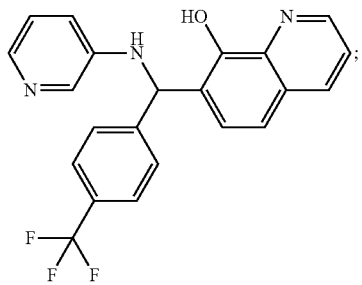
AD4-10942

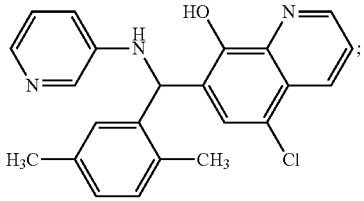
AD4-10944

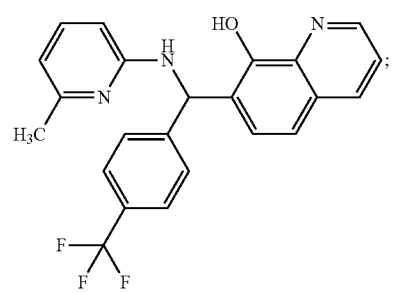
AD4-10628

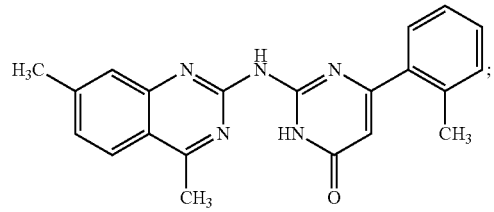
AD4-11511

-continued

AD4-13178

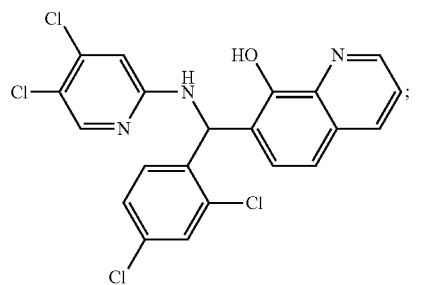

AD4-13130

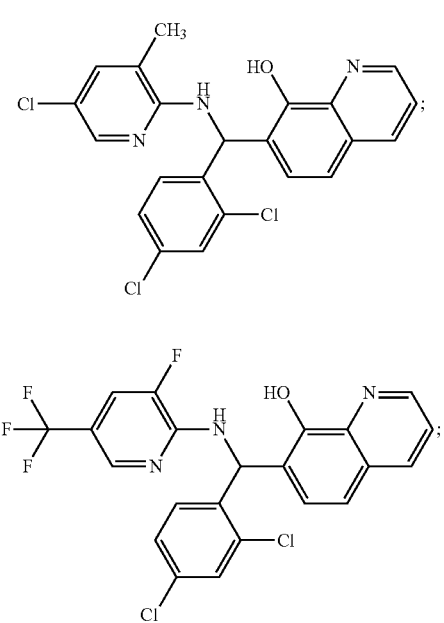

AD4-13165

AD4-13225

AD4-13229

; and

-continued

AD4-13243

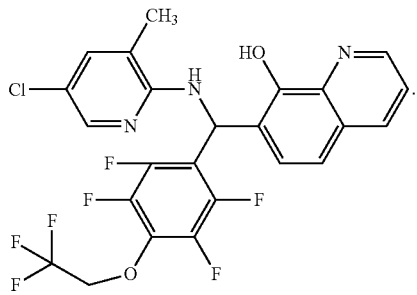

Chemical Definitions

The expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy).

The expression "cycloalkyl", unless specifically limited, denotes a $C_{3-10}$ cycloalkyl group (i.e., 3 to 10 ring carbon atoms), more suitably a $C_{3-8}$ cycloalkyl group, for example, a $C_{3-6}$ cycloalkyl group. Exemplary cycloalkyl groups include cyclopropyl, cyclobutyl, cyclopentyl, cyclohexyl, cycloheptyl and cyclooctyl. A preferred number of ring carbon atoms is three to six.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g., 1, 2, 3, or 4, suitably 1, 2 or 3) ring atoms are replaced by heteroatoms selected from N, S and O, or else a 5-membered aromatic ring containing one or more (e.g., 1, 2, 3, or 4, suitably 1, 2 or 3) ring atoms selected from N, S and O. Exemplary monocyclic heteroaryl groups having one heteroatom include: five membered rings (e.g., pyrrole, furan, thiophene); and six membered rings (e.g., pyridine, such as pyridin-2-yl, pyridin-3-yl and pyridin-4-yl). Exemplary monocyclic heteroaryl groups having two heteroatoms include: five membered rings (e.g., pyrazole, oxazole, isoxazole, thiazole, isothiazole, imidazole, such as imidazol-1-yl, imidazol-2-yl imidazol-4-yl); six membered rings (e.g., pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g., indol-6-yl), benzofuran, benzthiophene, quinoline, isoquinoline, indazole, benzimidazole, benzthiazole, quinazoline and purine.

A saturated group is generally understood as having no double or triple bonds. For example, in a saturated linear hydrocarbon, each carbon atom is attached to two hydrogen atoms, except those at the ends of the chain, which bear three hydrogen atoms. For example, an unsaturated hydrocarbon is generally understood as a carbon structure containing one or more double or triple bonds.

The term "halogen" or "halo" includes fluorine (F), chlorine (Cl) bromine (Br) or iodine (I).

The term "amino" refers to the group —NH$_2$.

All possible stereoisomers of the claimed compounds are included in the present disclosure. Where a compound described herein has at least one chiral center, it may accordingly exist as enantiomers. Where a compound possess two or more chiral centers it may additionally exist as diastereomers. It is to be understood that all such isomers and mixtures thereof are encompassed within the scope of the present disclosure.

In view of the close relationship between the free compounds and the compounds in the form of their salts, whenever a compound is referred to in this context, a corresponding salt is also intended, provided such is possible or appropriate under the circumstances. The pharmaceutically acceptable salt can take a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Alternatively it may take the form in which an acidic side chain forms a salt with a metal ion (e.g., sodium, potassium ions and the like) or other positive ion such as ammonium. All pharmaceutically acceptable acid addition salt forms of the compounds described herein are intended to be embraced by the scope of this disclosure.

Some of the crystalline forms of the compounds may exist in more than one polymorphic form and as such all forms are intended to be included in the present disclosure. In addition, some of the compounds may form solvates with water (i.e., hydrates) or common organic solvents, and such solvates are also intended to be encompassed within the scope of this disclosure. The compounds, including their salts, can also be obtained in the form of their hydrates, or include other solvents used for their crystallization.

The present disclosure further includes within its scope prodrugs of the compounds described herein. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject.

As used herein, the term "composition" is intended to encompass a product comprising a claimed compound(s) in a therapeutically effective amount, as well as any product which results, directly or indirectly, from combinations of the claimed compounds.

EGFR Inhibitor

As shown herein, administration of an EGFR inhibitor in combination with an MDM2 inhibitors can result in synergistic inhibition proliferation or increased death of cancer cells. An EGFR inhibitor can be an anti-proliferative or pro-apoptotic compound. An EGFR inhibitor can be selected so as to show a synergistic anti-proliferative or pro-apoptotic effect when co-administered with an MDM2 inhibitor (e.g., an inhibitor of p53 and MDM2 binding). Quantitative methods (e.g., protein phosphorylation detection) are known in the art to identify EGFR inhibitors and determine specificity and efficacy thereof (see e.g., Olive 2004 Expert Rev Proteomics 1(3), 327-341).

An EGFR inhibitor can be a monoclonal antibody, such cetuximab (tradename Erbitux, IMC-C225); panitumumab (tradename Vectibix, INN, ABX-EGF); nimotuzumab (tradenames BIOMab EGFR, Theracim, Theraloc, CIMAher); zalutumumab (proposed tradename HuMax-EGFr); or matuzumab (formerly EMD 7200). Erbitux is a humanized monoclonal antibody that binds to an extracellular epitope on EGFR. Erbitux blocks activation of the receptor by preventing both ligand binding and receptor dimerization. An EGFR inhibitor can be a protein, such as potato carboxypeptidase inhibitor (PCI).

An EGFR inhibitor can be a small molecule inhibitor, such as gefitinib (tradename Iressa, N-(3-chloro-4-fluoro-phenyl)-7-methoxy-6-(3-morpholin-4-ylpropoxy)quinazolin-4-amine); lapatinib (tradename Tykerb, N-[3-chloro-4-[(3-fluorophenyl)methoxy]phenyl]-6-[5-[(2-ethylsulfonylethylamino)methyl]-2-furyl]quinazolin-4-amine); erlotinib (tradename Tarceva, N-(3-ethynylphenyl)-6,7-bis(2-methoxyethoxy)quinazolin-4-amine). Tykerb, Iressa, and Tarceva are kinase inhibitors that block EGFR tyrosine kinase activity.

In some embodiments, an EGFR inhibitor can be an selected from lapatinib (tradename Tykerb), gefitinib (tradename Iressa), erlotinib (tradename Tarceva), or cetuximab (tradename Erbitux), or a combination thereof.

Combination Therapy

As shown herein, administration of MDM2 inhibitors in combination with EGFR inhibitor Tarceva can result in synergistic inhibition proliferation or increased death of cancer cells. Such a combinatorial therapeutic approach can overcome resistance to conventional EGFR inhibitors, which have been reported to occur in a significant number of patients.

An MDM2 inhibitor optionally used in combination with an EGFR inhibitor, such as Tarceva, can provide treatment for patients with developed resistance. Such therapy can treat a variety of cancers, including NSCLC, colon, pancreatic cancers and head and neck tumors, in patients where an EGFR inhibitor alone would not be effective.

Combinatorial treatment with an MDM2 inhibitor and an EGFR inhibitor can result in a synergistic anti-cancer effect or can overcome developed resistance. Such combinatorial therapy is especially useful in a subject having an inactivating P53 mutation, as described further herein. Synergistic effects or overcoming developed resistance can allow lower doses, significantly reducing therapy cost in a substantial patient population.

Formulation

Embodiments of the compositions of the invention include pharmaceutical formulations of the various compounds described herein.

The agents and compositions described herein can be formulated by any conventional manner using one or more pharmaceutically acceptable carriers or excipients as described in, for example, Remington's Pharmaceutical Sciences (A.R. Gennaro, Ed.), 21st edition, ISBN: 0781746736 (2005), incorporated herein by reference in its entirety. Such formulations will contain a therapeutically effective amount of a biologically active agent(s) described herein, preferably in purified form, together with a suitable amount of carrier so as to provide the form for proper administration to the subject.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Another aspect provided herein is a process of treating a proliferative disease, disorder, or condition with an MDM2 inhibitor and an EGFR inhibitor. Provided is a process of treating a proliferative disease, disorder, or condition in a subject in need administration of a therapeutically effective amount of an MDM2 inhibitor and an EGFR inhibitor, so as to increase apoptosis or decrease proliferation of cancer cells, tumors, or tissue. In various embodiments, a proliferative disease, disorder, or condition is associated with EGFR, MDM2, or p53. The therapeutic method can include administration of a therapeutically effective amount of an MDM2 inhibitor and an EGFR inhibitor, either as individual compositions or a jointly formulated composition.

An MDM2 inhibitor can be used with, or formulated with, known therapeutic compounds. Combination therapy is understood as a therapeutic regimen comprising, e.g., an MDM2 inhibitor described herein and a second agent. an MDM2 inhibitor and a second agent can be formulated for separate administration or may be formulated for administration together.

An MDM2 inhibitor can be combined with another antiproliferative compound, such as the EGFR kinase inhibitors, Tykerb, Iressa, and Tarceva, or Erbitux, a humanized monoclonal antibody to the EGF receptor, to produce a greater therapeutic effect than either agent alone. As shown herein, when MDM2 inhibitors were evaluated in a cell proliferation assay with EGFR inhibitors, the effect of the combination of agents to inhibit cell proliferation was greater than the effect of any of the agents alone. Specifically, compounds described herein were evaluated with Tykerb, Iressa, Tarceva or Erbitux at a fixed concentration ratio, which was ascertained from the results of dose-response curves of each agent alone.

An MDM2 inhibitor can be used or formulated with an EGFR inhibitor approved for treatment of an EGFR-related condition or disorder. For example, an MDM2 inhibitor can be used with or formulated with one or more of Tykerb, Iressa, Tarceva, or Erbitux. Tykerb, Iressa, and Tarceva are kinase inhibitors that block EGFR tyrosine kinase activity. Erbitux is a humanized monoclonal antibody that binds to an extracellular epitope on EGFR. Erbitux blocks activation of the receptor by preventing both ligand binding and receptor dimerization. Thus, an MDM2 inhibitor and known EGFR inhibitors, such as those described above, can act in a complementary or synergistic fashion.

Methods described herein are generally performed on a subject in need thereof. For example, a subject in need of the therapeutic methods described herein can be diagnosed with a proliferative disease, disorder, or condition, or at risk thereof. As another example, a subject in need of the therapeutic methods described herein can be diagnosed with a disease, disorder, or condition associated with EGFR, MDM2, or p53, or at risk thereof.

As another example, a subject in need of the therapeutic methods described herein can have, be diagnosed with, thought to have, or suspected of having an inactivating mutation or deletion in p53 (e.g., deletion or mutation of TP53 gene) (see Vassilev 2006 Trends in Molecular Medicine 13(1), 23-31). Determination of p53 status in tumor cells can be according to, for example, a DNA microarray-based p53 GeneChip (see Ahrendt et al. 1999 Proc Natl Acad Sci USA 96, 7382-7387).

As another example, a subject in need of the therapeutic methods described herein can have, be diagnosed with, thought to have, or suspected of having a defect in an upstream or a downstream component of the p53 pathway (see Vassilev 2006 Trends in Molecular Medicine 13(1), 23-31).

As another example, a subject in need of the therapeutic methods described herein can have, be diagnosed with, thought to have, or suspected of having aberrant MDM2 expression (see Vassilev 2006 Trends in Molecular Medicine 13(1), 23-31). As a further example, a subject in need of the therapeutic methods described herein can have, be diagnosed with, thought to have, or suspected of having overexpression of the MDM2 gene or overexpression of MDM2 protein without gene amplification, which may suppress p53 function (see Vassilev 2006 Trends in Molecular Medicine 13(1), 23-31).

As another example, a subject in need of the therapeutic methods described herein can have, be diagnosed with, thought to have, suspected of having, or be at risk for a resistance to a conventional therapeutic treatment, such as treatment with an EGFR inhibitor.

A determination of the need for treatment can be assessed by a history and physical exam consistent with the disease, disorder, or condition at issue. Diagnosis of the various conditions treatable by the methods described herein is within the skill of the art. The subject can be an animal subject, preferably a mammal, more preferably horses, cows, dogs, cats, sheep, pigs, mice, rats, monkeys, guinea pigs, and chickens, and most preferably a human.

Examples of proliferative diseases or conditions treatable with compositions described herein include, but are not limited to, cancer; blood vessel proliferative disorders; fibrotic disorders; mesangial cell proliferative disorders; psoriasis; actinic keratoses; seborrheic keratoses; warts; keloid scars; eczema; and hyperproliferative diseases caused by virus infections, such as papilloma virus infection.

Various compounds described herein can be effective for inhibiting EGFR, and thus, effective against diseases or conditions associated with EGFR, including, but not limited to, proliferative diseases. In some embodiments, the proliferative disease treated by a compound described herein is a condition caused by excessive growth of cancer or non-cancer cells that express a member of the EGFR family of receptors. The excess cells generated by a proliferative disease can express EGFR at normal levels or can overexpress EGFR. Particularly suitable diseases or conditions associated with EGFR can be those stimulated by a ligand of EGFR or mutations of such ligands. Examples of such ligands that stimulate EGFR include, but are not limited to, EGF, TGF-alpha, heparin-binding growth factor (HBGF), β-cellulin, and Cripto-1. Examples of proliferative disease associated with EGFR include, but are not limited to, cancer; blood vessel proliferative disorders; fibrotic disorders; mesangial cell proliferative disorders; psoriasis; actinic keratoses; seborrheic keratoses; warts; keloid scars; eczema; and hyperproliferative diseases caused by virus infections, such as papilloma virus infection.

Cancer, or neoplasia, refers generally to any malignant neoplasm or spontaneous growth or proliferation of cells. A subject having "cancer", for example, may have a leukemia, lymphoma, or other malignancy of blood cells. In certain embodiments, the subject methods are used to treat a solid tumor. Exemplary solid tumors include but are not limited to non small cell lung cancer (NSCLC), testicular cancer, lung cancer, ovarian cancer, uterine cancer, cervical cancer, pancreatic cancer, colorectal cancer (CRC), breast cancer, as well as prostate, gastric, skin, stomach, esophageal, and bladder cancer.

Treatment of cancer or treating a subject having cancer can include inhibition of replication of cancer cells, inhibition of spread of cancer, reduction in tumor size, lessening or reducing the number of cancerous cells in the body of a subject, or amelioration or alleviation of symptoms of cancer. A treatment can be considered therapeutic if there is a decrease in mortality or morbidity, and can be performed prophylactically, or therapeutically.

Methods described herein can be used to treat (e.g., reduce tumor size, decrease the vascularization, and/or increase the permeability of) an established tumor. An established tumor is generally understood as a solid tumor of sufficient size such that nutrients, e.g., oxygen, can no longer permeate to the center of the tumor from the subject's vasculature by osmosis and therefore the tumor requires its own vascular supply to receive nutrients. Methods described herein can be used to treat a solid tumor that is not quiescent and is actively undergoing exponential growth.

A therapeutic protocol can be modified according to permeability of a solid tumor. Permeability of a solid tumor generally refers to the permeability of a solid tumor to a therapeutic. A solid tumor may be said to be permeable to a therapeutic if the therapeutic is able to reach cells at the center of the tumor. An agent that increases the permeability of a tumor may for example, normalize, e.g., maintain, the vasculature of a solid tumor. Tumor vascularization or tumor permeability can be determined by a variety of methods known in the art, such as, e.g. by immunohistochemical analysis of biopsy specimens, or by imaging techniques, such as sonography of the tumor, computed tomography (CT) or magnetic resonance imaging (MRI) scans.

EGFR (Tuzi et al., 1991, Br. J. Cancer 63:227-233; Torp et al., 1992, APMIS 100:713-719) HER2/neu (Slamon et al., 1989, Science 244:707-712) and the PDGF-R (Kumabe et al., 1992, Oncogene 7:627-633) are known to be overexpressed in many tumors and/or persistently activated by autocrine loops. Overexpression of the receptor and autocrine loops have been demonstrated in most common and severe cancers (see e.g., Akbasak and Suner-Akbasak et al., 1992, J. Neurol. Sci. 111:119-133; Dickson et al., 1992, Cancer Treatment Res. 61:249-273; Korc et al., 1992, J. Clin. Invest. 90:1352-1360; Lee and Donoghue, 1992, J. Cell. Biol. 118:1057-1070). Overexpression of EGFR is known to be associated with cancers of the bladder, brain, head and neck, pancreas, lung, breast, ovary, colon, prostate, and kidney. (see e.g., Atalay et al., 2003, Ann. Oncology 14:1346-1363; Herbst and Shin, 2002, Cancer 94:1593-1611; Modjtahedi et al., 1996, Br. J. Cancer 73:228-235). Overexpression of EGFR can be correlated or associated with poor prognosis of the patients (see e.g., Herbst and Shin, 2002, Cancer 94:1593-1611; Modjtahedi et al., 1996, Br. J. Cancer 73:228-235). HER2 has been associated with breast, ovarian, gastric, lung, pancreas and bladder cancer.

An inhibitor compound described herein can be used therapeutically either as exogenous materials or as endogenous materials. Exogenous agents are those produced or manufactured outside of the body and administered to the body. Endogenous agents are those produced or manufactured inside the body by some type of device (biologic or other) for delivery to within or to other organs in the body.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of and MDM2 inhibitor and an EGFR inhibitor can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to provide a sufficient therapeutic outcome, as described further herein.

An effective amount of a compound described herein is generally that which can exhibit an anti-proliferative effect to an extent such as to ameliorate the treated condition. For example, an effective amount of a compound described herein may inhibit MDM2 or EGFR to an extent such as to ameliorate the treated condition. In some embodiments, an effective amount is that amount of therapy (or combination therapy) that is sufficient to affect a desired result on a cancerous cell or tumor, including, but not limited to, for example, reducing tumor size, reducing tumor volume, decreasing vascularization of a solid tumor, or increasing the permeability of a solid tumor to an agent, either in vitro or in vivo. In certain embodiments, an effective amount of therapy (or combination therapy) is the amount that results in a percent tumor inhibition of more than about 55%, about 60%, about 65%, about 70%, about 75%, about 80%, about 85%, about 90%, about 95%, about 99%, or about 100%. In certain embodiments, an effective amount of therapy (or combination therapy) is sufficient to achieve a desired clinical result, including but not limited to, for example, ameliorating disease, stabilizing a subject, preventing or delaying the development of, or progression of cancer in a subject. An effective amount of therapy (or combination therapy) can be determined based on one administration or repeated administration. Methods of detection and measurement of the indicators above are known to those of skill in the art. Such methods include, but are not limited to measuring reduction in tumor burden, reduction of tumor size, reduction of tumor volume, reduction in proliferation of secondary tumors, decreased solid tumor vascularization, expression of genes in tumor tissue, presence of biomarkers, lymph node involvement, histologic grade, and nuclear grade.

In some embodiments, tumor burden can be determined. Tumor burden, also referred to as tumor load, generally refers to a total amount of tumor material distributed throughout the body of a subject. Tumor burden can refer to a total number of cancer cells or a total size of tumor(s), throughout the body, including lymph nodes and bone barrow. Tumor burden can be determined by a variety of methods known in the art, such as, for example, by measuring the dimensions of tumor(s) upon removal from the subject, e.g., using calipers, or while in the body using imaging techniques, e.g., ultrasound, computed tomography (CT) or magnetic resonance imaging (MRI) scans. Tumor size can be determined, for example, by determining tumor weight or tumor volume.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Shargel (2004) Applied Biopharmaceutics & Pharmacokinetics, McGraw-Hill/Appleton & Lange, ISBN 0071375503). For example, it is well within the skill of the art to start doses of agents at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Administration of an MDM2 inhibitor or an EGFR inhibitor as described herein can occur as a single event, a periodic event, or over a time course of treatment. For example, agents can be administered daily, weekly, bi-weekly, or monthly. As another example, agents can be administered in multiple treatment sessions, such as 2 weeks on, 2 weeks off, and then repeated twice; or every 3rd day for 3 weeks. An MDM2 inhibitor and an EGFR inhibitor can have the same or different administration protocols. One of ordinary skill will understand these regimes to be exemplary and could design other suitable periodic regimes. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a disease, disorder, or condition associated with a target biomolecule for which the compound is specific.

A combination of an MDM2 inhibitor and an EGFR inhibitor can be administered simultaneously or sequentially with another agent, such as an antibiotic, an antiinflammatory, or another agent. Simultaneous administration can occur through administration of separate compositions, each containing one or more of an MDM2 inhibitor, an EGFR inhibitor, an antibiotic, an antiinflammatory, or another agent. Simultaneous administration can occur through administration of one composition containing three or more of an MDM2 inhibitor, an EGFR inhibitor, an antibiotic, an antiinflammatory, or another agent. A combination of an MDM2 inhibitor and an EGFR inhibitor can be administered sequentially with an antibiotic, an antiinflammatory, or another agent. For example, a combination of an MDM2 inhibitor and an EGFR inhibitor can be administered before or after administration of an antibiotic, an antiinflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition is administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening for an MDM2 inhibitor for use in the combinatorial therapy described herein. Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Preferably, initial screening is performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include the compositions of the present invention and, in certain embodiments, instructions for administration. Such kits can facilitate performance of the methods described herein, for example, treatment methodologies or screening methodologies. When supplied as a kit, the different components of the composition can be packaged in separate containers and admixed immediately before use. Components include, but are not limited to one or more compounds described herein, vectors, diagnostic reagents, assay reagents, and/or combinations thereof. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, or sterile saline, each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Alphascreen Measurement of p53/MDM2 Interaction (Using Truncated MDM2)

The following example describes an assay that measured the ability of compounds to inhibit the binding of p53 to MDM2 using the AlphaScreen assay technology (PerkinElmer). The following protocol is an adaptation of the method described by H. R. Lawrence et al. (Bioorg. Med. Chem. Lett. 19 (2009) 3756-3759). Recombinant, truncated, human, N-terminal GST-MDM2 (aa 1-150) was obtained from GeneScript. Wild-type, full length human N-terminal 6-his p53 was purchased from SignalChem.

Resulting in a final reaction volume of 24 µl PBS, 0.1% Tween-20, and 10% glycerol, 30 ng of MDM2 was added, followed by the addition of 10 of compound diluted in 100% DMSO that provided a final DMSO concentration of 4%. 30 ng of p53 was then added, mixed, and incubated at room temperature for 1 hour. Glutathione donor beads and Nickel acceptor beads (0.5 µg each; PerkinElmer) were added under subdued lighting conditions to a final reaction volume of 30 µl/well in a 96 well, ½ volume Proxima plate. The reaction was incubated at room temperature with shaking for 18 hrs in the dark. Analysis was then performed on a PerkinElmer EnSpire plate reader to determine the ability of compounds to inhibit the binding of p53 to MDM2.

Example 2

DNA Fragmentation, Measurement of Apoptosis

The following example describes an assay that measured the ability of compounds to induce DNA fragmentation, an indicator of cell apoptosis, using the Roche Cell Death Detection ELISA kit (Cat #11920 685 001). Methods are according to Example 1 unless otherwise specified.

Tissue Culture.

On day 1, seed A549 cells (10,000 cells/well at 200 µl/well) in tissue culture media (RPMI-1640 with 1% sodium pyruvate, 1% Pen-Strep, 1% L-Glutamine and 10% FBS) were placed in 96-well, tissue culture-treated plates. The plates were allowed to incubate overnight @ 37° C., 5% $CO_2$. On day 2, the media was removed from the plates and 160 µl media containing 5% FBS was added. 40 µl of media-containing test compound in 100% DMSO (prepared at 5× the dosing concentration) was added to the existing media resulting in a final DMSO concentration of 0.5%. Cells were incubated in the presence of a compound for 24 hrs @ 37° C., 5% $CO_2$.

DNA Fragmentation Assay.

After 24 hrs, the abovementioned plates were centrifuged at 200×g for 10 min. The media was removed by gently inverting the plate and disposing of the media onto a paper towel. The plates were tapped gently to remove excess media. 200 µl lysis buffer was added to each well, and mixed by shaking at 300 rpm. The plates were incubated at room temperature for 30 min. The plates were centrifuged at 200×g for 10 min and 20 µl of lysis supernatant was removed for use in ELISA analysis to detect cell death.

ELISA Analysis.

20 µl of the cell lysis supernatant was placed into streptavidin-coated plates with 20 µl positive control and 20 µl incubation buffer negative control. Add 80 µl Immunoreagent (for DNA fragment detection) to each well. The wells were covered with foil adhesive and shaken at 300 rpm for 2 h at room temperature. The supernatant solution was removed and the wells were washed 3 times with 300 µl incubation buffer. 100 µl of ABTS detection substrate was added to each well. The wells were incubated on a plate shaker at 250 rpm for approximately 10-20 min. 100 µl ABTS of stop buffer was then added. The absorbance was read at 400 and 492 nm on PolarStar plate reader. The absorbance measures the colored product spectrophotometrically, correlating with apoptosis.

Example 3

Proteome Profile, Measurement of Apoptosis

This example describes an assay that measured the relative expression levels of 35 apoptosis-related proteins in a single sample of whole cell extract. Methods are according to Examples 1-2 unless otherwise specified.

The protocol and reagents were purchased from R&D systems (Human apoptosis array kit; cat. #ARY009). The kit consisted of an antibody array spotted on nitrocellulose membranes with each specific antibody printed in duplicate. The detection antibodies were biotinylated so they could be used with a streptavidin-HRP conjugate designed for chemiluminescent imaging. The protocol was modified to utilize the LiCor infrared imaging technology by substituting an infrared 680 nm-tagged streptavidin.

Tissue Culture.

A549 NSCLC cells were seeded in 6 well tissue culture plates in RPMI-1640 supplemented with 5% FBS at a density of 1×10$^6$ cells/well, 2 ml/well and allowed to incubate overnight at 37° C., 5% $CO_2$, and 85% relative humidity.

The following day, two µl of compound dilutions in 100% DMSO were added to the appropriate wells resulting in a final concentration of 5 µM. The plates were then incubated for 6 hours at 37° C., 5% $CO_2$, and 85% relative humidity. Following incubation, the cells were washed with 2 ml of PBS, then lysed with 500 µl/well of Lysis buffer, supplemented with a 1/200 dilution of mammalian protease inhibitor cocktail (Sigma Aldrich). The plates were shaken for 30 min at room temperature, spun @ 14,000×g for 5 minutes. 250 µl of the supernatant was removed and added to 1.25 ml of Assay buffer 1. The supernatant and Assay buffer 1 were incubated with membranes overnight at room temperature with shaking.

The following day, the membranes were washed 3 times for 10 min each, with 1× wash buffer in individual 50 ml Falcon tubes at room temperature with rotation. The membranes were incubated with a 1/100 dilution of biotinylated detection antibodies for 3 hours at room temperature with shaking.

The membranes were washed, then incubated with a 1/1000 dilution of IR 680 nm-labeled streptavidin (LiCor) for 60 minutes with shaking in the dark. The membranes were again washed. Excess buffer was blotted from membranes, placed between two pieces of transparent plastic and imaged on the LiCor infrared imager. The LiCor Odyssey software is used to quantitate the pixel intensity of each spot in the array.

Example 4 p53 In-Cell Western, Measurement of Phosphorylated p53

This example describes an assay that measures the relative expression of human p53 and phospho-p53 (S15) in intact, formaldehyde-fixed, A549 NSCLC cells in a 96 well format. Methods are according to Examples 1-3 unless otherwise specified.

The procedure was adapted from a protocol suggested by LiCor Biosciences.

First, A549 NSCLC cells were seeded in black 96 well clear bottom tissue culture plates at a density of 25,000 cells/well, 200 µl/well, in RPMI-1640 supplemented with 5% FBS and allowed to incubate overnight at 37° C., 5% $CO_2$, and 85% relative humidity.

One µl of compound titrations in DMSO was added to each well and allowed to incubate for 8 and 30 hrs at 37° C., 5% $CO_2$, and 85% relative humidity for the determination of phospho p53(S15) and total p53, respectively. The media was removed, then 150 µl/well of 4% formaldehyde in PBS was added and incubated at room temperature for 30 min.

The wells were washed 5× for 5 minutes each, using 200 µl/well of 0.1% Triton X-100 in PBS with shaking to ensure permeation of the cells. 150 µl/well of Odyssey Blocking buffer (LiCor) was added to the wells and allowed to shake for 90 minutes at room temperature.

Next, the blocking buffer was removed, then incubated with 50 µl/well of a ¹/₂₅₀ dilution of either: (1) polyclonal Goat anti-human p53 or; (2) a ¹/₄₀ dilution of polyclonal Rbt anti human phospho (S15) p53 for 16 hrs at room temperature with shaking. The wells were washed 5× for 5 min each with 0.1% Tween-20 in PBS with shaking.

The cells were then incubated with 50 µl/well of either: (1) a ¹/₅₀₀₀ dilution of Donkey anti Goat IgG IR 800 nm or; (2) Goat anti-Rbt IR 800 nm containing a ¹/₆₀₀ dilution of DRAQ7 and ¹/₁₀₀₀ dilution of Sapphire 700 for 2-3 hrs at room temperature with shaking in the dark.

Finally, the wells were washed 5 times for 5 min each with 0.1% Tween-20 in PBS, with shaking in the dark. The plates were patted dry, then imaged using the LiCor infrared reader. Odyssey software was used to quantify the pixel intensity within each well.

Example 5

Measurement of Cell Proliferation Inhibition

This example describes an assay that measures the ability of compounds to inhibit the proliferation of cultured cells. This assay can also be used to assess whether combining two or more compounds produces additive, synergistic, or antagonistic effects on cell growth. Methods are according to Examples 1-4 unless otherwise specified.

On day 1, the cells were seeded at $10^3$ cells per well in 100 µl of complete media under standard conditions.

On day 2, the cells were washed and 100 µl serum free media was added. The cells were then incubated for at least 2 hours before the addition of compound(s). 20 µl of compound(s) was added to the respective wells and incubated at 37° C., 5% $CO_2$ for 72 hrs.

On day 5, 50 µl of the MTT dye solution was added to each well. The plates were incubated at 37° C., 5% $CO_2$ for 1 hr.

The media was then aspirated and the cells were resuspended in 1000 of DMSO. The plates were allowed to incubate for 5 min at room temperature with gentle shaking.

The absorbance in each well was determined at 560 nm using a Polarstar plate reader.

Example 6

Measurement of p53 Cellular Activity

This example describes an assay that measures the ability of compounds to stimulate p53-induced reporter gene activity. In order for p53 activity to be observed, the interaction of p53 with MDM2 must be inhibited. Methods are according to Examples 1-5 unless otherwise specified.

HEK293 cells were transiently transfected with the inducible p53-responsive firefly luciferase reporter and constitutively-expressing Renilla construct. After 16 hrs of transfection at 37° C., 5% $CO_2$, the transfection media was removed and 200 µl/well of assay media was added. The cells were then incubated for 8 hrs at 37° C., 5% $CO_2$.

1 ml of compound(s) was added to the cells and incubated for 16 hrs at 37° C. and 5% $CO_2$. The cells were carefully washed with 200 µl of PBS. 20 µl_of lysis buffer was then added to each well and incubated at room temperature for 15 minutes with shaking.

The lysis buffer supernatant was transferred to a white/opaque CoStar 96-well plate and 100 µl of firefly luceriferase assay substrate was added. The luminescence in each well was determined using a Polarstar plate reader.

100 µl of Stop and Glow reagent was added to each well, mixed, and the luminescence generated by the Renilla luciferase was determined using a Polarstar plate reader. The Renilla signal was used to normalize the transfection efficiency and cell viability.

Example 7

Caspase Activity

Measurement of Apoptosis

This example describes an assay that measures the ability of compounds to increase the activity of caspase ³/₇ activity. Methods are according to Examples 1-6 unless otherwise specified.

On day 1, 2000 cells were plated per well at 25 µl/well. The cells were incubated overnight @ 37° C., 5% $CO_2$.

On day 2, the cells were washed with PBS and 100 µl serum free media were added to the cells and incubated overnight.

On day 3, the cells were treated with the compound(s) diluted in 250/well of DMEM, with 1 mg/ml BSA. (no FBS). The plates were incubated for 5.5 hr at 37° C. The plates were removed from the incubator and allowed to equilibrate to room temperature for 30 min. 25 µl of Capsase Glo reagent was added to each well. The plates were covered and allowed to incubate at room temperature for 60 min. The luminescence in each well was determined using a plate reader.

Example 8

AD4 Compounds Inhibit Cell Proliferation and Demonstrate Synergistic Effect with Tarceva The following example provides preliminary assessment of the ability of selected AD4 compounds to inhibit EGF-mediated cell proliferation using the A431 cell proliferation assay and to demonstrated synergistic effects with Tarceva. Methods are according to Examples 1-7 unless otherwise specified. Compound structures are as disclosed in U.S. application Ser. No. 12/986,146 and WO 2011/085126.

The A431 cell line over-expresses the EGF receptor, and was utilized to assess the ability of AD4 compounds to inhibit EGF-mediated cell proliferation. A number of compounds inhibit cell proliferation in the A431 cell line, with $IC_{50}$ values ranging from 1.0-3.7 µM (see e.g., TABLE 6A). Tarceva inhibits cell proliferation with an $IC_{50}$ value of 0.8 µM (see e.g., TABLE 6A).

These results indicate that the AD4 compounds inhibit cell proliferation by interfering with a pathway that can potentiate the effects of the EGF inhibitor.

Furthermore, AD4 compounds demonstrated synergistic effects with Tarceva (see e.g., TABLE 6B). CI values <0.8 indicate a synergistic effect. Except for AD4-11511, all of the tested AD4 compounds produced synergy when combined with Tarceva. AD4-1505 and AD4-10963 produced the greatest effects.

These results indicate that the combination AD4/Tarceva compounds inhibit cell proliferation by interfering with a pathway that can potentiate the effects of the EGF receptor inhibitor.

TABLE 6

AD4 Compounds Inhibit Cell Proliferation and Demonstrate Synergistic Effect with Tarceva

| Compound | (A) A431 Cell Proliferation ($IC_{50}$, µM) | (B) A431 Cell Proliferation CI Value |
|---|---|---|
| Tarceva | 0.8 | |
| AD4-1505 | 3.7 | 0.45 |
| AD4-10963 | 3.4 | 0.43 |
| AD4-11511 | 1.0 | 0.89 |
| AD4-10482 | 3.6 | 0.54 |
| AD4-10483 | 1.2 | 0.70 |
| AD4-10942 | 3.2 | 0.60 |
| AD4-10944 | 1.8 | 0.52 |
| AD4-10628 | 1.0 | 0.76 |

Example 9

Further Studies Showing AD4 Compounds Inhibit Cell Proliferation and Demonstrate Synergistic Effect with Tarceva Based on preliminary results in Example 8, further testing was conducted. The following example describes the investigation of a compound's ability to inhibit cell proliferation in A431 cells, which overexpress EGF receptors. Methods are according to Examples 1-7 unless otherwise specified. Compound structures are as disclosed in U.S. application Ser. No. 12/986,146 and WO 2011/085126.

The results demonstrate that all AD4 compounds inhibit cell proliferation with an $IC_{50}$ value <10 µM, and six of the AD4 compounds inhibit cell proliferation with an $IC_{50}$ value <1 µM (see e.g., TABLE 7A). For comparison, Tarceva, an EGF receptor kinase inhibitor, produced an $IC_{50}$ value of 0.8 µM. The $IC_{50}$ values for AD4 compounds compared to Tarceva are on the same order of magnitude, displaying similar cell proliferation inhibition.

Furthermore, AD4 compounds in combination with Tarceva were shown to produce a synergistic effect. A number of compounds in the AD4 series were evaluated for their ability to produce synergistic effects (CI value <0.8) with Tarceva in the A431 cell proliferation assay (see Example 5).

Results show that most AD4 compounds tested in combination with Tarceva produce a CI value <0.8, which indicates synergy (see e.g., TABLE 7B).

These results indicate that the AD4 compounds inhibit cell proliferation by interfering with a pathway that can potentiate the effects of EGF receptor inhibitors.

TABLE 7

A431 Cell Proliferation

| Compound | (A) A431 Cell Proliferation ($IC_{50}$ Value, µM) | (B) A431 Cell Proliferation CI Value | (C) p53/MDM2 $IC_{50}$ Value (µM) |
|---|---|---|---|
| AD4-1505 | 3.7 | 0.29 | 3.6 |
| AD4-10315 | 3.5 | 0.79 | 1.5 |
| AD4-10381 | 0.62 | 0.62 | |
| AD4-10460 | 1.1 | 0.65 | |
| AD4-10482 | 3.6 | 0.89 | 18 |
| AD4-10483 | 1.2 | 0.75 | 4.6 |
| AD4-10484 | 1.3 | 0.97 | 7.4 |
| AD4-10628 | 1.0 | 0.57 | 4.0 |
| AD4-10942 | 3.2 | 0.57 | 18 |
| AD4-10944 | 1.8 | 0.79 | 17 |
| AD4-10945 | 2.7 | 0.65 | 4.6 |
| AD4-10963 | 3.4 | 0.63 | 2.0 |
| AD4-11511 | 1.0 | 0.89 | 4.3 |
| AD4-12632 | 6.0 | 0.29 | |
| AD4-12902 | 1.6 | 0.7 | 9.4 |
| AD4-12903 | 1.8 | 0.67 | 18 |
| AD4-12905 | 1.6 | 0.67 | 14 |
| AD4-12906 | 2.8 | 0.66 | 4.4 |
| AD4-12907 | 2.6 | 0.71 | 9.2 |
| AD4-12908 | 4.2 | 0.64 | |
| AD4-12909 | 6.7 | 0.54 | 4.2 |
| AD4-12910 | 1.8 | 0.69 | 7.5 |
| AD4-12911 | 1.4 | 0.76 | |
| AD4-12912 | 1.2 | 0.70 | |
| AD4-12914 | 1.4 | 0.74 | |
| AD4-12915 | 1.1 | 0.68 | |
| AD4-12917 | 1.6 | 0.54 | 3.6 |
| AD4-12918 | 2.2 | 0.65 | 5.2 |
| AD4-13023 | 1.8 | 0.74 | |
| AD4-13028 | 1.8 | 0.76 | |
| AD4-13029 | 1.8 | 0.83 | |
| AD4-13030 | 2.0 | 0.83 | |
| AD4-13031 | 1.6 | 0.74 | |
| AD4-13032 | 1.8 | 0.69 | |
| AD4-13033 | 1.9 | 0.80 | |
| AD4-13034 | 1.9 | 0.70 | |
| AD4-13041 | 2.0 | 0.69 | |
| AD4-13042 | 2.2 | 0.81 | |
| AD4-13043 | 2.1 | 0.81 | |
| AD4-13049 | 1.8 | 0.84 | |
| AD4-13051 | 1.6 | 0.72 | |
| AD4-13052 | 1.0 | 0.75 | |
| AD4-13053 | 1.4 | 0.78 | 12 |
| AD4-13054 | 2.1 | 0.61 | 9.0 |
| AD4-13055 | 1.5 | 0.75 | |
| AD4-13056 | 1.9 | 0.63 | |
| AD4-13057 | 1.1 | 0.83 | |
| AD4-13058 | 2.3 | 0.50 | 41 |
| AD4-13059 | 1.0 | 0.71 | |
| AD4-13060 | 1.5 | 0.76 | |
| AD4-13061 | 2.2 | 0.79 | |
| AD4-13062 | 2.5 | 0.57 | 44 |
| AD4-13063 | 4.4 | 0.77 | |
| AD4-13064 | 5.1 | 0.64 | |
| AD4-13065 | 4.6 | 0.61 | |
| AD4-13066 | 5.4 | 0.60 | |
| AD4-13067 | 1.8 | 0.63 | 8.0 |
| AD4-13068 | 5.8 | 0.68 | |
| AD4-13069 | 0.92 | 0.91 | |
| AD4-13070 | 1.9 | 0.65 | 8.0 |
| AD4-13071 | 3.5 | 0.70 | |
| AD4-13072 | 0.77 | 0.74 | |

TABLE 7-continued

A431 Cell Proliferation

| Compound | (A) A431 Cell Proliferation (IC$_{50}$Value, μM) | (B) A431 Cell Proliferation CI Value | (C) p53/MDM2 IC$_{50}$ Value (μM) |
|---|---|---|---|
| AD4-13073 | 1.6 | 0.85 | |
| AD4-13075 | 1.4 | 0.83 | |
| AD4-13076 | 1.4 | 0.71 | |
| AD4-13079 | 1.8 | 0.91 | |
| AD4-13080 | 2.5 | 0.68 | 6.0 |
| AD4-13082 | 1.9 | 0.90 | |
| AD4-13085 | 1.7 | 0.86 | |
| AD4-13086 | 1.5 | 0.80 | |
| AD4-13087 | 1.8 | 0.70 | |
| AD4-13088 | 1.5 | 0.76 | |
| AD4-13089 | 1.9 | 0.67 | 16 |
| AD4-13091 | 1.6 | 0.89 | |
| AD4-13092 | 1.5 | 0.79 | |
| AD4-13093 | 1.8 | 0.80 | |
| AD4-13094 | 1.3 | 0.76 | |
| AD4-13095 | 0.83 | 0.75 | |
| AD4-13096 | 3.0 | 0.61 | |
| AD4-13098 | 1.6 | 0.86 | |
| AD4-13099 | 2.1 | 0.61 | 10 |
| AD4-13101 | 2.1 | 0.66 | 20 |
| AD4-13102 | 1.4 | 0.75 | |
| AD4-13103 | 1.4 | 0.79 | |
| AD4-13104 | 2.8 | 0.67 | |
| AD4-13106 | 0.65 | 0.75 | |
| AD4-13107 | 1.7 | 0.64 | |
| AD4-13108 | 1.6 | 0.84 | |
| AD4-13109 | 1.5 | 0.88 | |
| AD4-13111 | 0.74 | 0.95 | |
| AD4-13112 | 2.1 | 0.73 | |
| AD4-13113 | 1.6 | 0.59 | 9.0 |
| AD4-13114 | 0.86 | 0.81 | |
| AD4-13115 | 1.6 | 0.74 | |
| AD4-13116 | 1.8 | 0.52 | 13 |
| AD4-13117 | 1.3 | 0.72 | |
| AD4-13118 | 1.5 | 0.60 | 24 |
| AD4-13121 | 1.9 | 0.75 | |
| AD4-13122 | 1.6 | 0.84 | |
| AD4-13123 | 1.3 | 0.71 | |
| AD4-13124 | 1.6 | 0.76 | |
| AD4-13125 | 1.7 | 0.70 | |
| AD4-13132 | 1.9 | 0.82 | |
| AD4-13139 | 1.4 | 0.75 | |
| AD4-13145 | 2.4 | 0.86 | |
| AD4-13177 | 2.0 | 0.9 | |
| AD4-13181 | 2.2 | 0.89 | |
| AD4-13193 | 4.7 | 0.92 | 24 |
| AD4-13194 | 5.3 | 0.97 | 26 |
| AD4-13195 | 5.8 | 0.81 | 25 |
| AD4-13196 | 5.0 | 0.69 | 10 |
| AD4-13197 | 3.4 | 0.63 | 18 |
| AD4-13198 | 3.0 | 0.87 | |
| AD4-13199 | 2.0 | 1.1 | |
| AD4-13200 | 1.5 | 0.97 | |
| AD4-13201 | 2.0 | 0.82 | |
| AD4-13202 | 1.8 | 0.87 | 10 |
| AD4-13243 | 2.2 | 0.56 | 8.5 |

Example 10

AD4 Compounds Inhibit Binding of p53 and MDM2

The following example demonstrates the ability of AD4 compounds to inhibit the binding of p53 and MDM2 in a biochemical assay. Methods are according to Examples 1-7 unless otherwise specified. Compound structures are as disclosed in U.S. application Ser. No. 12/986,146 and WO 2011/085126.

The results, which are summarized in TABLE 9, indicate that many of the AD4 compounds inhibit the binding of p53 and MDM2 with an IC$_{50}$ value <10 μM.

TABLE 9

Inhibition of p53/MDM2 Binding

| Compound | IC$_{50}$ Value (μM) |
|---|---|
| AD4-1505 | 4.2 |
| AD4-1969 | 26 |
| AD4-1973 | 4.6 |
| AD4-1976 | 5.6 |
| AD4-1978 | 16 |
| AD4-1991 | 5.0 |
| AD4-1997 | 8.0 |
| AD4-10013 | 16 |
| AD4-10016 | 5.5 |
| AD4-10017 | 3.5 |
| AD4-10028 | 7.1 |
| AD4-10031 | 6.3 |
| AD4-10037 | 7.6 |
| AD4-10051 | 19 |
| AD4-10052 | 14 |
| AD4-10053 | 40 |
| AD4-10055 | 19 |
| AD4-10068 | 18 |
| AD4-10086 | 5.7 |
| AD4-10087 | 7.7 |
| AD4-10101 | 7.0 |
| AD4-10108 | 10 |
| AD4-10143 | 21 |
| AD4-10144 | 5.8 |
| AD4-10315 | 1.5 |
| AD4-10427 | 21 |
| AD4-10430 | 5.0 |
| AD4-10460 | 6.2 |
| AD4-10466 | 13 |
| AD4-10482 | 18 |
| AD4-10483 | 4.6 |
| AD4-10484 | 7.4 |
| AD4-10487 | 21 |
| AD4-10546 | 3.1 |
| AD4-10547 | 4.3 |
| AD4-10550 | 9.3 |
| AD4-10551 | 10 |
| AD4-10602 | 18 |
| AD4-10628 | 4.0 |
| AD4-10936 | 16 |
| AD4-10938 | 55 |
| AD4-10939 | 8.6 |
| AD4-10942 | 18 |
| AD4-10944 | 17 |
| AD4-10945 | 4.6 |
| AD4-10952 | 0.33 |
| AD4-10955 | 20 |
| AD4-10957 | 61 |
| AD4-10958 | 10 |
| AD4-10959 | 3.4 |
| AD4-10960 | 17 |
| AD4-10961 | 0.92 |
| AD4-10963 | 2.0 |
| AD4-10968 | 5.4 |
| AD4-10974 | 25 |
| AD4-11000 | 17 |
| AD4-11017 | 3.4 |
| AD4-11042 | 18 |
| AD4-11057 | 20 |
| AD4-11072 | 49 |
| AD4-11073 | 20 |
| AD4-11102 | 17 |
| AD4-11103 | 4.2 |
| AD4-11105 | 21 |
| AD4-11151 | 4.3 |
| AD4-11153 | 3.4 |
| AD4-12902 | 9.4 |
| AD4-12903 | 18 |
| AD4-12905 | 14 |
| AD4-12906 | 4.4 |
| AD4-12907 | 9.2 |
| AD4-12909 | 4.2 |
| AD4-12910 | 7.5 |
| AD4-12917 | 3.6 |
| AD4-12918 | 5.2 |
| AD4-12941 | 9.5 |

TABLE 9-continued

Inhibition of p53/MDM2 Binding

| Compound | $IC_{50}$ Value (μM) |
|---|---|
| AD4-13053 | 12 |
| AD4-13054 | 9.0 |
| AD4-13058 | 41 |
| AD4-13062 | 44 |
| AD4-13067 | 8.0 |
| AD4-13070 | 8.0 |
| AD4-13080 | 6.0 |
| AD4-13089 | 16 |
| AD4-13099 | 10 |
| AD4-13101 | 20 |
| AD4-13113 | 9.0 |
| AD4-13116 | 13 |
| AD4-13118 | 24 |
| AD4-13193 | 24 |
| AD4-13194 | 26 |
| AD4-13195 | 26 |
| AD4-13196 | 10 |
| AD4-13197 | 18 |
| AD4-13202 | 10 |
| AD4-13208 | 13 |
| AD4-13210 | 20 |
| AD4-13214 | 20 |
| AD4-13219 | 30 |
| AD4-13243 | 8.5 |
| AD4-13256 | 9.7 |
| AD4-13262 | 5.0 |
| AD4-13263 | 4.7 |
| AD4-13264 | 4.5 |
| AD4-13265 | 3.4 |

Example 11

Combination AD4/Tarceva Inhibit Binding of p53 and MDM2

The following example demonstrates that combination AD4/Tarceva compounds that inhibit cell proliferation with synergistic effects also inhibit p53/MDM2 binding. Methods are according to Examples 1-7 unless otherwise specified. Compound structures are as disclosed in U.S. application Ser. No. 12/986,146 and WO 2011/085126.

The p53/MDM2 results for the compounds (equivalent compounds also evaluated in the A431 cell proliferation assay) are shown in TABLE 6C. These results show that compounds that inhibit cell proliferation in a cell line that over-expresses the EGF receptor, and that produce synergy with the EGF receptor inhibitor, Tarceva, are able to inhibit the binding of p53 and MDM2. As a result, compounds that inhibit the binding of p53 and MDM2 may provide a novel therapeutic approach for enhancing the activity of compounds that inhibit EGF receptor activity, such as Tarceva.

Example 12

AD4 Compounds Inhibit Binding of p53 with MDM2

The following example demonstrates a series of identified compounds that inhibit binding of p53 with MDM2. Methods are according to Examples 1-7 unless otherwise specified. The assay was performed as described in Example 1, except that recombinant full length human N-terminal GST-MDM2 was used and obtained from ABNOVA, and the wild type, full length human N-terminal 6-his p53 was purchased from Fisher Scientific Co. Compound structures are as disclosed in U.S. application Ser. No. 12/986,146 and WO 2011/085126.

The compounds studied in this example were AD4 1505, AD4 10963, AD4 11511, AD4 10482, AD4 10942, AD4 10944, and AD4 10628.

The most potent of the compounds studied in this example (see e.g. FIG. 1) were AD4-10963 and AD4-1505, which inhibit binding of the proteins with $EC_{50}$ values of 100 and 270 nM, respectively.

Example 13

AD4 Compounds Inhibit Interaction of p53 and MDM2

The following example demonstrates selected compounds that stimulated p53 reporter gene activity using the p53 reporter gene assay. Methods are according to Examples 1-7 unless otherwise specified. Compound structures are as disclosed in U.S. application Ser. No. 12/986,146 and WO 2011/085126.

Assessed compounds were chosen from those that potently inhibit activity in the p53/MDM2 biochemical assay.

At a concentration of 10 μM, AD4-1505, AD4-10953 and AD4-10944 stimulated p53 reporter gene activity by 42.5-, 9.7- and 7.5-fold, respectively. These results show that the compounds effectively inhibit the interaction of p53 and MDM2 in the cell.

Example 14

Correlation of p53/MDM2 Inhibition and Ability of AD4 Compounds to Produce Synergy with Tarceva A correlation plot shows the relationship between the ability of compounds to inhibit p53/MDM2 binding (see Example 13) and the ability to produce synergy with Tarceva (see Example 11) in the A431 cell proliferation assay. Compound structures are as disclosed in U.S. application Ser. No. 12/986,146 and WO 2011/085126.

Methods are according to Examples 1-7 unless otherwise specified.

Figure 3:
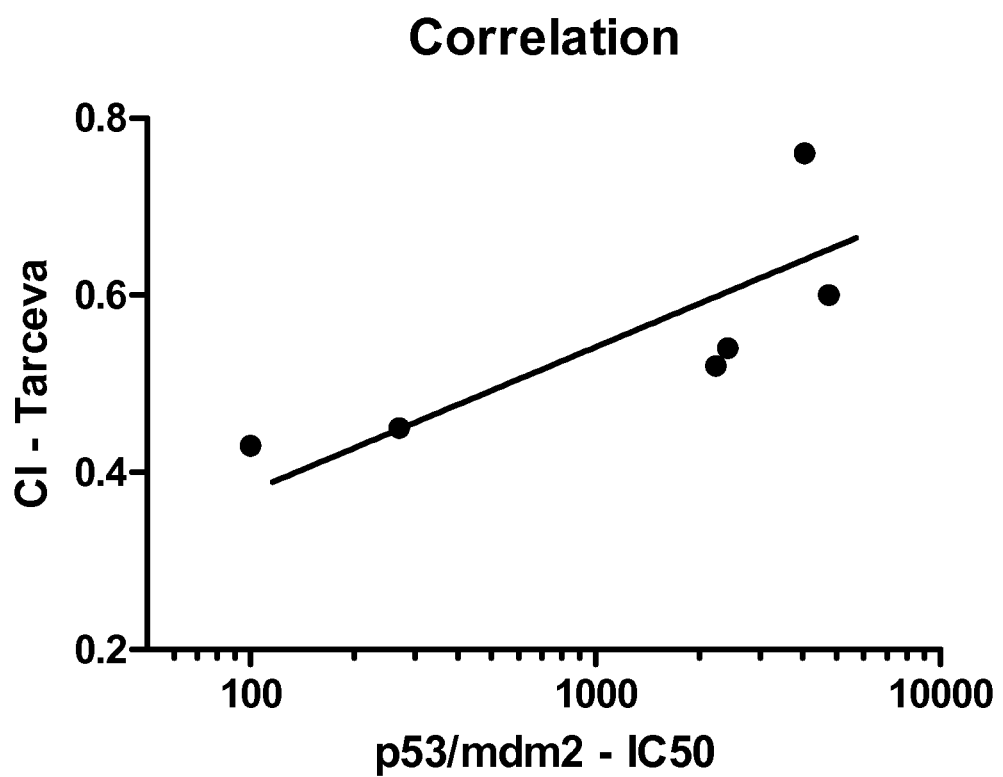
FIG. 3 is a line and scatter plot showing CI of Tarceva as a function of inhibition of p53/MDM2 binding (IC50), which demonstrates a correlation thereof.

A significant correlation was observed, with an Rsvalue=0.70 (p<0.05) (see e.g., FIG. 3).

Example 15

AD4 Compounds Induce Apoptosis as Measured by DNA Fragmentation

The following example demonstrates the ability of compounds to induce apoptosis evaluated by measuring the ability of compounds to induce DNA fragmentation. Methods are according to Examples 1-7 unless otherwise specified. Compound structures are as disclosed in U.S. application Ser. No. 12/986,146 and WO 2011/085126.

The ability of compounds to induce DNA fragmentation was evaluated as an additional measure of apoptosis in A549 lung cancer cells. The percent increase in DNA fragmentation produced by compounds at a concentration of 1 and 10 μM were compared to background, and to the response produced by 500 nM staurosporin.

The results for those compounds that produced a 20% increase in response relative to staurosporin are summarized in TABLE 10. A total of 28 compounds were found active.

TABLE 10

Induction of DNA Fragmentation in A549 Cells

| Compound | % Inc. over Background | | % Inc. Relative to Staurosporin (500 nM) | |
|---|---|---|---|---|
| | 1 µM | 10 µM | 1 µM | 10 µM |
| AD4-13123 | 366 | 476 | 40 | 51 |
| AD4-13130 | 565 | 614 | 58 | 65 |
| AD4-13134 | 573 | 469 | 56 | 46 |
| AD4-13147 | 406 | 462 | 48 | 52 |
| AD4-13161 | 254 | 688 | 25 | 68 |
| AD4-13164 | 390 | 579 | 38 | 55 |
| AD4-13165 | 172 | 582 | 24 | 74 |
| AD4-13172 | 355 | 782 | 32 | 70 |
| AD4-13178 | 395 | 581 | 47 | 68 |
| AD4-13185 | 285 | 576 | 32 | 62 |
| AD4-13187 | 388 | 543 | 47 | 62 |
| AD4-13224 | 296 | 662 | 25 | 59 |
| AD4-13225 | 508 | 458 | 48 | 42 |
| AD4-13229 | 531 | 667 | 68 | 84 |
| AD4-13243 | 551 | 716 | 70 | 91 |
| AD4-13260 | 148 | 310 | 26 | 52 |
| AD4-13261 | 184 | 538 | 20 | 63 |
| AD4-13277 | 484 | 962 | 50 | 103 |
| AD4-13290 | 172 | 637 | 22 | 79 |
| AD4-13292 | 200 | 854 | 20 | 86 |
| AD4-13299 | 592 | 688 | 54 | 62 |
| AD4-13303 | 403 | 828 | 35 | 69 |
| AD4-13309 | 444 | 858 | 38 | 71 |
| AD4-13311 | 506 | 877 | 42 | 72 |
| AD4-13314 | 803 | 735 | 66 | 62 |
| AD4-13316 | 486 | 902 | 40 | 75 |
| AD4-13317 | 757 | 892 | 57 | 67 |
| AD4-13323 | 621 | 661 | 57 | 60 |

Example 16

AD4 Compounds Induce Apoptosis as Measured by Increases DNA Fragmentation

The following example demonstrates the activity of compounds on p53 using a p53 In Cell Western assay. Methods are according to Examples 1-7 unless otherwise specified. Compound structures are as disclosed in U.S. application Ser. No. 12/986,146 and WO 2011/085126.

Using antibodies to total p53 or p53 phosphorylated at S15, the ability of compounds to alter the expression of total p53 in the cell, or the amount of phosphorylated S15 p53, were assessed.

The results indicate that AD4-13243, which increased DNA fragmentation and increased phosphorylated p53 in the proteome profile assay, significantly increased both total p53 expression and S15p-p53 at concentrations of about 1-3 µM. These results demonstrate that AD4-13243 can induce apoptosis by increasing the expression of p53.

Example 17

Combination AD4/Tarceva Synergistically Induce Apoptosis

The following example demonstrates the ability of compounds to induce apoptosis evaluated by the measurement of the ability of compounds to induce caspase 3/7 activity. Methods are according to Examples 1-7 unless otherwise specified. Compound structures are as disclosed in U.S. application Ser. No. 12/986,146 and WO 2011/085126.

In the caspase assay, which was conducted in A431 cells, compounds were evaluated for their ability to induce apoptosis, relative to the effect produced by 8 µM Tarceva alone. Additionally, cells were evaluated for synergistic effects of AD4 compounds in combination with Tarceva. The maximal effect (100%) was defined using 500 nM staurosporin (a compound commonly used to induce apoptosis, in vitro). Synergy was determined by determining whether the effect of the combination of Tarceva plus the AD4 compound produced a greater effect than the sum of the effect of Tarceva alone and the AD4 compound alone.

The results of these studies, which are summarized in TABLE 11, indicate that several compounds induce apoptosis as measured by an increase in caspase. Furthermore, these compounds produce synergy with Tarceva in this assay.

TABLE 11

Caspase 3/7 Activity

| Compound | % Inc. Relative to Tarceva | Synergy with Tarceva |
|---|---|---|
| AD4-13072 | 52% | Yes |
| AD4-13095 | 27% | Yes |
| AD4-13107 | 48% | Yes |
| AD4-13181 | 73% | Yes |
| AD4-13185 | 37% | Yes |
| AD4-13192 | 131% | Yes |
| AD4-13240 | 221% | Yes |
| AD4-13254 | 67% | Yes |

Example 18

Combination AD4/Tarceva Compounds Induce Apoptosis with no Measurable Cytotoxicity The following example demonstrates selected compounds that induce apoptosis. Methods are according to Examples 1-7 unless otherwise specified. Compound structures are as disclosed in U.S. application Ser. No. 12/986,146 and WO 2011/085126.

Compounds that inhibit proliferation of cancer cells produce a cytostatic effect, whereas compounds that induce apoptosis, or cell death, of cancer cells are cytotoxic.

Compounds were evaluated for induced apoptosis measured by the induction of caspase 3/7 activity (see Example 7). The ability of compounds to induce caspase 3/7 activity in A431 cells at a concentration of 10 µM is compared to the effect produced by 10 µM Tarceva.

The results (see e.g., TABLE 12) indicate that all of the compounds induce apoptosis, some of which (e.g. AD4-10628, AD4-10483 and AD4-11511) produce an effect equal to or greater than Tarceva. None of these compounds were found to produce measurable cytotoxicity in A431 cells.

TABLE 12

| Compound | % Increase Relative to Tarceva |
|---|---|
| AD4-1505 | 45% |
| AD4-10963 | 38% |
| AD4-11511 | 137% |
| AD4-10482 | 21% |
| AD4-10483 | 112% |
| AD4-10942 | 72% |
| AD4-10944 | 72% |
| AD4-10628 | 145% |

Figure 4:
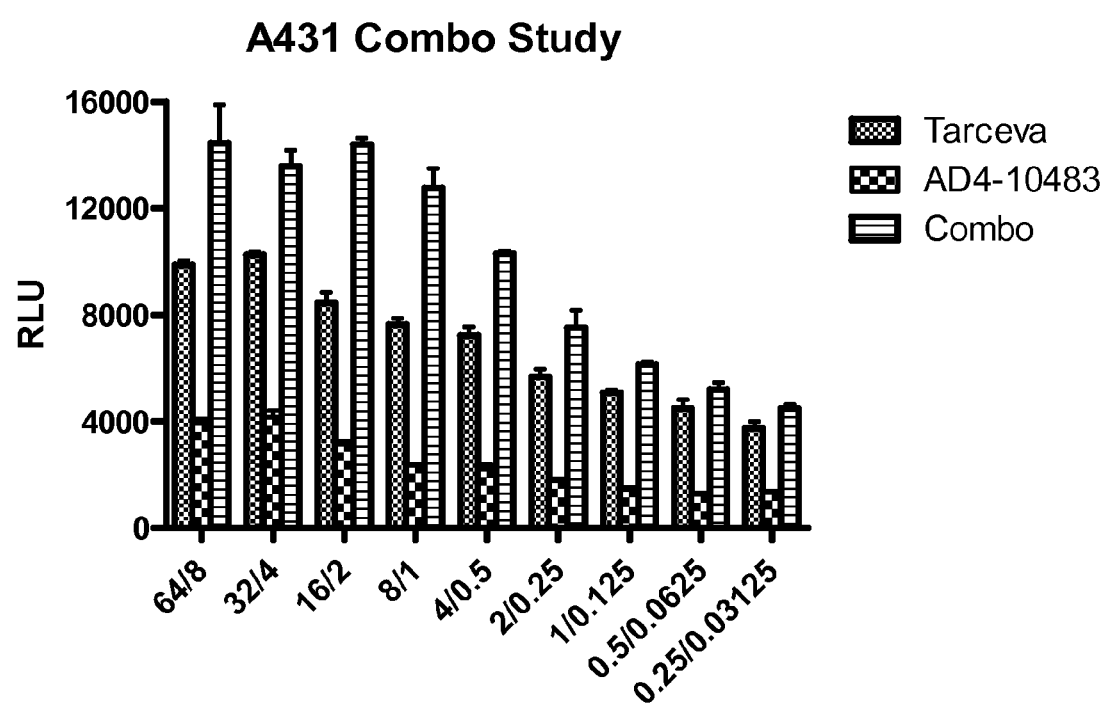
FIG. 4 is a bar graph showing the anti-proliferative effect in A431 cells of a Tarceva, AD4-10483, and a combination thereof.

The effect of the compounds when combined with Tarceva in the apoptosis assay was also evaluated (see e.g., FIG. 4). The combination of AD4-10483 and Tarceva demonstrated synergistic effects.

The data in this example shows that for all AD4 and Tarceva compounds studied, all induced apoptosis as individual compounds, however surprising results of synergy was observed when in combination.

Example 19

AD4 Increased Phosphorylated p53 Levels

Measured by Proteome Profiling

The following example demonstrates the mechanism of action of the current AD4 compound series. Methods are according to Examples 1-7 unless otherwise specified. Compound structures are as disclosed in U.S. application Ser. No. 12/986,146 and WO 2011/085126.

First, several compounds were evaluated in a proteome profiling array system containing antibodies to 35 apoptosis-related proteins. In this assay (see Example 3), the relative expression levels of these proteins in cell extracts are measured from treated and non-treated A549 cells.

The results from this study indicate that 6 AD4 compounds (AD4-13178, AD4-13225, AD4-13243, AD4-13130, AD4-13229 and AD4-13165) at a concentration of 5 μM, increased all three phosphorylated forms of p53, similar to nutlin, which inhibits the binding of p53 and MDM2.

Surprisingly, the pattern of expression produced by the AD4 compounds was different from nutlin (e.g., nutlin increased the expression of BAD and Bax, whereas the AD4 compounds did not), demonstrating that the AD4 compounds produce their effect on p53 by a different mechanism than nutlin. More importantly, all six of the compounds that increased the phosphorylated forms of p53 in the proteome profiler assay increased apoptosis, as measured by DNA fragmentation.

AD4 compounds in this example increased all three phosphorylated forms of p53 which inhibit the binding of p53 and MDM2.

What is claimed is:

1. A composition comprising:
   (a) an MDM2 inhibitor; and
   (b) an EGFR inhibitor,
   wherein the MDM2 inhibitor is a compound having a formula of

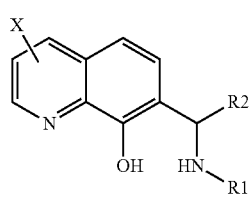

Formula (2)

or a stereoisomer or pharmaceutically acceptable salt thereof;

X is selected from the group consisting of hydrogen, 2-Methyl, 5-Chloro, 5-Nitro, and 6-Hydroxyl;

$R^1$ is selected from the group consisting of
   (i) a 2-Pyridyl ring of Formula (3)

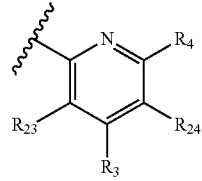

Formula (3)

wherein
   $R^{23}$ is selected from the group consisting of hydrogen; fluoro; chloro; trifluoromethyl; methyl; ethyl; and methoxy;
   $R^3$ is selected from the group consisting of hydrogen; fluoro; chloro; methyl; ethyl; methoxy; a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom;
   $R^{24}$ is selected from the group consisting of hydrogen; fluoro; chloro; and trifluoromethyl; and
   $R^4$ is selected from the group consisting of hydrogen; methyl; a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom;
(ii) a 3-Pyridyl ring of Formula (4)

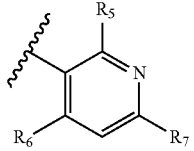

Formula (4)

wherein $R^5$, $R^6$, and $R^7$ are independently selected from the group consisting of hydrogen; trifluoromethyl; a straight chain or branched C-1 to C-4 lower alkyl optionally containing unsaturation, optionally containing one or more halogens; a C-1 to C-6 cycloalkyl optionally containing unsaturation or one oxygen or nitrogen atom; Aryl comprising a phenyl or heteroaryl containing from 1 to 4 N, O, or S atoms; and Alkoxy —$OR^{10}$ where $R^{10}$ is a straight chain or branched C-1 to C-4 lower alkyl optionally containing unsaturation, optionally containing one or more halogens; or a C-1 to C-6 cycloalkyl optionally containing unsaturation or one oxygen or nitrogen atom; and (iii) a 4-Pyridyl ring of Formula (5)

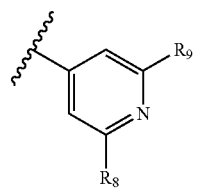

Formula (5)

wherein $R^8$ and $R^9$ are independently selected from the group consisting of a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom;

(iv) a phenyl ring substituted with one or more groups selected from a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl containing from 1 to 4 N, O, or S atoms; alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; trifluoromethyl; trifluoromethoxy; difluoromethoxy; 3,4-methylenedioxy; 2,3-methylenedioxy; nitro; and halogen; and (v) an unsubstituted heteroaryl five or six membered ring containing from 1 to 4 N, O, or S atoms;

(vi) a substituted heteroaryl five or six membered ring containing from 1 to 4 N, O, or S atoms substituted with one or more groups selected from the group consisting of straight chain or branched C-1 to C-4 lower alkyl optionally containing unsaturation; C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; and $R^2$ is selected from the group consisting of (i) an unsubstituted phenyl ring or a phenyl ring substituted at the 2-, 3-, 4-, 5- or 6-position with one or more groups independently selected from the group consisting of straight chain or branched C-1 to C-4 lower alkyl optionally containing unsaturation; C-1 to C-6 cycloalkyl optionally containing unsaturation or one oxygen or nitrogen atom; aryl comprising a phenyl or heteroaryl five or six membered ring containing from 1 to 4 N, O, or S atoms; hydroxy; alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; 2,3-methylenedioxy; 3,4-methylenedioxy; trifluoroethoxy; dialkylamino having formula —$NR_{13}R_{14}$ wherein $R_{13}$ and $R_{14}$ are independently selected from hydrogen; straight chain or branched C-1 to C-4 lower alkyl optionally containing unsaturation; trifluoromethyl; trifluoromethoxy; difluoromethoxy; 3,4-methylenedioxy; 2,3-methylenedioxy; nitro; and halogen;

(ii) a 2-thiophene ring of Formula (8) wherein $R^{15}$, $R^{16}$, and $R^{17}$ are independently selected from the group consisting of hydrogen; straight chain or branched C-1 to C-4 lower alkyl optionally containing unsaturation; C-1 to C-6 cycloalkyl optionally containing unsaturation or one oxygen or nitrogen atom; alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; dialkylamino; trifluoromethyl; difluoromethyl; trifluoromethoxy; and halogen

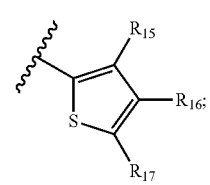

Formula (8)

(iii) a 3-thiophene ring of Formula (9) wherein $R^{18}$, $R^{19}$, and $R^{20}$ are independently selected from the group consisting of straight chain or branched C-1 to C-4 lower alkyl optionally containing unsaturation; C-1 to C-6 cycloalkyl optionally containing unsaturation or one oxygen or nitrogen atom; alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; dialkylamino; trifluoromethyl; difluoromethyl; trifluoromethoxy; and halogen

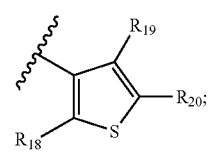

Formula (9)

(iv) an unsubstituted 2-Pyridyl ring or a 2-Pyridyl ring substituted at 4- or 6-position of the pyridine ring with one or more groups independently selected from the group consisting of straight chain or branched C-1 to C-4 lower alkyl optionally containing unsaturation and C-1 to C-6 cycloalkyl optionally containing unsaturation or one oxygen or nitrogen atom;

(v) an unsubstituted 3-Pyridyl ring or a 3-Pyridyl ring substituted at the 2-, 4- or 6-position of the pyridine ring with one or more groups independently selected from the group consisting of straight chain or branched C-1 to C-4 lower alkyl optionally containing unsaturation and C-1 to C-6 cycloalkyl optionally containing unsaturation or one oxygen or nitrogen atom; and (vi) an unsubstituted 4-Pyridyl ring or a 4-Pyridyl ring substituted at the 2- or 6-position of the pyridine ring with one or more groups independently selected from the group consisting of straight chain or branched C-1 to C-4 lower alkyl optionally containing unsaturation and C-1 to C-6 cycloalkyl optionally containing unsaturation or one oxygen or nitrogen atom; or a stereoisomer or pharmaceutically acceptable salt thereof.

2. The composition of claim 1, wherein a combination of the MDM2 inhibitor and the EGFR inhibitor results in a synergistic reduction in cell proliferation in a tumor of the subject or a synergistic increase in apoptosis in a tumor of the subject as compared to administration of either the MDM2 inhibitor or the EGFR inhibitor alone.

3. The composition of claim 1, wherein the EGFR inhibitor is selected from the group consisting of cetuximab, panitumumab, nimotuzumab, zalutumumab, matuzumab, potato carboxypeptidase inhibitor, gefitinib, lapatinib, and erlotinib, or a combination thereof.

4. The composition of claim 1, wherein the EGFR inhibitor is erlotinib.

5. The composition of claim 1, wherein the MDM2 inhibitor (i) inhibits MDM2 activity; (ii) increases phosphorylated p53; (iii) re-activates p53; or (iv) inhibits binding of p53 and MDM2; or a combination thereof.

6. The composition of claim 1, wherein the MDM2 inhibitor is a compound having a formula of:

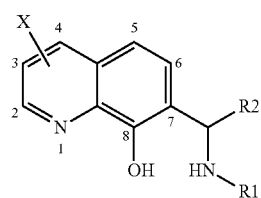

Formula (2)

or a stereoisomer or pharmaceutically acceptable salt thereof;
wherein,
X is selected from the group consisting of hydrogen, 2-Methyl, and 5-Chloro,
$R^1$ is selected from the group consisting of
  (i) a 2-Pyridyl ring of Formula (3)

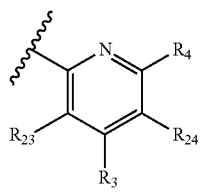

Formula (3)

wherein
  $R^{23}$ is selected from the group consisting of hydrogen; fluoro; chloro; and methyl;
  $R^3$ is selected from the group consisting of hydrogen; chloro; and methyl;
  $R^{24}$ is selected from the group consisting of hydrogen; fluoro; chloro; and trifluoromethyl; and
  $R^4$ is selected from the group consisting of hydrogen; and methyl;

(ii) a 3-Pyridyl ring of Formula (4)

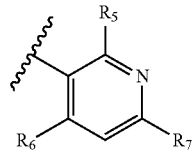

Formula (4)

wherein $R^5$, $R^6$, and $R^7$ are independently selected from the group consisting of hydrogen and trifluoromethyl and $R^2$ is selected from the group consisting of
  (i) an unsubstituted phenyl ring or a phenyl ring substituted at the 2-, 3-, 4-, 5- or 6-position with one or more groups independently selected from the group consisting of methyl; methoxy; ethoxy; trifluoroethoxy; trifluoromethyl; hydroxy; trifluoromethoxy; Cl; and F;
  (ii) a 2-thiophene ring of Formula (8) wherein $R^{15}$, $R^{16}$, and $R^{17}$ are independently selected from the group consisting of hydrogen and methyl

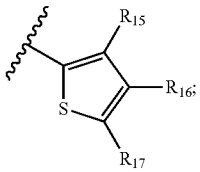

Formula (8)

or a stereoisomer or pharmaceutically acceptable salt thereof.

7. The composition of claim 1, wherein the MDM2 inhibitor comprises a compound selected from the group consisting of:

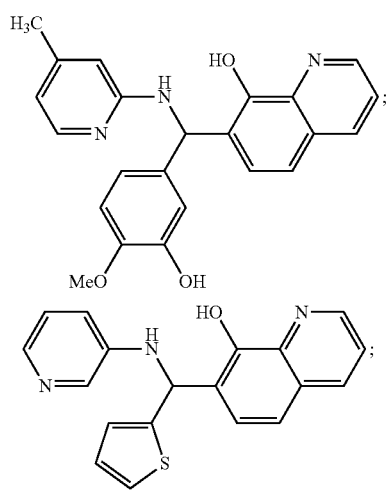

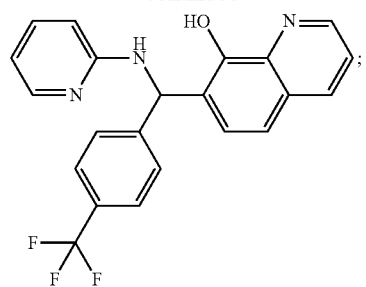
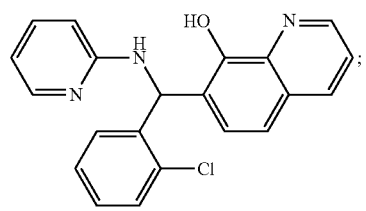
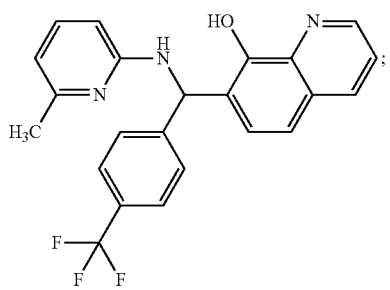
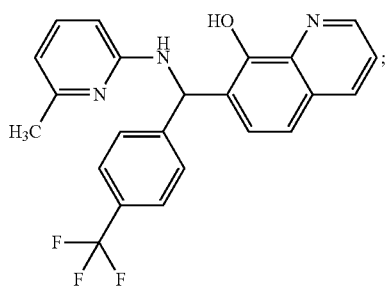
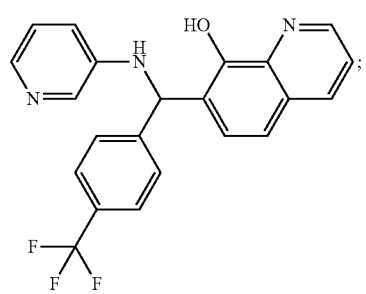
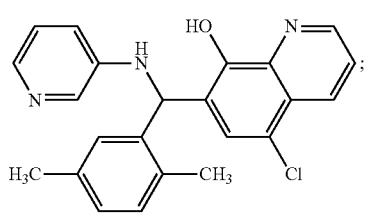
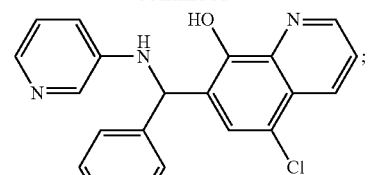
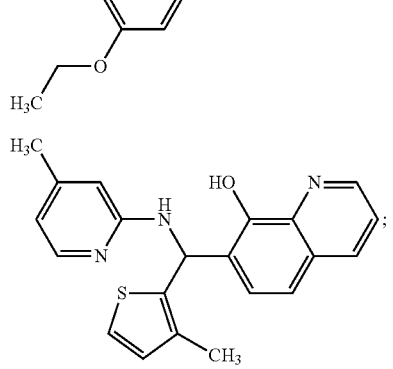
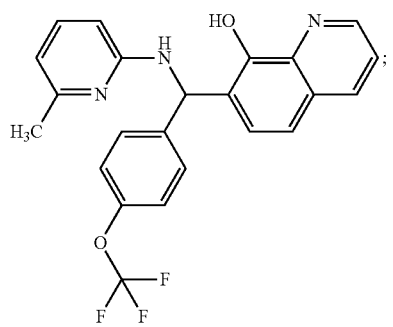
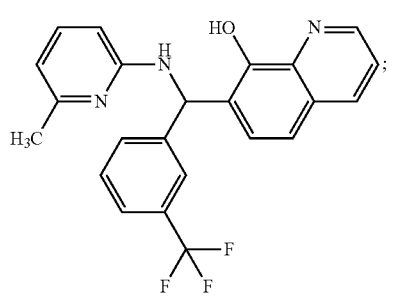
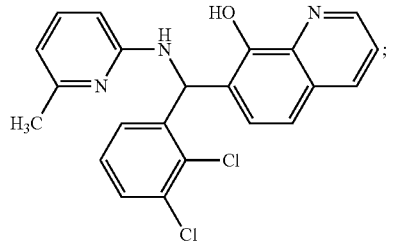
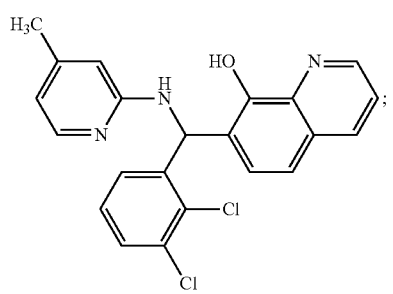

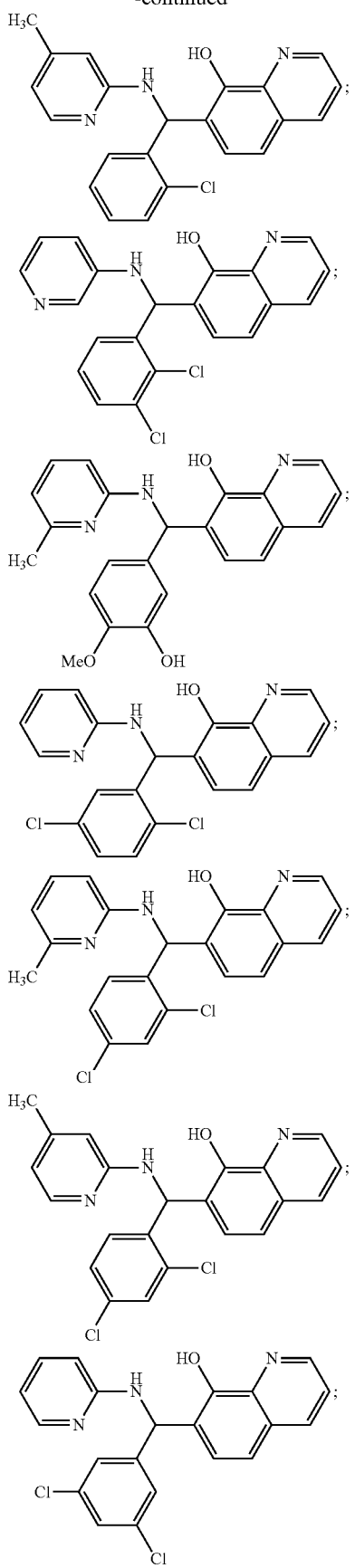
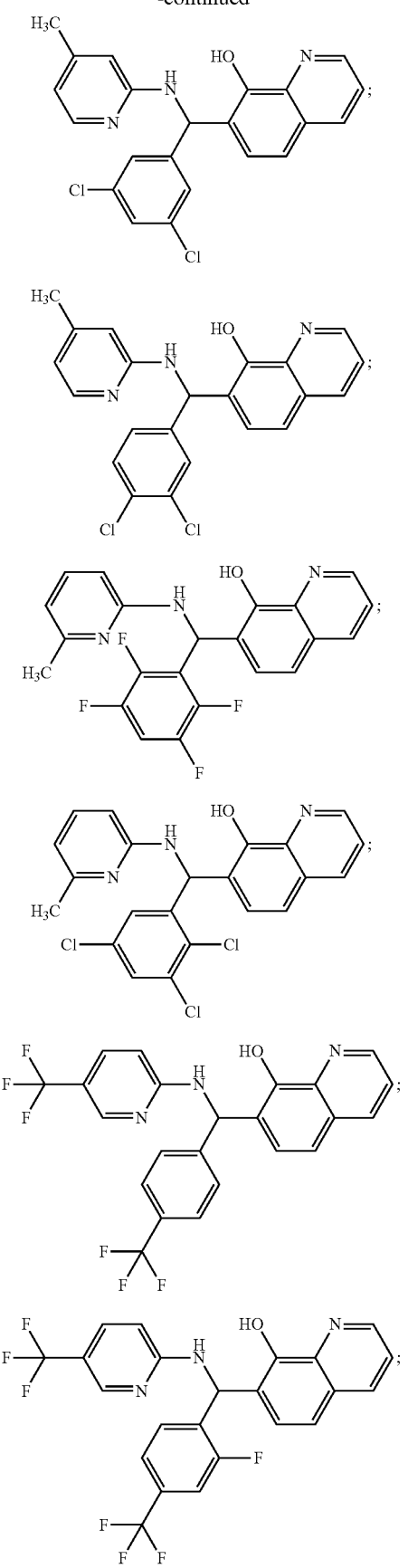

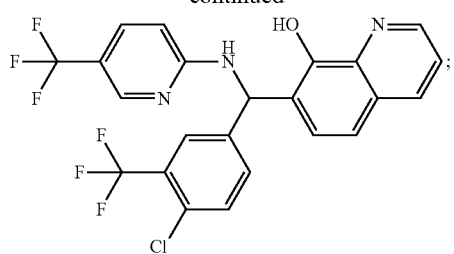
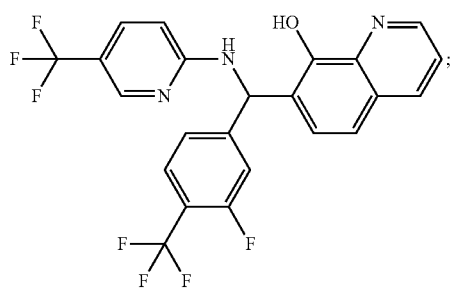
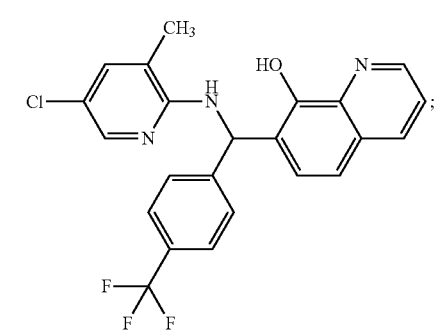
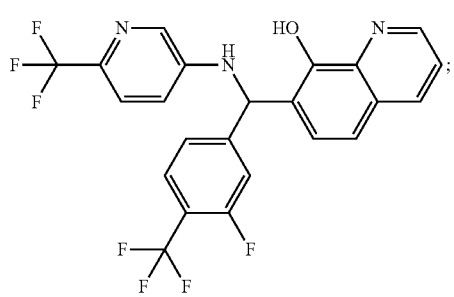
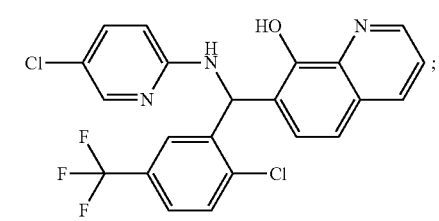
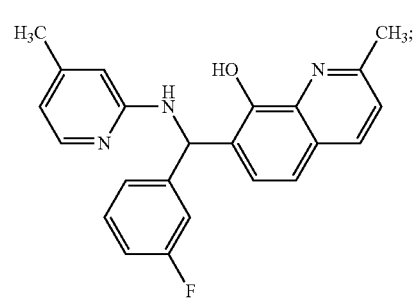
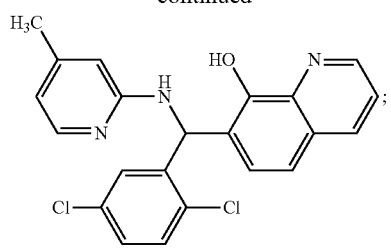
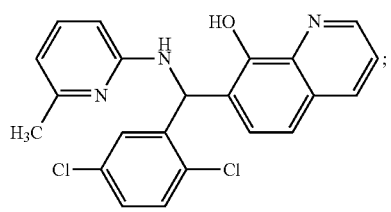
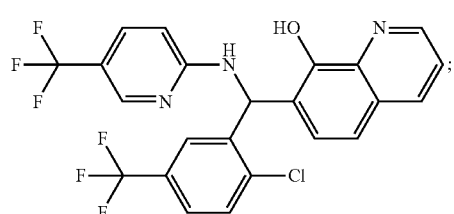
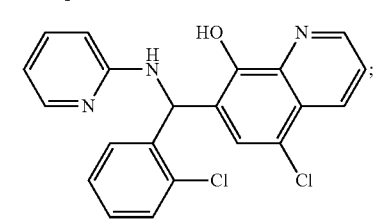
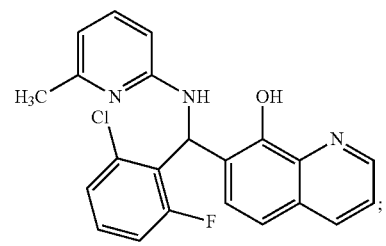
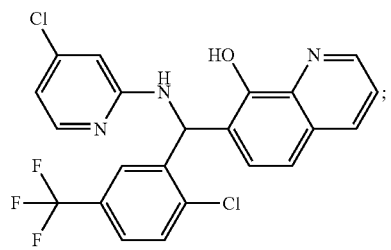
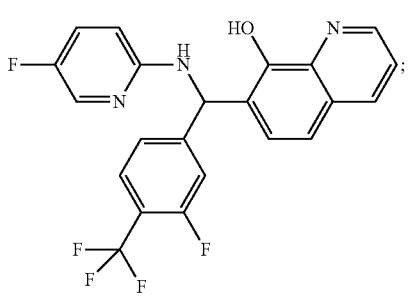

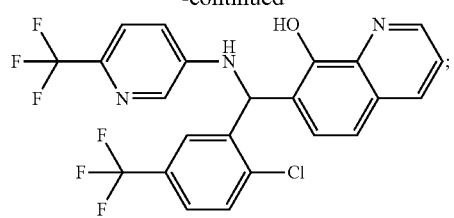
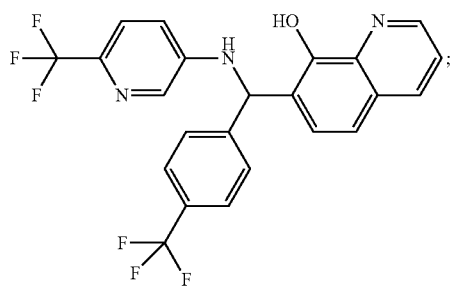
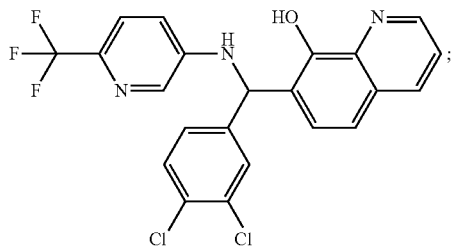
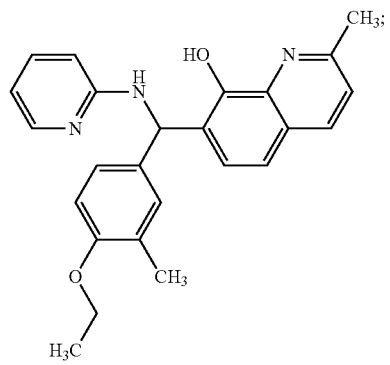
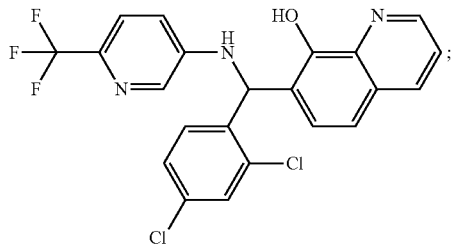
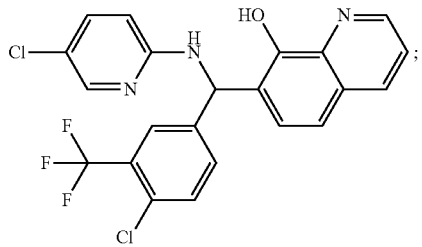
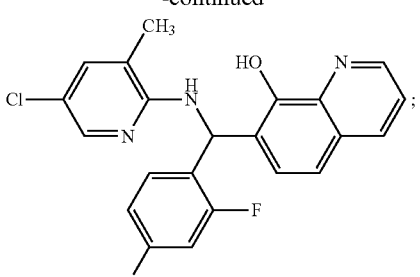
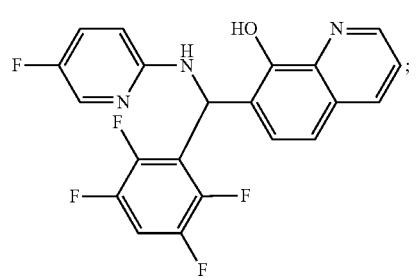
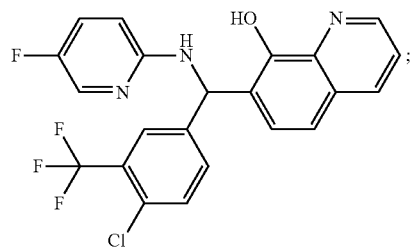
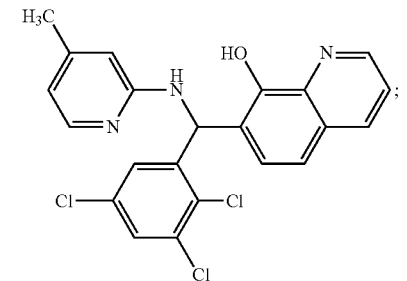
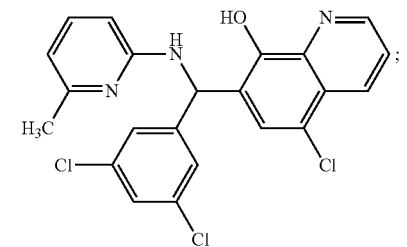
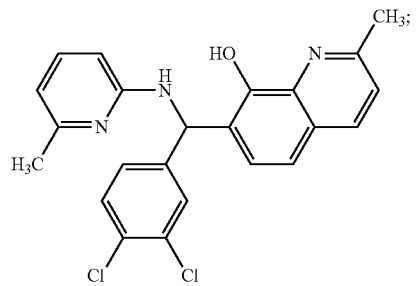

-continued
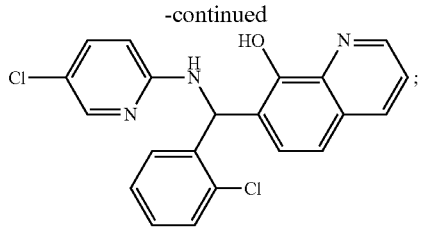
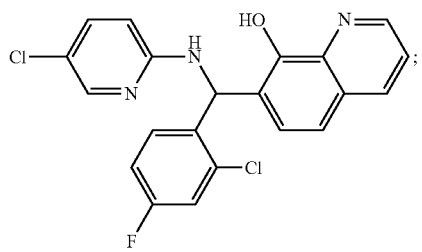
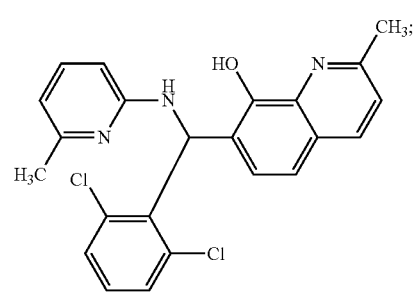
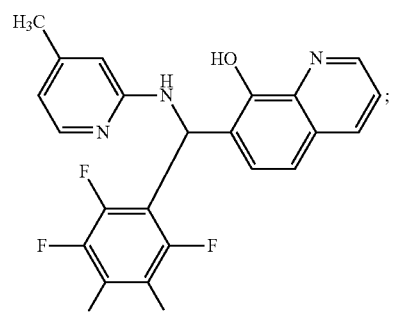
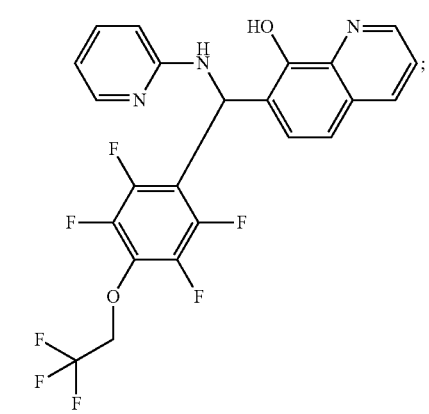
-continued
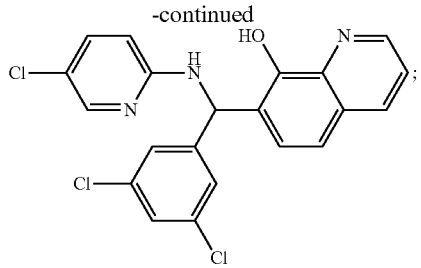
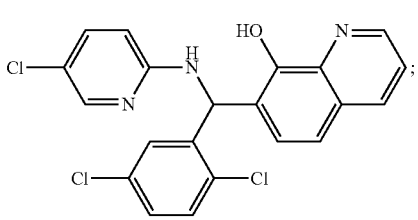
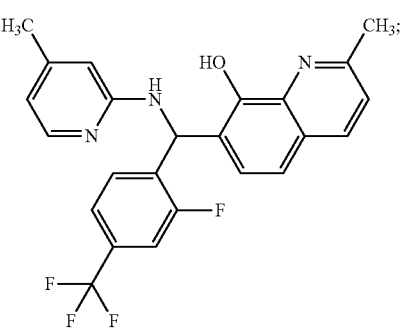
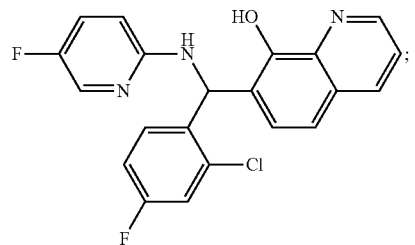
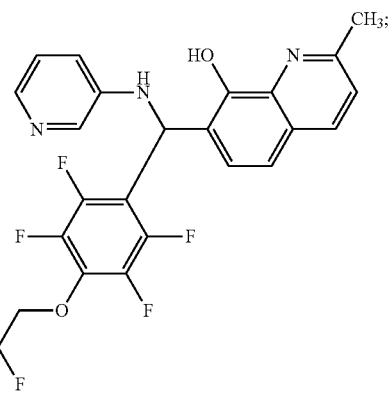
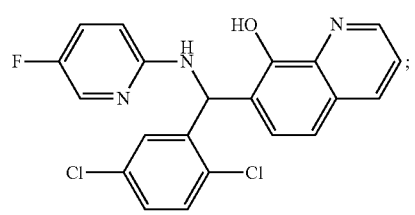

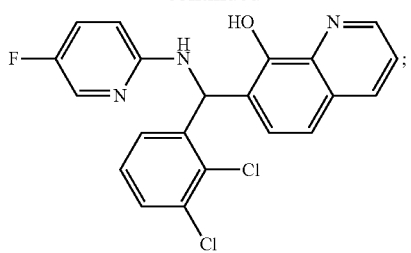
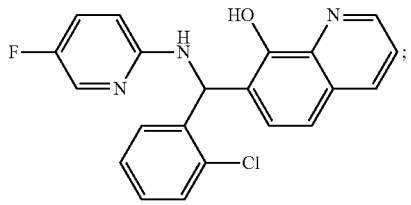
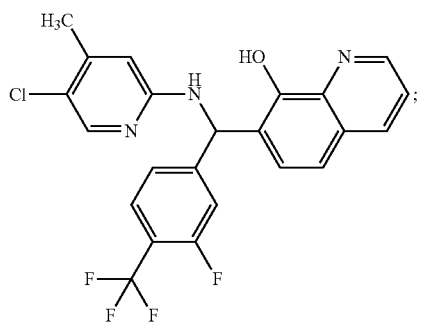
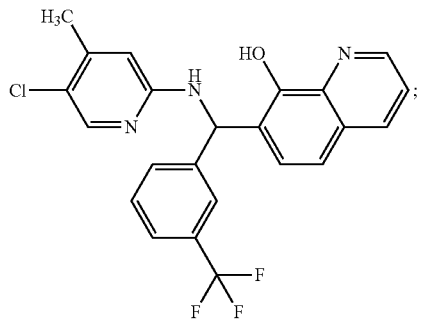
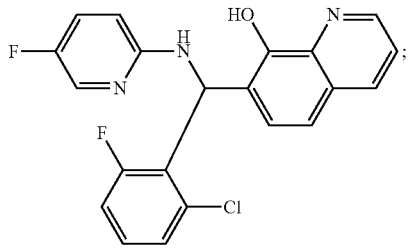
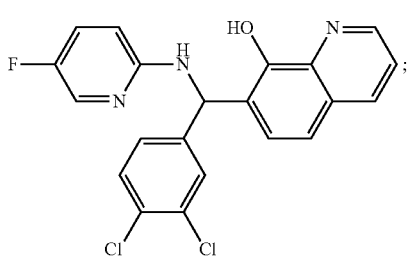
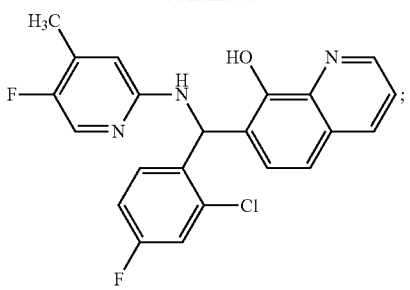
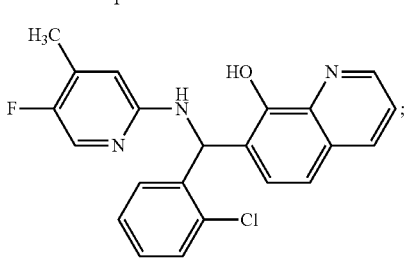
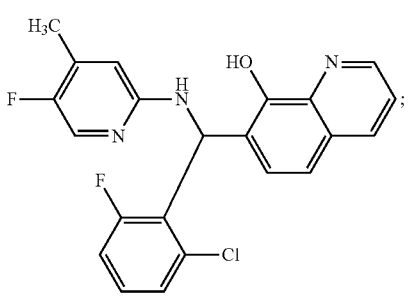
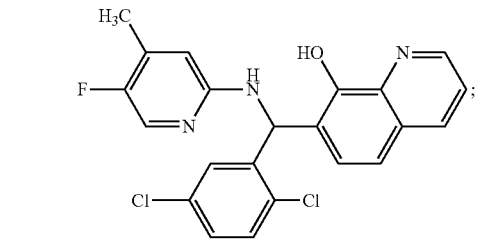
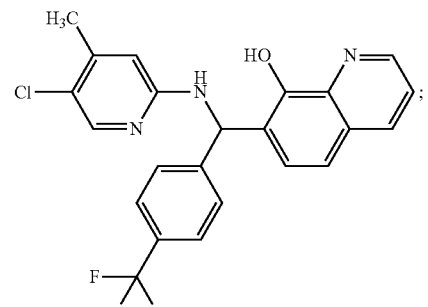
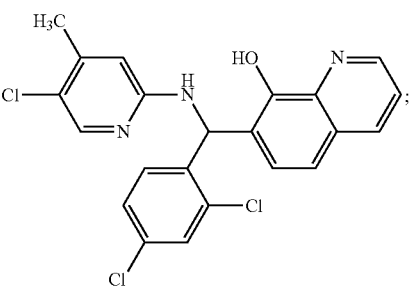

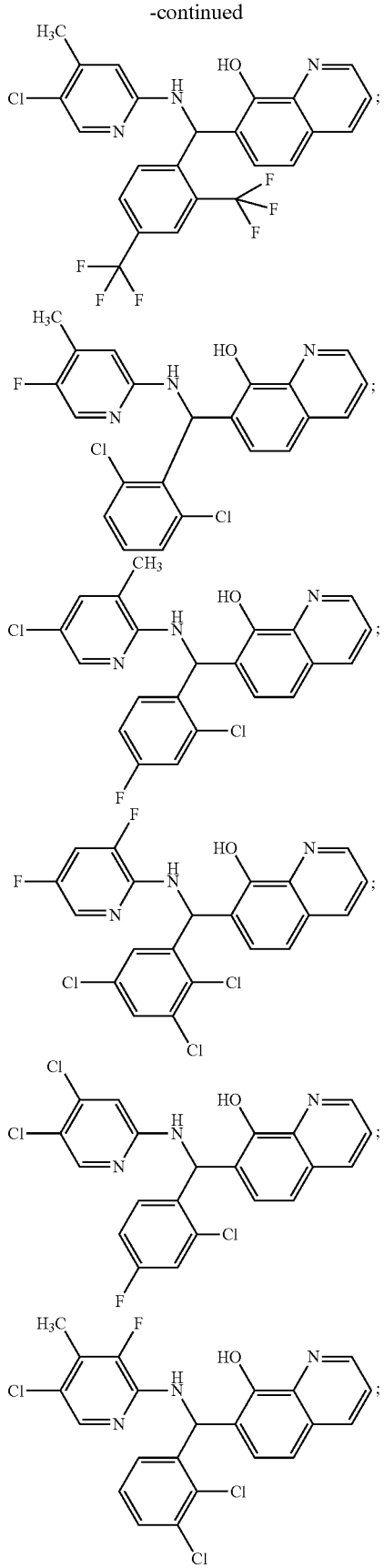
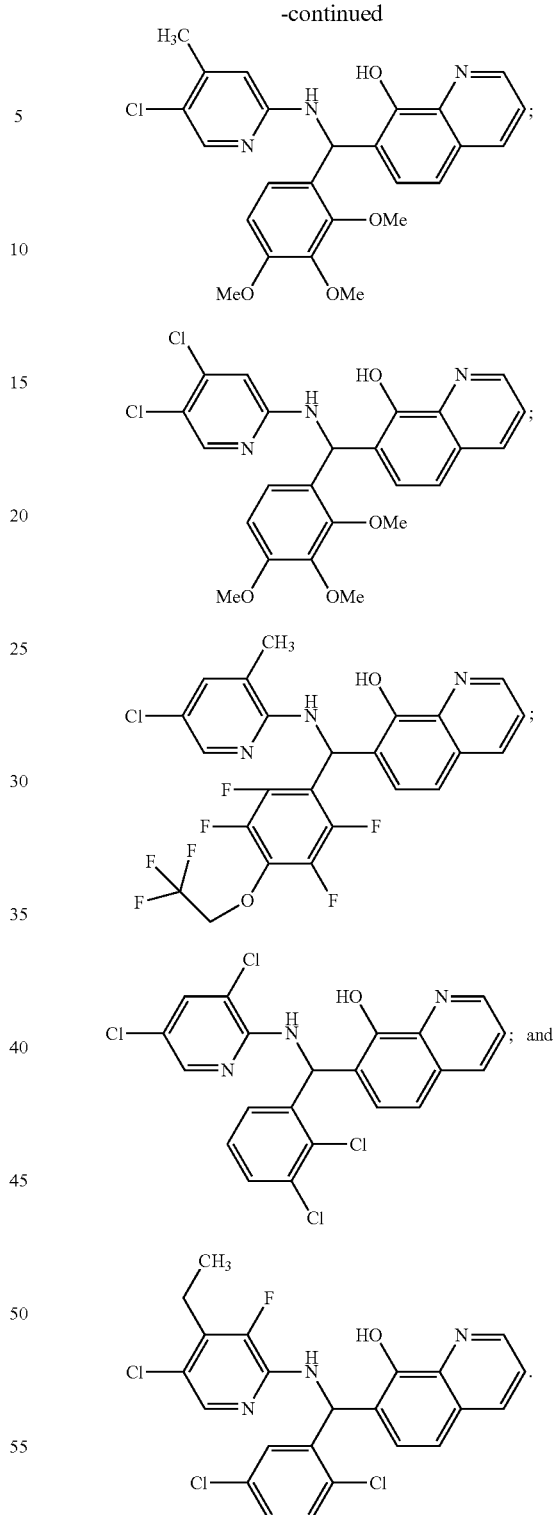
8. A kit comprising (a) a first composition comprising an MDM2 inhibitor and an EGFR inhibitor or (b) a second composition comprising an MDM2 inhibitor and a third composition comprising an EGFR inhibitor according to definitions of claim 1.
* * * * *